United States Patent
Jain et al.

(10) Patent No.: US 11,208,693 B2
(45) Date of Patent: Dec. 28, 2021

(54) METHODS AND SYSTEMS FOR DETERMINING A PREGNANCY-RELATED STATE OF A SUBJECT

(71) Applicant: Mirvie, Inc., South San Francisco, CA (US)

(72) Inventors: Maneesh Jain, South San Francisco, CA (US); Eugeni Namsaraev, South San Francisco, CA (US); Morten Rasmussen, South San Francisco, CA (US); Joan Camunas Soler, South San Francisco, CA (US); Farooq Siddiqui, South San Francisco, CA (US); Mitsu Reddy, South San Francisco, CA (US)

(73) Assignee: Mirvie, Inc., South San Francisco, CA (US)

( * ) Notice: Subject to any disclaimer, the term of this patent is extended or adjusted under 35 U.S.C. 154(b) by 0 days.

(21) Appl. No.: 17/060,534

(22) Filed: Oct. 1, 2020

(65) Prior Publication Data
US 2021/0017598 A1    Jan. 21, 2021

Related U.S. Application Data

(63) Continuation of application No. PCT/US2020/018172, filed on Feb. 13, 2020.

(60) Provisional application No. 62/926,786, filed on Oct. 28, 2019, provisional application No. 62/890,248, filed on Aug. 22, 2019, provisional application No. 62/805,515, filed on Feb. 14, 2019.

(51) Int. Cl.
*C12Q 1/6876* (2018.01)
*G16B 40/00* (2019.01)
*G16B 50/00* (2019.01)

(52) U.S. Cl.
CPC ........... *C12Q 1/6876* (2013.01); *G16B 40/00* (2019.02); *G16B 50/00* (2019.02); *C12Q 2600/158* (2013.01)

(58) Field of Classification Search
None
See application file for complete search history.

(56) References Cited

U.S. PATENT DOCUMENTS

| | | | |
|---|---|---|---|
| 2005/0170444 A1* | 8/2005 | Karumanchi | C07K 16/1217 435/7.92 |
| 2011/0150775 A1 | 6/2011 | Slonim et al. | |
| 2012/0184449 A1* | 7/2012 | Hixson | C12Q 1/6809 506/7 |

FOREIGN PATENT DOCUMENTS

WO    WO-2014193999 A2    12/2014

OTHER PUBLICATIONS

Ziemann et al. Gene name errors are widespread in the scientific literature. 2016. Genome Biology. vol. 17, No. 177, 3 pages. (Year: 2016).*

(Continued)

*Primary Examiner* — Channing S Mahatan
(74) *Attorney, Agent, or Firm* — Wilson Sonsini Goodrich & Rosati

(57) ABSTRACT

The present disclosure provides methods and systems directed to cell-free identification and/or monitoring of pregnancy-related states. A method for identifying or monitoring a presence or susceptibility of a pregnancy-related state of a subject may comprise assaying a cell-free biological sample derived from said subject to detect a set of biomarkers, and analyzing the set of biomarkers with a trained algorithm to determine the presence or susceptibility of the pregnancy-related state.

29 Claims, 38 Drawing Sheets

(56) References Cited

OTHER PUBLICATIONS

Hong et al. Genome-wide approach identifies a novel gene-maternal pre-pregnancy BMI interaction on preterm birth. Jun. 9, 2017. Nature Communications. vol. 8, No. 15608, pp. 1-10, (Year: 2017).*
Leeman et al. Hypertensive Disorders of Pregnancy. Jan. 15, 2016. American Family Physician. vol. 93, No. 2, pp. 121-127. (Year: 2016).*
Ng et al. The Concentration of Circulating Corticotrophin-releasing Hormone mRNA in Maternal Plasma Is Increased in Preeclampsia. 2003. Clinical Chemistry. vol. 49, No. 5, pp. 727-731. (Year: 2003).*
Uzunlar et al. Is there an association between liver type fatty acid binding protein and severity of preeclampsia. 2015. Arch. Gynecol. Obstet. vol. 291, pp. 1069-1074. (Year: 2015).*
Winn et al. (Severe Preeclampsia-Related Changes in Gene Expression at the Maternal-Fetal Interface Include Sialic Acid-Binding Immunoglobulin-Like Lectin-6 and Pappalysin-2. Jan. 1, 2009. vol. 150, Iss. 1, pp. 452-462. (Year: 2009).*
Ngo, et al., Noninvasive blood tests for fetal development predict gestational age and preterm delivery. Science, Jun. 8, 2018; 360: 1133-1136.
PCT/US2020/018172 International Search Report and Written Opinion dated Jul. 14, 2020.
Tounta et al., Noninvasive prenatal diagnosis using cell-free fetal nucleic acids in maternal plasma: Progress overview beyond predictive and personalized diagnosis, EPMA Journal, 2011, vol. 2, pp. 163-171.
"WHO Recommendations on Interventions to Improve Preterm Birth Outcomes," World Health Organization, 2015.

* cited by examiner

| Project | sample dataset description | Gene Discovery | | | | Model Building | | | | | |
|---|---|---|---|---|---|---|---|---|---|---|---|
| | | nSamples | nGenes input | Gene Discovery Model | n_genes_ discovered | sample dataset description | nSamples | model | nGenes used | RMSE null model | RMSE | RSME description |
| DD | 003_GA + 004_PG, min_time_to_deliv <5 | 43 | 15k | min_corr > 0.35 | 130 | same | 43 | linear, elastic net regularization | 28, 50+us | 7.8 (days) | 4.4, 4.2+us (days) | LOOCV |
| DD | 003_GA + 004_PG min_time_to_deliv <7.5 | 59 | 15k | min_corr > 0.30 | 62 | same | 59 | linear, elastic net regularization | 47, 48+us | 11 days | 5.0, 4.9+us (days) | LOOCV |

FIG. 5E

| Condition/product | Testing time |
|---|---|
| Pre-term | T1 |
| Gestational age | T2 |
| Due date | T3 |
| Preeclampsia (pregnancy-related hypertensive disorders ) | T1,T2 |
| Gestational diabetes | T1,T2 |
| Congenital disorder | T3 |
| spontaneous abortion | T1,T2 |
| Placenta previa | T2,T3 |
| Placenta accreta (hemorrhage or excessive bleeding during delivery same? ) | T2,T3 |
| Premature rupture of membrane, PROM | T2,T3 |
| Fetal development, normal and abnormal | T1,T2,T3 |
| IUGR, intrauterine/fetal growth restriction | T2,T3 |
| post-partum depression | T3 |
| Prenatal Metabolic genetic desease | T3 |
| post-partum cardiomyopathy | T3 |

FIG. 14B

METHODS AND SYSTEMS FOR DETERMINING A PREGNANCY-RELATED STATE OF A SUBJECT

CROSS-REFERENCE

This application is a continuation of International Patent Application No. PCT/US2020/018172, filed Feb. 13, 2020, which claims the benefit of U.S. Provisional Patent Application No. 62/805,515, filed Feb. 14, 2019, U.S. Provisional Patent Application No. 62/890,248, filed Aug. 22, 2019, and U.S. Provisional Patent Application No. 62/926,786, filed Oct. 28, 2019, each of which is entirely incorporated by reference herein.

BACKGROUND

Every year, about 15 million pre-term births are reported globally. Pre-term birth may affect as many as about 10% of pregnancies, of which the majority are spontaneous pre-term births. Currently, there may be no meaningful, clinically actionable diagnostic screenings or tests available for many pregnancy-related complications such as pre-term birth. However, pregnancy-related complications such as pre-term birth are a leading cause of neonatal death and of complications later in life. Further, such pregnancy-related complications can cause negative health effects on maternal health. Thus, to make pregnancy as safe as possible, there exists a need for rapid, accurate methods for identifying and monitoring pregnancy-related states that are non-invasive and cost-effective, toward improving maternal and fetal health.

SUMMARY

The present disclosure provides methods, systems, and kits for identifying or monitoring pregnancy-related states by processing cell-free biological samples obtained from or derived from subjects. Cell-free biological samples (e.g., plasma samples) obtained from subjects may be analyzed to identify the pregnancy-related state (which may include, e.g., measuring a presence, absence, or relative assessment of the pregnancy-related state). Such subjects may include subjects with one or more pregnancy-related states and subjects without pregnancy-related states. Pregnancy-related states may include, for example, pre-term birth, full-term birth, gestational age, due date (e.g., due date for an unborn baby or fetus of a subject), onset of labor, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea), and fetal development stages or states (e.g., normal fetal organ function or development, and abnormal fetal organ function or development).

In an aspect, the present disclosure provides a method for identifying a presence or susceptibility of a pregnancy-related state of a subject, comprising assaying transcripts and/or metabolites in a cell-free biological sample derived from the subject to detect a set of biomarkers, and analyzing the set of biomarkers with a trained algorithm to determine the presence or susceptibility of the pregnancy-related state. In some embodiments, the method comprises assaying the transcripts in the cell-free biological sample derived from the subject to detect the set of biomarkers. In some embodiments, the transcripts are assayed with nucleic acid sequencing. In some embodiments, the method comprises assaying the metabolites in the cell-free biological sample derived from the subject to detect the set of biomarkers. In some embodiments, the metabolites are assayed with a metabolomics assay.

In another aspect, the present disclosure provides a method for identifying a presence or susceptibility of a pregnancy-related state of a subject, comprising assaying a cell-free biological sample derived from the subject to detect a set of biomarkers, and analyzing the set of biomarkers with a trained algorithm to determine the presence or susceptibility of the pregnancy-related state among a set of at least three distinct pregnancy-related states at an accuracy of at least about 70%. In some embodiments, the pregnancy-related state is selected from the group consisting of pre-term birth, full-term birth, gestational age, due date, onset of labor, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea), and fetal development stages or states (e.g., normal fetal organ function or development, and abnormal fetal organ function or development). In some embodiments, the pregnancy-related state is a sub-type of pre-term birth, and the at least three distinct pregnancy-related states include at least two distinct sub-types of pre-term birth. In some embodiments, the sub-type of pre-term birth is a molecular sub-type of pre-term birth, and the at least two distinct sub-types of pre-term birth include at least two distinct molecular sub-types of pre-term birth. In some embodiments, the distinct molecular subtypes of pre-term birth comprise a molecular subtype of pre-term birth selected from the group consisting of history of prior pre-term birth, spontaneous pre-term birth, ethnicity specific pre-term birth risk (e.g., among an African-American population), and pre-term premature rupture of membrane (PPROM). In some embodiments, the method further comprises identifying a clinical intervention for the subject based at least in part on the presence or susceptibility of the pregnancy-related state. In some embodiments, the clinical intervention is selected from a plurality of clinical interventions. In some embodiments, the set of biomarkers comprises a genomic locus associated with due date, wherein the genomic locus is selected from the group consisting of genes listed in Table 1 and Table 7. In some embodiments, the set of biomarkers comprises a genomic locus associated with gestational age, wherein the genomic locus is selected from the group consisting of genes listed in Table 2. In some embodiments, the set of biomarkers comprises a genomic locus associated with pre-term birth, wherein the genomic locus is selected from the group consisting of genes listed in Table 5, genes listed in Table 6, genes listed in Table 8, RAB27B, RGS18, CLCN3, B3GNT2, COL24A1, CXCL8, and PTGS2. In some embodiments, the set of biomarkers comprises at least 5 distinct genomic loci. In some embodiments, the set of biomarkers comprises at least 10 distinct genomic loci. In some embodiments, the set of biomarkers comprises at least 25 distinct genomic loci. In some embodiments, the set of biomarkers comprises at least 50 distinct genomic loci. In some embodiments, the set of biomarkers comprises at least 100 distinct genomic loci. In some embodiments, the set of biomarkers comprises at least 150 distinct genomic loci.

In another aspect, the present disclosure provides a method for identifying or monitoring a presence or susceptibility of a pregnancy-related state of a subject, comprising: (a) using a first assay to process a cell-free biological sample derived from said subject to generate a first dataset; (b) using a second assay to process a vaginal or cervical biological sample derived from said subject to generate a second dataset comprising a microbiome profile of said vaginal or cervical biological sample; (c) using an algorithm (e.g., a trained algorithm) to process at least said first dataset and said second dataset to determine said presence or susceptibility of said pregnancy-related state, which trained algorithm has an accuracy of at least about 70% over 50 independent samples; and (d) electronically outputting a report indicative of said presence or susceptibility of the pregnancy-related state of said subject.

In some embodiments, said first assay comprises using cell-free ribonucleic acid (cfRNA) molecules derived from said cell-free biological sample to generate transcriptomic data, using cell-free deoxyribonucleic acid (cfDNA) molecules derived from said cell-free biological sample to generate genomic data, using proteins derived from said cell-free biological sample to generate proteomic data, or using metabolites derived from said cell-free biological sample to generate metabolomic data. In some embodiments, said cell-free biological sample is from a blood of said subject. In some embodiments, said cell-free biological sample is from a urine of said subject.

In some embodiments, said first dataset comprises a first set of biomarkers associated with said pregnancy-related state. In some embodiments, said second dataset comprises a second set of biomarkers associated with said pregnancy-related state. In some embodiments, said second set of biomarkers is different from said first set of biomarkers.

In some embodiments, said pregnancy-related state is selected from the group consisting of pre-term birth, full-term birth, gestational age, due date, onset of labor, pregnancy-related hypertensive disorders, eclampsia, gestational diabetes, a congenital disorder of a fetus of the subject, ectopic pregnancy, spontaneous abortion, stillbirth, post-partum complications, hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions, and fetal development stages or states.

In some embodiments, said pregnancy-related state comprises pre-term birth. In some embodiments, said pregnancy-related state comprises gestational age.

In some embodiments, said cell-free biological sample is selected from the group consisting of cell-free ribonucleic acid (cfRNA), cell-free deoxyribonucleic acid (cfDNA), cell-free fetal DNA (cffDNA), plasma, serum, urine, saliva, amniotic fluid, and derivatives thereof. In some embodiments, said cell-free biological sample is obtained or derived from said subject using an ethylenediaminetetraacetic acid (EDTA) collection tube, a cell-free RNA collection tube, or a cell-free DNA collection tube. In some embodiments, the method further comprises fractionating a whole blood sample of said subject to obtain said cell-free biological sample.

In some embodiments, said first assay comprises a cfRNA assay or a metabolomics assay. In some embodiments, said metabolomics assay comprises targeted mass spectroscopy (MS) or an immune assay. In some embodiments, said cell-free biological sample comprises cfRNA or urine. In some embodiments, said first assay or said second assay comprises quantitative polymerase chain reaction (qPCR). In some embodiments, said first assay or said second assay comprises a home use test configured to be performed in a home setting.

In some embodiments, said trained algorithm determines said presence or susceptibility of said pregnancy-related state of said subject at a sensitivity of at least about 80%. In some embodiments, said trained algorithm determines said presence or susceptibility of said pregnancy-related state of said subject at a sensitivity of at least about 90%. In some embodiments, said trained algorithm determines said presence or susceptibility of said pregnancy-related state of said subject at a sensitivity of at least about 95%.

In some embodiments, said trained algorithm determines said presence or susceptibility of said pregnancy-related state of said subject at a positive predictive value (PPV) of at least about 70%. In some embodiments, said trained algorithm determines said presence or susceptibility of said pregnancy-related state of said subject at a positive predictive value (PPV) of at least about 80%. In some embodiments, said trained algorithm determines said presence or susceptibility of said pregnancy-related state thereof of said subject at a positive predictive value (PPV) of at least about 90%.

In some embodiments, said trained algorithm determines said presence or susceptibility of said pregnancy-related state of said subject with an Area Under Curve (AUC) of at least about 0.90. In some embodiments, said trained algorithm determines said presence or susceptibility of said pregnancy-related state of said subject with an Area Under Curve (AUC) of at least about 0.95. In some embodiments, said trained algorithm determines said presence or susceptibility of said pregnancy-related state of said subject with an Area Under Curve (AUC) of at least about 0.99.

In some embodiments, said subject is asymptomatic for one or more of: pre-term birth, onset of labor, pregnancy-related hypertensive disorders, eclampsia, gestational diabetes, a congenital disorder of a fetus of the subject, ectopic pregnancy, spontaneous abortion, stillbirth, post-partum complications, hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions, and abnormal fetal development stages or states.

In some embodiments, said trained algorithm is trained using at least about 10 independent training samples associated with said presence or susceptibility of said pregnancy-related state. In some embodiments, said trained algorithm is trained using no more than about 100 independent training samples associated with said presence or susceptibility of said pregnancy-related state. In some embodiments, said trained algorithm is trained using a first set of independent training samples associated with a presence or susceptibility of said pregnancy-related state and a second set of independent training samples associated with an absence or no susceptibility of said pregnancy-related state. In some embodiments, the method further comprises using said trained algorithm to process a set of clinical health data of said subject to determine said presence or susceptibility of said pregnancy-related state.

In some embodiments, (a) comprises (i) subjecting said cell-free biological sample to conditions that are sufficient to isolate, enrich, or extract a set of ribonucleic acid (RNA) molecules, deoxyribonucleic acid (DNA) molecules, proteins, or metabolites, and (ii) analyzing said set of RNA molecules, DNA molecules, proteins, or metabolites using said first assay to generate said first dataset. In some embodiments, the method further comprises extracting a set of nucleic acid molecules from said cell-free biological sample, and subjecting said set of nucleic acid molecules to sequencing to generate a set of sequencing reads, wherein said first dataset comprises said set of sequencing reads. In some embodiments, (b) comprises (i) subjecting said vaginal or cervical biological sample to conditions that are sufficient to isolate, enrich, or extract a population of microbes, and (ii) analyzing said population of microbes using said second assay to generate said second dataset.

In some embodiments, said sequencing is massively parallel sequencing. In some embodiments, said sequencing comprises nucleic acid amplification. In some embodiments, said nucleic acid amplification comprises polymerase chain reaction (PCR). In some embodiments, said sequencing comprises use of simultaneous reverse transcription (RT) and polymerase chain reaction (PCR). In some embodiments, the method further comprises using probes configured to selectively enrich said set of nucleic acid molecules corresponding to a panel of one or more genomic loci. In some embodiments, said probes are nucleic acid primers. In some embodiments, said probes have sequence complementarity with nucleic acid sequences of said panel of said one or more genomic loci.

In some embodiments, said panel of said one or more genomic loci comprises at least one genomic locus selected from the group consisting of ACTB, ADAM12, ALPP, ANXA3, APLF, ARG1, AVPR1A, CAMP, CAPN6, CD180, CGA, CGB, CLCN3, CPVL, CSH1, CSH2, CSHL1, CYP3A7, DAPP1, DCX, DEFA4, DGCR14, ELANE, ENAH, EPB42, FABP1, FAM212B-AS1, FGA, FGB, FRMD4B, FRZB, FSTL3, GH2, GNAZ, HAL, HSD17B1, HSD3B1, HSPB8, Immune, ITIH2, KLF9, KNG1, KRT8, LGALS14, LTF, LYPLAL1, MAP3K7CL, MEF2C, MMD, MMP8, MOB1B, NFATC2, OTC, P2RY12, PAPPA, PGLYRP1, PKHD1L1, PKHD1L1, PLAC1, PLAC4, POLE2, PPBP, PSG1, PSG4, PSG7, PTGER3, RAB11A, RAB27B, RAP1GAP, RGS18, RPL23AP7, S100A8, S100A9, S00P, SERPINA7, SLC2A2, SLC38A4, SLC4A1, TBC1D15, VCAN, VGLL1, B3GNT2, COL24A1, CXCL8, and PTGS2.

In some embodiments, said panel of said one or more genomic loci comprises at least 5 distinct genomic loci. In some embodiments, said panel of said one or more genomic loci comprises at least 10 distinct genomic loci.

In some embodiments, said panel of said one or more genomic loci comprises a genomic locus associated with pre-term birth, wherein said genomic locus is selected from the group consisting of ADAM12, ANXA3, APLF, AVPR1A, CAMP, CAPN6, CD180, CGA, CGB, CLCN3, CPVL, CSH2, CSHL1, CYP3A7, DAPP1, DGCR14, ELANE, ENAH, FAM212B-AS1, FRMD4B, GH2, HSPB8, Immune, KLF9, KRT8, LGALS14, LTF, LYPLAL1, MAP3K7CL, MMD, MOB1B, NFATC2, P2RY12, PAPPA, PGLYRP1, PKHD1L1, PKHD1L1, PLAC1, PLAC4, POLE2, PPBP, PSG1, PSG4, PSG7, RAB11A, RAB27B, RAP1GAP, RGS18, RPL23AP7, TBC1D15, VCAN, VGLL1, B3GNT2, COL24A1, CXCL8, and PTGS2.

In some embodiments, said panel of said one or more genomic loci comprises a genomic locus associated with gestational age, wherein said genomic locus is selected from the group consisting of ACTB, ADAM12, ALPP, ANXA3, ARG1, CAMP, CAPN6, CGA, CGB, CSH1, CSH2, CSHL1, CYP3A7, DCX, DEFA4, EPB42, FABP1, FGA, FGB, FRZB, FSTL3, GH2, GNAZ, HAL, HSD17B1, HSD3B1, HSPB8, ITIH2, KNG1, LGALS14, LTF, MEF2C, MMP8, OTC, PAPPA, PGLYRP1, PLAC1, PLAC4, PSG1, PSG4, PSG7, PTGER3, S100A8, S100A9, S100P, SERPINA7, SLC2A2, SLC38A4, SLC4A1, VGLL1, RAB27B, RGS18, CLCN3, B3GNT2, COL24A1, CXCL8, and PTGS2.

In some embodiments, the panel of said one or more genomic loci comprises a genomic locus associated with due date, wherein the genomic locus is selected from the group consisting of genes listed in Table 1 and Table 7. In some embodiments, the panel of said one or more genomic loci comprises a genomic locus associated with gestational age, wherein the genomic locus is selected from the group of genes listed in Table 2. In some embodiments, the panel of said one or more genomic loci comprises a genomic locus associated with pre-term birth, wherein the genomic locus is selected from the group consisting of genes listed in Table 5, genes listed in Table 6, genes listed in Table 8, RAB27B, RGS18, CLCN3, B3GNT2, COL24A1, CXCL8, and PTGS2.

In some embodiments, the panel of the one or more genomic loci comprises at least 5 distinct genomic loci. In some embodiments, the panel of the one or more genomic loci comprises at least 10 distinct genomic loci. In some embodiments, the panel of the one or more genomic loci comprises at least 25 distinct genomic loci. In some embodiments, the panel of the one or more genomic loci comprises at least 50 distinct genomic loci. In some embodiments, the panel of the one or more genomic loci comprises at least 100 distinct genomic loci. In some embodiments, the panel of the one or more genomic loci comprises at least 150 distinct genomic loci.

In some embodiments, said cell-free biological sample is processed without nucleic acid isolation, enrichment, or extraction.

In some embodiments, said report is presented on a graphical user interface of an electronic device of a user. In some embodiments, said user is said subject.

In some embodiments, the method further comprises determining a likelihood of said determination of said presence or susceptibility of said pregnancy-related state of said subject.

In some embodiments, said trained algorithm comprises a supervised machine learning algorithm. In some embodiments, said supervised machine learning algorithm comprises a deep learning algorithm, a support vector machine (SVM), a neural network, or a Random Forest.

In some embodiments, the method further comprises providing said subject with a therapeutic intervention for said presence or susceptibility of said pregnancy-related state. In some embodiments, said therapeutic intervention comprises hydroxyprogesterone caproate, a vaginal progesterone, a natural progesterone IVR product, an prostaglandin F2 alpha receptor antagonist, or a beta2-adrenergic receptor agonist.

In some embodiments, the method further comprises monitoring said presence or susceptibility of said pregnancy-related state, wherein said monitoring comprises assessing said presence or susceptibility of said pregnancy-related state of said subject at a plurality of time points, wherein said assessing is based at least on said presence or susceptibility of said pregnancy-related state determined in (d) at each of said plurality of time points.

In some embodiments, a difference in said assessment of said presence or susceptibility of said pregnancy-related state of said subject among said plurality of time points is indicative of one or more clinical indications selected from the group consisting of: (i) a diagnosis of said presence or susceptibility of said pregnancy-related state of said subject, (ii) a prognosis of said presence or susceptibility of said pregnancy-related state of said subject, and (iii) an efficacy or non-efficacy of a course of treatment for treating said presence or susceptibility of said pregnancy-related state of said subject.

In some embodiments, the method further comprises stratifying said pre-term birth by using said trained algorithm to determine a molecular sub-type of said pre-term birth from among a plurality of distinct molecular subtypes of pre-term birth. In some embodiments, the plurality of distinct molecular subtypes of pre-term birth comprises a molecular subtype of pre-term birth selected from the group consisting of history of prior pre-term birth, spontaneous pre-term birth, ethnicity specific pre-term birth risk (e.g., among an African-American population), and pre-term premature rupture of membrane (PPROM).

In another aspect, the present disclosure provides a computer-implemented method for predicting a risk of pre-term birth of a subject, comprising: (a) receiving clinical health data of said subject, wherein said clinical health data comprises a plurality of quantitative or categorical measures of said subject; (b) using an algorithm (e.g., a trained algorithm) to process said clinical health data of said subject to determine a risk score indicative of said risk of pre-term birth of said subject; and (c) electronically outputting a report indicative of said risk score indicative of said risk of pre-term birth of said subject.

In some embodiments, said clinical health data comprises one or more quantitative measures selected from the group consisting of age, weight, height, body mass index (BMI), blood pressure, heart rate, glucose levels, number of previous pregnancies, and number of previous births. In some embodiments, said clinical health data comprises one or more categorical measures selected from the group consisting of race, ethnicity, history of medication or other clinical treatment, history of tobacco use, history of alcohol consumption, daily activity or fitness level, genetic test results, blood test results, imaging results, and fetal screening results.

In some embodiments, said trained algorithm determines said risk of pre-term birth of said subject at a sensitivity of at least about 80%. In some embodiments, said trained algorithm determines said risk of pre-term birth of said subject at a specificity of at least about 80%. In some embodiments, said trained algorithm determines said risk of pre-term birth of said subject at a positive predictive value (PPV) of at least about 80%. In some embodiments, said trained algorithm determines said risk of pre-term birth of said subject at a negative predictive value (NPV) of at least about 80%. In some embodiments, said trained algorithm determines said risk of pre-term birth of said subject with an Area Under Curve (AUC) of at least about 0.9.

In some embodiments, said subject is asymptomatic for one or more of: pre-term birth, onset of labor, pregnancy-related hypertensive disorders, eclampsia, gestational diabetes, a congenital disorder of a fetus of said subject, ectopic pregnancy, spontaneous abortion, stillbirth, post-partum complications, hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions, and abnormal fetal development stages or states.

In some embodiments, said trained algorithm is trained using at least about 10 independent training samples associated with pre-term birth. In some embodiments, said trained algorithm is trained using no more than about 100 independent training samples associated with pre-term birth. In some embodiments, said trained algorithm is trained using a first set of independent training samples associated with a presence of pre-term birth and a second set of independent training samples associated with an absence of pre-term birth.

In some embodiments, said report is presented on a graphical user interface of an electronic device of a user. In some embodiments, said user is said subject.

In some embodiments, said trained algorithm comprises a supervised machine learning algorithm. In some embodiments, said supervised machine learning algorithm comprises a deep learning algorithm, a support vector machine (SVM), a neural network, or a Random Forest.

In some embodiments, the method further comprises providing said subject with a therapeutic intervention based at least in part on said risk score indicative of said risk of pre-term birth. In some embodiments, said therapeutic intervention comprises hydroxyprogesterone caproate, a vaginal progesterone, a natural progesterone IVR product, an prostaglandin F2 alpha receptor antagonist, or a beta2-adrenergic receptor agonist.

In some embodiments, the method further comprises monitoring said risk of pre-term birth, wherein said monitoring comprises assessing said risk of pre-term birth of said subject at a plurality of time points, wherein said assessing is based at least on said risk score indicative of said risk of pre-term birth determined in (b) at each of said plurality of time points.

In some embodiments, the method further comprises refining said risk score indicative of said risk of pre-term birth of said subject by performing one or more subsequent clinical tests for said subject, and processing results from said one or more subsequent clinical tests using a trained algorithm to determine an updated risk score indicative of said risk of pre-term birth of said subject. In some embodiments, said one or more subsequent clinical tests comprise an ultrasound imaging or a blood test. In some embodiments, said risk score comprises a likelihood of said subject having a pre-term birth within a pre-determined duration of time.

In some embodiments, said pre-determined duration of time is about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1.5 days, about 2 days, about 2.5 days, about 3 days, about 3.5 days, about 4 days, about 4.5 days, about 5 days, about 5.5 days, about 6 days, about 6.5 days, about 7 days, about 8 days, about 9 days, about 10 days, about 12 days, about 14 days, about 3 weeks, about 4 weeks, about 5 weeks, about 6 weeks, about 7 weeks, about 8 weeks, about 9 weeks, about 10 weeks, about 11 weeks, about 12 weeks, about 13 weeks, or more than about 13 weeks.

In another aspect, the present disclosure provides a computer system for predicting a risk of pre-term birth of a subject, comprising: a database that is configured to store clinical health data of said subject, wherein said clinical health data comprises a plurality of quantitative or categorical measures of said subject; and one or more computer processors operatively coupled to said database, wherein said one or more computer processors are individually collectively programmed to: (i) use an algorithm (e.g., a trained algorithm) to process said clinical health data of said subject to determine a risk score indicative of said risk of pre-term birth of said subject; and (ii) electronically output a report indicative of said risk score indicative of said risk of pre-term birth of said subject.

In some embodiments, the computer system further comprises an electronic display operatively coupled to said one or more computer processors, wherein said electronic display comprises a graphical user interface that is configured to display said report.

In another aspect, the present disclosure provides a non-transitory computer readable medium comprising machine-executable code that, upon execution by one or more computer processors, implements a method for predicting a risk of pre-term birth of a subject, said method comprising: (a) receiving clinical health data of said subject, wherein said clinical health data comprises a plurality of quantitative or categorical measures of said subject; (b) using an algorithm (e.g., a trained algorithm) to process said clinical health data of said subject to determine a risk score indicative of said risk of pre-term birth of said subject; and (c) electronically outputting a report indicative of said risk score indicative of said risk of pre-term birth of said subject.

In another aspect, the present disclosure provides a method for determining a due date, due date range, or gestational age of a fetus of a pregnant subject, comprising assaying a cell-free biological sample derived from said pregnant subject to detect a set of biomarkers, and analyzing said set of biomarkers with a trained algorithm to determine said due date, due date range, or gestational age of said fetus.

In some embodiments, the method further comprises analyzing an estimated due date of said fetus of said pregnant subject using said trained algorithm, wherein said estimated due date is generated from ultrasound measurements of said fetus. In some embodiments, said set of biomarkers comprises a genomic locus associated with due date, wherein said genomic locus is selected from the group of genes listed in Table 1 and Table 7.

In some embodiments, said set of biomarkers comprises at least 5 distinct genomic loci. In some embodiments, said set of biomarkers comprises at least 10 distinct genomic loci. In some embodiments, said set of biomarkers comprises at least 25 distinct genomic loci. In some embodiments, said set of biomarkers comprises at least 50 distinct genomic loci. In some embodiments, said set of biomarkers comprises at least 100 distinct genomic loci. In some embodiments, said set of biomarkers comprises at least 150 distinct genomic loci.

In some embodiments, the method further comprises identifying a clinical intervention for said pregnant subject based at least in part on said determined due date. In some embodiments, said clinical intervention is selected from a plurality of clinical interventions.

In some embodiments, said time-to-delivery is less than 7.5 weeks. In some embodiments, said genomic locus is selected from ACKR2, AKAP3, ANO5, C1orf21, C2orf42, CARNS1, CASC15, CCDC102B, CDC45, CDIPT, CMTM1, COPS8, CTD-2267D19.3, CTD-2349P21.9, CXorf65, DDX11L1, DGUOK, DPAGT1, EIF4A1P2, FANK1, FERMT1, FKRP, GAMT, GOLGA6L4, KLLN, LINC01347, LTA, MAPK12, METRN, MKRN4P, MPC2, MYL12BP1, NME4, NPM1P30, PCLO, PIF1, PTP4A3, RIMKLB, RP13-88F20.1, S100B, SIGLEC14, SLAIN1, SPATA33, TFAP2C, TMSB4XP8, TRGV10, and ZNF124.

In some embodiments, said time-to-delivery is less than 5 weeks. In some embodiments, said genomic locus is selected from C2orf68, CACNB3, CD40, CDKL5, CTBS, CTD-2272G21.2, CXCL8, DHRS7B, EIF5A2, IFITM3, MIR24-2, MTSS1, MYSM1, NCK1-AS1, NR1H4, PDE1C, PEMT, PEX7, PIF1, PPP2R3A, RABIF, SIGLEC14, SLC25A53, SPANXN4, SUPT3H, ZC2HC1C, ZMYM1, and ZNF124.

In some embodiments, said time-to-delivery is less than 7.5 weeks. In some embodiments, said genomic locus is selected from ACKR2, AKAP3, ANO5, C1orf21, C2orf42, CARNS1, CASC15, CCDC102B, CDC45, CDIPT, CMTM1, collectionga, COPS8, CTD-2267D19.3, CTD-2349P21.9, DDX11L1, DGUOK, DPAGT1, EIF4A1P2, FANK1, FERMT1, FKRP, GAMT, GOLGA6L4, KLLN, LINC01347, LTA, MAPK12, METRN, MPC2, MYL12BP1, NME4, NPM1P30, PCLO, PIF1, PTP4A3, RIMKLB, RP13-88F20.1, S100B, SIGLEC14, SLAIN1, SPATA33, STAT1, TFAP2C, TMEM94, TMSB4XP8, TRGV10, ZNF124, and ZNF713.

In some embodiments, said time-to-delivery is less than 5 weeks. In some embodiments, said genomic locus is selected from ATP6V1E1P1, ATP8A2, C2orf68, CACNB3, CD40, CDKL4, CDKL5, CEP152, CLEC4D, COL18A1, collectionga, COX16, CTBS, CTD-2272G21.2, CXCL2, CXCL8, DHRS7B, DPPA4, EIF5A2, FERMT1, GNB1L, IFITM3, KATNAL1, LRCH4, MBD6, MIR24-2, MTSS1, MYSM1, NCK1-AS1, NPIPB4, NR1H4, PDE1C, PEMT, PEX7, PIF1, PPP2R3A, PXDN, RABIF, SERTAD3, SIGLEC14, SLC25A53, SPANXN4, SSH3, SUPT3H, TMEM150C, TNFAIP6, UPP1, XKR8, ZC2HC1C, ZMYM1, and ZNF124.

In some embodiments, said trained algorithm comprises a linear regression model or an ANOVA model. In some embodiments, said ANOVA model determines a maximum-likelihood time window corresponding to said due date from among a plurality of time windows. In some embodiments, said maximum-likelihood time window corresponds to a time-to-delivery of 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks. In some embodiments, said ANOVA model determines a probability or likelihood of a time window corresponding to said due date from among a plurality of time windows. In some embodiments, said ANOVA model calculates a probability-weighted average across said plurality of time windows to determine an average or expected time window distance.

In another aspect, the present disclosure provides a method for identifying or monitoring a presence or susceptibility of a pregnancy-related state of a subject, comprising: (a) using a first assay to process a first cell-free biological sample derived from the subject to generate a first dataset; (b) based at least in part on the first dataset generated in (a), using a second assay different from the first assay to process a second cell-free biological sample derived from the subject to generate a second dataset indicative of the presence or susceptibility of the pregnancy-related state at a specificity greater than the first dataset; (c) using a trained algorithm to process at least the second dataset to determine the presence or susceptibility of the pregnancy-related state, which trained algorithm has an accuracy of at least about 70% over 50 independent samples; and (d) electronically outputting a report indicative of the presence or susceptibility of the pregnancy-related state of the subject.

In some embodiments, the first assay comprises using cell-free ribonucleic acid (cfRNA) molecules derived from the first cell-free biological sample to generate transcriptomic data, using cell-free deoxyribonucleic acid (cfDNA) molecules derived from the first cell-free biological sample to generate genomic data, using proteins derived from the first cell-free biological sample to generate proteomic data, or using metabolites derived from the first cell-free biological sample to generate metabolomic data. In some embodiments, the first cell-free biological sample is from a blood of the subject. In some embodiments, the first cell-free biological sample is from a urine of the subject. In some embodiments, the first dataset comprises a first set of biomarkers associated with the pregnancy-related state. In some embodiments, the second dataset comprises a second set of biomarkers associated with the pregnancy-related state. In some embodiments, the second set of biomarkers is different from the first set of biomarkers.

In some embodiments, the pregnancy-related state is selected from the group consisting of pre-term birth, full-term birth, gestational age, due date, onset of labor, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea), and fetal development stages or states (e.g., normal fetal organ function or development, and abnormal fetal organ function or development). In some embodiments, the pregnancy-related state comprises pre-term birth. In some embodiments, the pregnancy-related state comprises gestational age. In some embodiments, the cell-free biological sample is selected from the group consisting of cell-free ribonucleic acid (cfRNA), cell-free deoxyribonucleic acid (cfDNA), cell-free fetal DNA (cffDNA), plasma, serum, urine, saliva, amniotic fluid, and derivatives thereof. In some embodiments, the first cell-free biological sample or the second cell-free biological sample is obtained or derived from the subject using an ethylenediaminetetraacetic acid (EDTA) collection tube, a cell-free RNA collection tube, or a cell-free DNA collection tube. In some embodiments, the method further comprises fractionating a whole blood sample of the subject to obtain the first cell-free biological sample or the second cell-free biological sample. In some embodiments, (i) the first assay comprises a cfRNA assay and the second assay comprises a metabolomics assay, or (ii) the first assay comprises a metabolomics assay and the second assay comprises a cfRNA assay. In some embodiments, (i) the first cell-free biological sample comprises cfRNA and the second cell-free biological sample comprises urine, or (ii) the first cell-free biological sample comprises urine and the second cell-free biological sample comprises cfRNA. In some embodiments, the first assay or the second assay comprises quantitative polymerase chain reaction (qPCR). In some embodiments, the first assay or the second assay comprises a home use test configured to be performed in a home setting. In some embodiments, the first assay or the second assay comprises a metabolomics assay. In some embodiments, the metabolomics assay comprises targeted mass spectroscopy (MS) or an immune assay.

In some embodiments, the first dataset is indicative of the presence or susceptibility of the pregnancy-related state at a sensitivity of at least about 80%. In some embodiments, the first dataset is indicative of the presence or susceptibility of the pregnancy-related state at a sensitivity of at least about 90%. In some embodiments, the first dataset is indicative of the presence or susceptibility of the pregnancy-related state at a sensitivity of at least about 95%. In some embodiments, the first dataset is indicative of the presence or susceptibility of the pregnancy-related state at a positive predictive value (PPV) of at least about 70%. In some embodiments, the first dataset is indicative of the presence or susceptibility of the pregnancy-related state at a positive predictive value (PPV) of at least about 80%. In some embodiments, the first dataset is indicative of the presence or susceptibility of the pregnancy-related state at a positive predictive value (PPV) of at least about 90%. In some embodiments, the second dataset is indicative of the presence or susceptibility of the pregnancy-related state at a specificity of at least about 90%. In some embodiments, the second dataset is indicative of the presence or susceptibility of the pregnancy-related state at a specificity of at least about 95%. In some embodiments, the second dataset is indicative of the presence or susceptibility of the pregnancy-related state at a specificity of at least about 99%. In some embodiments, the second dataset is indicative of the presence or susceptibility of the pregnancy-related state at a negative predictive value (NPV) of at least about 90%. In some embodiments, the second dataset is indicative of the presence or susceptibility of the pregnancy-related state at a negative predictive value (NPV) of at least about 95%. In some embodiments, the second dataset is indicative of the presence or susceptibility of the pregnancy-related state at a negative predictive value (NPV) of at least about 99%. In some embodiments, the trained algorithm determines the presence or susceptibility of the pregnancy-related state of the subject with an Area Under Curve (AUC) of at least about 0.90. In some embodiments, the trained algorithm determines the presence or susceptibility of the pregnancy-related state of the subject with an Area Under Curve (AUC) of at least about 0.95. In some embodiments, the trained algorithm determines the presence or susceptibility of the pregnancy-related state of the subject with an Area Under Curve (AUC) of at least about 0.99.

In some embodiments, the subject is asymptomatic for one or more of: pre-term birth, onset of labor, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea), and abnormal fetal development stages or states (e.g., abnormal fetal organ function or development). In some embodiments, the trained algorithm is trained using at least about 10 independent training samples associated with the pregnancy-related state. In some embodiments, the trained algorithm is trained using no more than about 100 independent training samples associated with the pregnancy-related state. In some embodiments, the trained algorithm is trained using a first set of independent training samples associated with a presence of the pregnancy-related state and a second set of independent training samples associated with an absence of the pregnancy-related state. In some embodiments, the method further comprises using the trained algorithm to process the first dataset to determine the presence or susceptibility of the pregnancy-related state. In some embodiments, the method further comprises using the trained algorithm to process a set of clinical health data of the subject to determine the presence or susceptibility of the pregnancy-related state.

In some embodiments, (a) comprises (i) subjecting the first cell-free biological sample to conditions that are sufficient to isolate, enrich, or extract a first set of ribonucleic acid (RNA) molecules, deoxyribonucleic acid (DNA) molecules, proteins, or metabolites, and (ii) analyzing the first set of RNA molecules, DNA molecules, proteins, or metabolites using the first assay to generate the first dataset. In some embodiments, the method further comprises extracting a first set of nucleic acid molecules from the first cell-free biological sample, and subjecting the first set of nucleic acid molecules to sequencing to generate a first set of sequencing reads, wherein the first dataset comprises the first set of sequencing reads. In some embodiments, the method further comprises extracting a first set of metabolites from the first cell-free biological sample, and assaying the first set of metabolites to generate the first dataset In some embodiments, (b) comprises (i) subjecting the second cell-free biological sample to conditions that are sufficient to isolate, enrich, or extract a second set of ribonucleic acid (RNA) molecules, deoxyribonucleic acid (DNA) molecules, proteins, or metabolites, and (ii) analyzing the second set of RNA molecules, DNA molecules, proteins, or metabolites using the second assay to generate the second dataset. In some embodiments, the method further comprises extracting a second set of nucleic acid molecules from the second cell-free biological sample, and subjecting the second set of nucleic acid molecules to sequencing to generate a second set of sequencing reads, wherein the second dataset comprises the second set of sequencing reads. In some embodiments, the method further comprises extracting a second set of metabolites from the second cell-free biological sample, and assaying the second set of metabolites to generate the second dataset. In some embodiments, the sequencing is massively parallel sequencing. In some embodiments, the sequencing comprises nucleic acid amplification. In some embodiments, the nucleic acid amplification comprises polymerase chain reaction (PCR). In some embodiments, the sequencing comprises use of simultaneous reverse transcription (RT) and polymerase chain reaction (PCR).

In some embodiments, the method further comprises using probes configured to selectively enrich the first set of nucleic acid molecules or the second set of nucleic acid molecules corresponding to a panel of one or more genomic loci. In some embodiments, the probes are nucleic acid primers. In some embodiments, the probes have sequence complementarity with nucleic acid sequences of the panel of the one or more genomic loci. In some embodiments, the panel of the one or more genomic loci comprises at least one genomic locus selected from the group consisting of ACTB, ADAM12, ALPP, ANXA3, APLF, ARG1, AVPR1A, CAMP, CAPN6, CD180, CGA, CGB, CLCN3, CPVL, CSH1, CSH2, CSHL1, CYP3A7, DAPP1, DCX, DEFA4, DGCR14, ELANE, ENAH, EPB42, FABP1, FAM212B-AS1, FGA, FGB, FRMD4B, FRZB, FSTL3, GH2, GNAZ, HAL, HSD17B1, HSD3B1, HSPB8, Immune, ITIH2, KLF9, KNG1, KRT8, LGALS14, LTF, LYPLAL1, MAP3K7CL, MEF2C, MMD, MMP8, MOB1B, NFATC2, OTC, P2RY12, PAPPA, PGLYRP1, PKHD1L1, PKHD1L1, PLAC1, PLAC4, POLE2, PPBP, PSG1, PSG4, PSG7, PTGER3, RAB11A, RAB27B, RAP1GAP, RGS18, RPL23AP7, S100A8, S100A9, S100P, SERPINA7, SLC2A2, SLC38A4, SLC4A1, TBC1D15, VCAN, VGLL1, B3GNT2, COL24A1, CXCL8, and PTGS2. In some embodiments, the panel of the one or more genomic loci comprises at least 5 distinct genomic loci. In some embodiments, the panel of the one or more genomic loci comprises at least 10 distinct genomic loci. In some embodiments, the panel of the one or more genomic loci comprises a genomic locus associated with pre-term birth, wherein said genomic locus is selected from the group consisting of ADAM12, ANXA3, APLF, AVPR1A, CAMP, CAPN6, CD180, CGA, CGB, CLCN3, CPVL, CSH2, CSHL1, CYP3A7, DAPP1, DGCR14, ELANE, ENAH, FAM212B-AS1, FRMD4B, GH2, HSPB8, Immune, KLF9, KRT8, LGALS14, LTF, LYPLAL1, MAP3K7CL, MMD, MOB1B, NFATC2, P2RY12, PAPPA, PGLYRP1, PKHD1L1, PKHD1L1, PLAC1, PLAC4, POLE2, PPBP, PSG1, PSG4, PSG7, RAB11A, RAB27B, RAP1GAP, RGS18, RPL23AP7, TBC1D15, VCAN, VGLL1, B3GNT2, COL24A1, CXCL8, and PTGS2. In some embodiments, the panel of the one or more genomic loci comprises a genomic locus associated with gestational age, wherein said genomic locus is selected from the group consisting of ACTB, ADAM12, ALPP, ANXA3, ARG1, CAMP, CAPN6, CGA, CGB, CSH1, CSH2, CSHL1, CYP3A7, DCX, DEFA4, EPB42, FABP1, FGA, FGB, FRZB, FSTL3, GH2, GNAZ, HAL, HSD17B1, HSD3B1, HSPB8, ITIH2, KNG1, LGALS14, LTF, MEF2C, MMP8, OTC, PAPPA, PGLYRP1, PLAC1, PLAC4, PSG1, PSG4, PSG7, PTGER3, S100A8, S100A9, S100P, SERPINA7, SLC2A2, SLC38A4, SLC4A1, VGLL1, B3GNT2, COL24A1, CXCL8, and PTGS2. In some embodiments, the panel of said one or more genomic loci comprises a genomic locus associated with due date, wherein the genomic locus is selected from the group of genes listed in Table 1 and Table 7. In some embodiments, the panel of said one or more genomic loci comprises a genomic locus associated with gestational age, wherein the genomic locus is selected from the group of genes listed in Table 2. In some embodiments, the panel of said one or more genomic loci comprises a genomic locus associated with pre-term birth, wherein the genomic locus is selected from the group of genes listed in Table 5, genes listed in Table 6, genes listed in Table 8, RAB27B, RGS18, CLCN3, B3GNT2, COL24A1, CXCL8, and PTGS2. In some embodiments, the panel of the one or more genomic loci comprises at least 5 distinct genomic loci. In some embodiments, the panel of the one or more genomic loci comprises at least 10 distinct genomic loci. In some embodiments, the panel of the one or more genomic loci comprises at least 25 distinct genomic loci. In some embodiments, the panel of the one or more genomic loci comprises at least 50 distinct genomic loci. In some embodiments, the panel of the one or more genomic loci comprises at least 100 distinct genomic loci. In some embodiments, the panel of the one or more genomic loci comprises at least 150 distinct genomic loci. In some embodiments, the first cell-free biological sample or the second cell-free biological sample is processed without nucleic acid isolation, enrichment, or extraction. In some embodiments, the report is presented on a graphical user interface of an electronic device of a user. In some embodiments, the user is the subject.

In some embodiments, the method further comprises determining a likelihood of the determination of the presence or susceptibility of the pregnancy-related state of the subject. In some embodiments, the trained algorithm comprises a supervised machine learning algorithm. In some embodiments, the supervised machine learning algorithm comprises a deep learning algorithm, a support vector machine (SVM), a neural network, or a Random Forest. In some embodiments, the method further comprises providing the subject with a therapeutic intervention for the presence or susceptibility of the pregnancy-related state. In some embodiments, therapeutic intervention comprises a progesterone treatment such as hydroxyprogesterone caproate (e.g., 17-alpha hydroxyprogesterone caproate (17-P), LPCN 1107 from Lipocine, Makena from AMAG Pharma), a vaginal progesterone, or a natural progesterone IVR product (e.g., DARE-FRT1 (JNP-0301) from Juniper Pharma); a prostaglandin F2 alpha receptor antagonist (e.g., OBE022 from ObsEva); or a beta2-adrenergic receptor agonist (e.g., bedoradrine sulfate (MN-221) from MediciNova). Therapeutic interventions may be described by, for example, "WHO Recommendations on Interventions to Improve Pre-term Birth Outcomes," World Health Organization, 2015, which is hereby incorporated by reference in its entirety. In some embodiments, the method further comprises monitoring the presence or susceptibility of the pregnancy-related state, wherein the monitoring comprises assessing the presence or susceptibility of the pregnancy-related state of the subject at a plurality of time points, wherein the assessing is based at least on the presence or susceptibility of pregnancy-related state determined in (d) at each of the plurality of time points. In some embodiments, a difference in the assessment of the presence or susceptibility of the pregnancy-related state of the subject among the plurality of time points is indicative of one or more clinical indications selected from the group consisting of: (i) a diagnosis of the presence or susceptibility of the pregnancy-related state of the subject, (ii) a prognosis of the presence or susceptibility of the pregnancy-related state of the subject, and (iii) an efficacy or non-efficacy of a course of treatment for treating the presence or susceptibility of the pregnancy-related state of the subject. In some embodiments, the method further comprises stratifying the pre-term birth by using the trained algorithm to determine a molecular sub-type of the pre-term birth from among a plurality of distinct molecular subtypes of pre-term birth. In some embodiments, the plurality of distinct molecular subtypes of pre-term birth comprises a molecular subtype of pre-term birth selected from the group consisting of history of prior pre-term birth, spontaneous pre-term birth, ethnicity specific pre-term birth risk (e.g., among an African-American population), and pre-term premature rupture of membrane (PPROM).

In another aspect, the present disclosure provides a computer system for identifying or monitoring a presence or susceptibility of the pregnancy-related state of a subject, comprising: a database that is configured to store a first dataset and a second dataset, wherein the second dataset is indicative of the presence or susceptibility of the pregnancy-related state at a specificity greater than the first dataset; and one or more computer processors operatively coupled to the database, wherein the one or more computer processors are individually collectively programmed to: (i) use a trained algorithm to process at least the second dataset to determine the presence or susceptibility of the pregnancy-related state, which trained algorithm has an accuracy of at least about 70% over 50 independent samples; and (ii) electronically output a report indicative of the presence or susceptibility of the pregnancy-related state of the subject.

In some embodiments, the computer system further comprises an electronic display operatively coupled to the one or more computer processors, wherein the electronic display comprises a graphical user interface that is configured to display the report.

In another aspect, the present disclosure provides a non-transitory computer readable medium comprising machine-executable code that, upon execution by one or more computer processors, implements a method for identifying or monitoring a presence or susceptibility of the pregnancy-related state of a subject, the method comprising: (a) obtaining a first dataset, and a second dataset, wherein the second dataset is indicative of the presence or susceptibility of the pregnancy-related state at a specificity greater than the first dataset; (b) using a trained algorithm to process at least the second dataset to determine the pregnancy-related state, which trained algorithm has an accuracy of at least about 70% over 50 independent samples; and (c) electronically outputting a report indicative of the presence or susceptibility of the pregnancy-related state of the subject.

In another aspect, the present disclosure provides a method for identifying a presence or susceptibility of pregnancy-related state of a subject, comprising (i) assaying a first cell-free biological sample derived from the subject with a first assay to generate a first dataset, (ii) assaying a second cell-free biological sample derived from the subject with a second assay to generate a second dataset that is indicative of the presence or susceptibility of the pregnancy-related state at a specificity greater than the first dataset, and (iii) using a trained algorithm to process at least the second dataset to determine the presence or susceptibility of the pregnancy-related state at an accuracy of at least about 70%.

In some embodiments, the accuracy is at least about 80%. In some embodiments, the accuracy is at least about 90%. In some embodiments, the pregnancy-related state is selected from the group consisting of pre-term birth, full-term birth, gestational age, due date, onset of labor, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea), and fetal development stages or states (e.g., normal fetal organ function or development, and abnormal fetal organ function or development).

In another aspect, the present disclosure provides a method for determining that a subject is at risk of pre-term birth, comprising assaying a cell-free biological sample derived from the subject to generate a dataset that is indicative of the pre-term birth risk at a specificity of at least 80%, and using a trained algorithm that is trained on samples independent of the cell-free biological sample to determine that the subject is at risk of pre-term birth at an accuracy of at least about 70%. In some embodiments, the accuracy is at least about 80%. In some embodiments, the accuracy is at least about 90%.

In another aspect, the present disclosure provides a method for detecting a presence or risk of a prenatal metabolic genetic disease of a fetus of a pregnant subject, comprising: assaying ribonucleic acid (RNA) in a cell-free biological sample derived from said pregnant subject to detect a set of biomarkers; and analyzing said set of biomarkers with an algorithm (e.g., a trained algorithm) to detect said presence or risk of said prenatal metabolic genetic disease.

In another aspect, the present disclosure provides a method for detecting at least two health or physiological conditions of a fetus of a pregnant subject or of said pregnant subject, comprising: assaying a first cell-free biological sample obtained or derived from said pregnant subject at a first time point and a second cell-free biological sample obtained or derived from said pregnant subject at a second time point, to detect a first set of biomarkers at said first time point and a second set of biomarkers at said second time point, and analyzing said first set of biomarkers or said second set of biomarkers with a trained algorithm to detect said at least two health or physiological conditions.

In some embodiments, said at least two health or physiological conditions are selected from the group consisting of pre-term birth, full-term birth, gestational age, due date, onset of labor, a pregnancy-related hypertensive disorder, eclampsia, gestational diabetes, a congenital disorder of a fetus of said subject, ectopic pregnancy, spontaneous abortion, stillbirth, a post-partum complication, hyperemesis gravidarum, hemorrhage or excessive bleeding during delivery, premature rupture of membrane, premature rupture of membrane in pre-term birth, placenta previa, intrauterine/fetal growth restriction, macrosomia, a neonatal condition, and a fetal development stage or state. In some embodiments, said set of biomarkers comprises a genomic locus associated with due date, wherein said genomic locus is selected from the group consisting of genes listed in Table 1 and Table 7. In some embodiments, said set of biomarkers comprises a genomic locus associated with gestational age, wherein said genomic locus is selected from the group consisting of genes listed in Table 2. In some embodiments, said set of biomarkers comprises a genomic locus associated with pre-term birth, wherein said genomic locus is selected from the group consisting of genes listed in Table 5, genes listed in Table 6, genes listed in Table 8, RAB27B, RGS18, CLCN3, B3GNT2, COL24A1, CXCL8, and PTGS2. In some embodiments, said set of biomarkers comprises at least 5 distinct genomic loci.

In another aspect, the present disclosure provides a method comprising: assaying one or more cell-free biological samples obtained or derived from a pregnant subject to detect a set of biomarkers; and analyzing said set of biomarkers to identify (1) a due date or a range thereof of a fetus of said pregnant subject and (2) a health or physiological condition of said fetus of said pregnant subject or of said pregnant subject.

In some embodiments, the method further comprises analyzing said set of biomarkers with a trained algorithm. In some embodiments, said health or physiological condition is selected from the group consisting of pre-term birth, full-term birth, gestational age, due date, onset of labor, a pregnancy-related hypertensive disorder, eclampsia, gestational diabetes, a congenital disorder of a fetus of said subject, ectopic pregnancy, spontaneous abortion, stillbirth, a post-partum complication, hyperemesis gravidarum, hemorrhage or excessive bleeding during delivery, premature rupture of membrane, premature rupture of membrane in pre-term birth, placenta previa, intrauterine/fetal growth restriction, macrosomia, a neonatal condition, and a fetal development stage or state. In some embodiments, said set of biomarkers comprises a genomic locus associated with due date, wherein said genomic locus is selected from the group consisting of genes listed in Table 1 and Table 7. In some embodiments, said set of biomarkers comprises a genomic locus associated with gestational age, wherein said genomic locus is selected from the group consisting of genes listed in Table 2. In some embodiments, said set of biomarkers comprises a genomic locus associated with pre-term birth, wherein said genomic locus is selected from the group consisting of genes listed in Table 5, genes listed in Table 6, genes listed in Table 8, RAB27B, RGS18, CLCN3, B3GNT2, COL24A1, CXCL8, and PTGS2. In some embodiments, said set of biomarkers comprises at least 5 distinct genomic loci.

In another aspect, the present disclosure provides a method comprising: assaying one or more cell-free biological samples obtained or derived from a pregnant subject to detect a set of nucleic acids of non-human origin; and analyzing said set of nucleic acids of non-human origin to detect a health or physiological condition of a fetus of said pregnant subject or of said pregnant subject. In some embodiments, the nucleic acids of non-human origin comprise DNA or RNA of a non-human organism. In some embodiments, the non-human organism is a bacteria, a virus, or a parasite. In some embodiments, the method further comprises analyzing said set of nucleic acids of non-human origin using a trained algorithm.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 5E shows a summary of the predictive models for predicting due date, including a predictive model using samples with a time-to-delivery of less than 5 weeks and predictive model using samples with a time-to-delivery of less than 7.5 weeks; different predictive models were generated with estimated due date information (e.g., determined using estimated gestational age from ultrasound measurements) and without the estimated due date information.

FIG. 14B shows a combination of conditions which can be tested from a single blood draw along a pregnancy progression of a pregnant subject.

DETAILED DESCRIPTION

Figure 1:
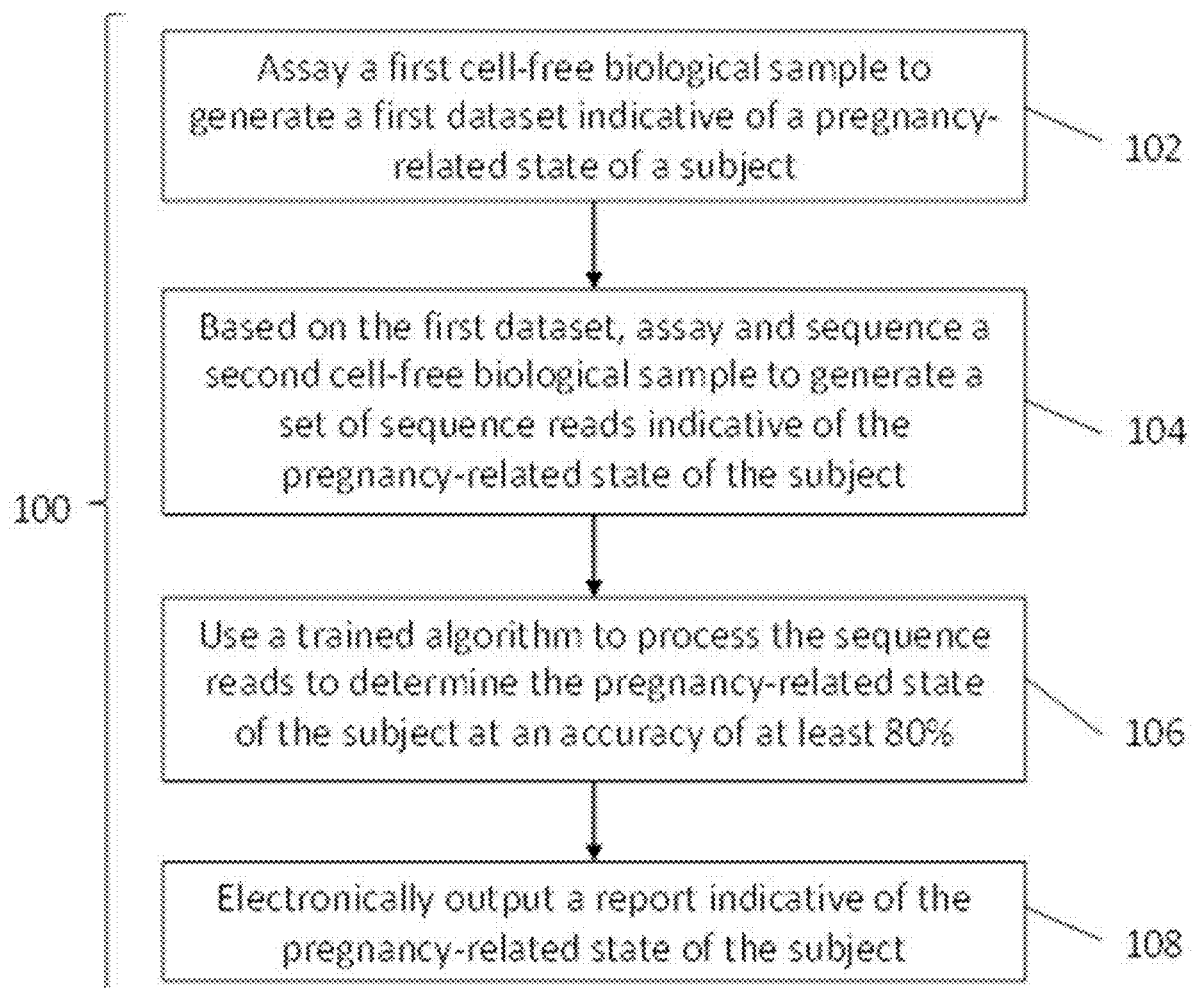
FIG. 1 illustrates an example workflow of a method for identifying or monitoring a pregnancy-related state of a subject, in accordance with disclosed embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an", and "the" include plural references unless the context clearly dictates otherwise. For example, the term "a nucleic acid" includes a plurality of nucleic acids, including mixtures thereof.

As used herein, the term "subject," generally refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets. A subject can be a pregnant female subject. The subject can be a woman having a fetus (or multiple fetuses) or suspected of having the fetus (or multiple fetuses). The subject can be a person that is pregnant or is suspected of being pregnant. The subject may be displaying a symptom(s) indicative of a health or physiological state or condition of the subject, such as a pregnancy-related health or physiological state or condition of the subject. As an alternative, the subject can be asymptomatic with respect to such health or physiological state or condition.

The term "pregnancy-related state," as used herein, generally refers to any health, physiological, and/or biochemical state or condition of a subject that is pregnant or is suspected of being pregnant, or of a fetus (or multiple fetuses) of the subject. Examples of pregnancy-related states include, without limitation, pre-term birth, full-term birth, gestational age, due date, onset of labor, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosus, periventricular leukomalacia, persistent pulmonary hypertension, polycythemia, respiratory distress syndrome, retinopathy of prematurity, and transient tachypnea), and fetal development stages or states (e.g., normal fetal organ function or development, and abnormal fetal organ function or development). In some situations, the pregnancy-related state is not associated with the health or physiological state or condition of a fetus (or multiple fetuses) of the subject.

As used herein, the term "sample," generally refers to a biological sample obtained from or derived from one or more subjects. Biological samples may be cell-free biological samples or substantially cell-free biological samples, or may be processed or fractionated to produce cell-free biological samples. For example, cell-free biological samples may include cell-free ribonucleic acid (cfRNA), cell-free deoxyribonucleic acid (cfDNA), cell-free fetal DNA (cffDNA), plasma, serum, urine, saliva, amniotic fluid, and derivatives thereof. Cell-free biological samples may be obtained or derived from subjects using an ethylenediaminetetraacetic acid (EDTA) collection tube, a cell-free RNA collection tube (e.g., Streck), or a cell-free DNA collection tube (e.g., Streck). Cell-free biological samples may be derived from whole blood samples by fractionation. Biological samples or derivatives thereof may contain cells. For example, a biological sample may be a blood sample or a derivative thereof (e.g., blood collected by a collection tube or blood drops), a vaginal sample (e.g., a vaginal swab), or a cervical sample (e.g., a cervical swab).

As used herein, the term "nucleic acid" generally refers to a polymeric form of nucleotides of any length, either deoxyribonucleotides (dNTPs) or ribonucleotides (rNTPs), or analogs thereof. Nucleic acids may have any three-dimensional structure, and may perform any function, known or unknown. Non-limiting examples of nucleic acids include deoxyribonucleic (DNA), ribonucleic acid (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), microRNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a reporter agent.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogs thereof. As used herein, a "target ribonucleic acid (RNA)" generally refers to a target nucleic acid that is RNA. As used herein, a "target deoxyribonucleic acid (DNA)" generally refers to a target nucleic acid that is DNA.

As used herein, the terms "amplifying" and "amplification" generally refer to increasing the size or quantity of a nucleic acid molecule. The nucleic acid molecule may be single-stranded or double-stranded. Amplification may include generating one or more copies or "amplified product" of the nucleic acid molecule. Amplification may be performed, for example, by extension (e.g., primer extension) or ligation. Amplification may include performing a primer extension reaction to generate a strand complementary to a single-stranded nucleic acid molecule, and in some cases generate one or more copies of the strand and/or the single-stranded nucleic acid molecule. The term "DNA amplification" generally refers to generating one or more copies of a DNA molecule or "amplified DNA product." The term "reverse transcription amplification" generally refers to the generation of deoxyribonucleic acid (DNA) from a ribonucleic acid (RNA) template via the action of a reverse transcriptase.

Every year, about 15 million pre-term births are reported globally. Pre-term birth may affect as many as about 10% of pregnancies, of which the majority are spontaneous pre-term births. Currently, there may be no meaningful, clinically actionable diagnostic screenings or tests available for many pregnancy-related complications such as pre-term birth. However, pregnancy-related complications such as pre-term birth are a leading cause of neonatal death and of complications later in life. Further, such pregnancy-related complications can cause negative health effects on maternal health. Thus, to make pregnancy as safe as possible, there exists a need for rapid, accurate methods for identifying and monitoring pregnancy-related states that are non-invasive and cost-effective, toward improving maternal and fetal health.

Current tests for prenatal care may be in inaccessible and incomplete. For cases in which pregnancies progress without pregnancy-related complications, limited methods of pregnancy monitoring may be available for a pregnancy subject, such as molecular tests, ultrasound imaging, and estimation of gestational age and/or due date using the last menstrual period. However, such monitoring methods may be complex, expensive, and unreliable. For example, molecular tests cannot predict gestational age, ultrasound imaging is expensive and best performed during the first trimester of pregnancy, and estimation of gestational age and/or due date using the last menstrual period can be unreliable. Further, for cases in which pregnancies progress with pregnancy-related complications such as risk of spontaneous pre-term delivery, the clinical utility of molecular tests, ultrasound imaging, and demographic factors may be limited. For example, molecular tests may have a limited BMI (body mass index) range, a limited gestational age and/or due date range (about 2 weeks), and a low positive predictive value (PPV); ultrasound imaging may be expensive and have low PPV and specificity; and the use of demographic factors to predict risk of pregnancy-related complications may be unreliable. Therefore, there exists an urgent clinical need for accurate and affordable non-invasive diagnostic methods for detection and monitoring of pregnancy-related states (e.g., estimation of gestational age, due date, and/or onset of labor, and prediction of pregnancy-related complications such as pre-term birth) toward clinically actionable outcomes.

The present disclosure provides methods, systems, and kits for identifying or monitoring pregnancy-related states by processing cell-free biological samples obtained from or derived from subjects (e.g., pregnancy female subjects). Cell-free biological samples (e.g., plasma samples) obtained from subjects may be analyzed to identify the pregnancy-related state (which may include, e.g., measuring a presence, absence, or quantitative assessment (e.g., risk) of the pregnancy-related state). Such subjects may include subjects with one or more pregnancy-related states and subjects without pregnancy-related states. Pregnancy-related states may include, for example, pre-term birth, full-term birth, gestational age, due date, onset of labor, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, and macrosomia (large fetus for gestational age). In some embodiments, pregnancy-related states are not associated with the health of a fetus. In some embodiments, pregnancy-related states include neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea) and fetal development stages or states (e.g., normal fetal organ function or development, and abnormal fetal organ function or development).

FIG. 1 illustrates an example workflow of a method for identifying or monitoring a pregnancy-related state of a subject, in accordance with disclosed embodiments. In an aspect, the present disclosure provides a method 100 for identifying or monitoring a pregnancy-related state of a subject. The method 100 may comprise using a first assay to process a first cell-free biological sample derived from said subject to generate a first dataset (as in operation 102). Next, based at least in part on the first dataset generated, the method 100 may optionally comprise using a second assay (e.g., different from the first assay) to process a second cell-free biological sample derived from the subject to generate a second dataset indicative of the pregnancy-related state at a specificity greater than the first dataset. For example, ribonucleic acid (RNA) molecules extracted from a second cell-free plasma sample may be sequenced to generate a set of sequence reads indicative of a pregnancy-related state of the subject (as in operation 104). In some embodiments, a first cell-free biological sample can be obtained from a subject at a first time point for processing with a first assay. Then, optionally a second cell-free biological sample can be obtained from the same subject at a second time point for processing with a second assay. In some embodiments, a cell-free biological sample can be obtained from a subject and then aliquoted to produce a first cell-free biological sample and a second cell-free biological sample, which are then processed with a first assay and a second assay, respectively. Next, a trained algorithm may be used to process the first dataset and/or the second dataset to determine the pregnancy-related state of the subject (as in operation 106). The trained algorithm may be configured to identify the pregnancy-related state at an accuracy of at least about 70% over 50 independent samples. In some embodiments, the accuracy is at least about 80%. In some embodiments, the accuracy is at least about 90%. A report may then be electronically outputted that is indicative of (e.g., identifies or provides an indication of) presence or susceptibility of the pregnancy-related state of the subject (as in operation 108).

Assaying Cell-Free Biological Samples

The cell-free biological samples may be obtained or derived from a human subject (e.g., a pregnant female subject). The cell-free biological samples may be stored in a variety of storage conditions before processing, such as different temperatures (e.g., at room temperature, under refrigeration or freezer conditions, at 25° C., at 4° C., at −18° C., −20° C., or at −80° C.) or different suspensions (e.g., EDTA collection tubes, cell-free RNA collection tubes, or cell-free DNA collection tubes).

The cell-free biological sample may be obtained from a subject with a pregnancy-related state (e.g., a pregnancy-related complication), from a subject that is suspected of having a pregnancy-related state (e.g., a pregnancy-related complication), or from a subject that does not have or is not suspected of having the pregnancy-related state (e.g., a pregnancy-related complication). The pregnancy-related state may comprise a pregnancy-related complication, such as pre-term birth, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea), and abnormal fetal development stages or states (e.g., abnormal fetal organ function or development). The pregnancy-related state may comprise a full-term birth, normal fetal development stages or states (e.g., normal fetal organ function or development), or absence of a pregnancy-related complication (e.g., pre-term birth, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea), and abnormal fetal development stages or states (e.g., abnormal fetal organ function or development)). The pregnancy-related state may comprise a quantitative assessment of pregnancy such as gestational age (e.g., measured in days, weeks or months) or due date (e.g., expressed as a predicted or estimated calendar date or range of calendar dates). The pregnancy-related state may comprise a quantitative assessment of a pregnancy-related complication such as a likelihood, a susceptibility, or a risk (e.g., expressed as a probability, a relative probability, an odds ratio, or a risk score or risk index) of the pregnancy-related complication (e.g., pre-term birth, onset of labor, pregnancy-related hypertensive disorders (e.g., preeclampsia), eclampsia, gestational diabetes, a congenital disorder of a fetus of the subject, ectopic pregnancy, spontaneous abortion, stillbirth, post-partum complications (e.g., post-partum depression, hemorrhage or excessive bleeding, pulmonary embolism, cardiomyopathy, diabetes, anemia, and hypertensive disorders), hyperemesis gravidarum (morning sickness), hemorrhage or excessive bleeding during delivery, premature rupture of membrane, premature rupture of membrane in pre-term birth, placenta previa (placenta covering the cervix), intrauterine/fetal growth restriction, macrosomia (large fetus for gestational age), neonatal conditions (e.g., anemia, apnea, bradycardia and other heart defects, bronchopulmonary dysplasia or chronic lung disease, diabetes, gastroschisis, hydrocephaly, hyperbilirubinemia, hypocalcemia, hypoglycemia, intraventricular hemorrhage, jaundice, necrotizing enterocolitis, patent ductus arteriosis, periventricular leukomalacia, persistent pulmonary hypertension, polycythemia, respiratory distress syndrome, retinopathy of prematurity, and transient tachypnea), and abnormal fetal development stages or states (e.g., abnormal fetal organ function or development)). For example, the pregnancy-related state may comprise a likelihood or susceptibility of an onset of labor in the future (e.g., within about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1.5 days, about 2 days, about 2.5 days, about 3 days, about 3.5 days, about 4 days, about 4.5 days, about 5 days, about 5.5 days, about 6 days, about 6.5 days, about 7 days, about 8 days, about 9 days, about 10 days, about 12 days, about 14 days, about 3 weeks, about 4 weeks, about 5 weeks, about 6 weeks, about 7 weeks, about 8 weeks, about 9 weeks, about 10 weeks, about 11 weeks, about 12 weeks, about 13 weeks, or more than about 13 weeks).

The cell-free biological sample may be taken before and/or after treatment of a subject with the pregnancy-related complication. Cell-free biological samples may be obtained from a subject during a treatment or a treatment regime. Multiple cell-free biological samples may be obtained from a subject to monitor the effects of the treatment over time. The cell-free biological sample may be taken from a subject known or suspected of having a pregnancy-related state (e.g., pregnancy-related complication) for which a definitive positive or negative diagnosis is not available via clinical tests. The sample may be taken from a subject suspected of having a pregnancy-related complication. The cell-free biological sample may be taken from a subject experiencing unexplained symptoms, such as fatigue, nausea, weight loss, aches and pains, weakness, or bleeding. The cell-free biological sample may be taken from a subject having explained symptoms. The cell-free biological sample may be taken from a subject at risk of developing a pregnancy-related complication due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

The cell-free biological sample may contain one or more analytes capable of being assayed, such as cell-free ribonucleic acid (cfRNA) molecules suitable for assaying to generate transcriptomic data, cell-free deoxyribonucleic acid (cfDNA) molecules suitable for assaying to generate genomic data, proteins suitable for assaying to generate proteomic data, metabolites suitable for assaying to generate metabolomic data, or a mixture or combination thereof. One or more such analytes (e.g., cfRNA molecules, cfDNA molecules, proteins, or metabolites) may be isolated or extracted from one or more cell-free biological samples of a subject for downstream assaying using one or more suitable assays.

After obtaining a cell-free biological sample from the subject, the cell-free biological sample may be processed to generate datasets indicative of a pregnancy-related state of the subject. For example, a presence, absence, or quantitative assessment of nucleic acid molecules of the cell-free biological sample at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites may be indicative of a pregnancy-related state. Processing the cell-free biological sample obtained from the subject may comprise (i) subjecting the cell-free biological sample to conditions that are sufficient to isolate, enrich, or extract a plurality of nucleic acid molecules, proteins, and/or metabolites, and (ii) assaying the plurality of nucleic acid molecules, proteins, and/or metabolites to generate the dataset.

In some embodiments, a plurality of nucleic acid molecules is extracted from the cell-free biological sample and subjected to sequencing to generate a plurality of sequencing reads. The nucleic acid molecules may comprise ribonucleic acid (RNA) or deoxyribonucleic acid (DNA). The nucleic acid molecules (e.g., RNA or DNA) may be extracted from the cell-free biological sample by a variety of methods, such as a FastDNA Kit protocol from MP Biomedicals, a QIAamp DNA cell-free biological mini kit from Qiagen, or a cell-free biological DNA isolation kit protocol from Norgen Biotek. The extraction method may extract all RNA or DNA molecules from a sample. Alternatively, the extract method may selectively extract a portion of RNA or DNA molecules from a sample. Extracted RNA molecules from a sample may be converted to DNA molecules by reverse transcription (RT).

The sequencing may be performed by any suitable sequencing methods, such as massively parallel sequencing (MPS), paired-end sequencing, high-throughput sequencing, next-generation sequencing (NGS), shotgun sequencing, single-molecule sequencing, nanopore sequencing, semi-conductor sequencing, pyrosequencing, sequencing-by-synthesis (SBS), sequencing-by-ligation, sequencing-by-hybridization, and RNA-Seq (Illumina).

The sequencing may comprise nucleic acid amplification (e.g., of RNA or DNA molecules). In some embodiments, the nucleic acid amplification is polymerase chain reaction (PCR). A suitable number of rounds of PCR (e.g., PCR, qPCR, reverse-transcriptase PCR, digital PCR, etc.) may be performed to sufficiently amplify an initial amount of nucleic acid (e.g., RNA or DNA) to a desired input quantity for subsequent sequencing. In some cases, the PCR may be used for global amplification of target nucleic acids. This may comprise using adapter sequences that may be first ligated to different molecules followed by PCR amplification using universal primers. PCR may be performed using any of a number of commercial kits, e.g., provided by Life Technologies, Affymetrix, Promega, Qiagen, etc. In other cases, only certain target nucleic acids within a population of nucleic acids may be amplified. Specific primers, possibly in conjunction with adapter ligation, may be used to selectively amplify certain targets for downstream sequencing. The PCR may comprise targeted amplification of one or more genomic loci, such as genomic loci associated with pregnancy-related states. The sequencing may comprise use of simultaneous reverse transcription (RT) and polymerase chain reaction (PCR), such as a OneStep RT-PCR kit protocol by Qiagen, NEB, Thermo Fisher Scientific, or Bio-Rad.

RNA or DNA molecules isolated or extracted from a cell-free biological sample may be tagged, e.g., with identifiable tags, to allow for multiplexing of a plurality of samples. Any number of RNA or DNA samples may be multiplexed. For example a multiplexed reaction may contain RNA or DNA from at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 initial cell-free biological samples. For example, a plurality of cell-free biological samples may be tagged with sample barcodes such that each DNA molecule may be traced back to the sample (and the subject) from which the DNA molecule originated. Such tags may be attached to RNA or DNA molecules by ligation or by PCR amplification with primers.

After subjecting the nucleic acid molecules to sequencing, suitable bioinformatics processes may be performed on the sequence reads to generate the data indicative of the presence, absence, or relative assessment of the pregnancy-related state. For example, the sequence reads may be aligned to one or more reference genomes (e.g., a genome of one or more species such as a human genome). The aligned sequence reads may be quantified at one or more genomic loci to generate the datasets indicative of the pregnancy-related state. For example, quantification of sequences corresponding to a plurality of genomic loci associated with pregnancy-related states may generate the datasets indicative of the pregnancy-related state.

The cell-free biological sample may be processed without any nucleic acid extraction. For example, the pregnancy-related state may be identified or monitored in the subject by using probes configured to selectively enrich nucleic acid (e.g., RNA or DNA) molecules corresponding to the plurality of pregnancy-related state-associated genomic loci. The probes may be nucleic acid primers. The probes may have sequence complementarity with nucleic acid sequences from one or more of the plurality of pregnancy-related state-associated genomic loci or genomic regions. The plurality of pregnancy-related state-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more distinct pregnancy-related state-associated genomic loci or genomic regions. The plurality of pregnancy-related state-associated genomic loci or genomic regions may comprise one or more members (e.g., 1, 2, 3, 4, 5, 6, 7, 8, 9, 10, 11, 12, 13, 14, 15, 16, 17, 18, 19, 20, about 25, about 30, about 35, about 40, about 45, about 50, about 55, about 60, about 65, about 70, about 75, about 80, or more) selected from the group consisting of ACTB, ADAM12, ALPP, ANXA3, APLF, ARG1, AVPR1A, CAMP, CAPN6, CD180, CGA, CGB, CLCN3, CPVL, CSH1, CSH2, CSHL1, CYP3A7, DAPP1, DCX, DEFA4, DGCR14, ELANE, ENAH, EPB42, FABP1, FAM212B-AS1, FGA, FGB, FRMD4B, FRZB, FSTL3, GH2, GNAZ, HAL, HSD17B1, HSD3B1, HSPB8, Immune, ITIH2, KLF9, KNG1, KRT8, LGALS14, LTF, LYPLAL1, MAP3K7CL, MEF2C, MMD, MMP8, MOB1B, NFATC2, OTC, P2RY12, PAPPA, PGLYRP1, PKHD1L1, PKHD1L1, PLAC1, PLAC4, POLE2, PPBP, PSG1, PSG4, PSG7, PTGER3, RAB11A, RAB27B, RAP1GAP, RGS18, RPL23AP7, S100A8, S100A9, S100P, SERPINA7, SLC2A2, SLC38A4, SLC4A1, TBC1D15, VCAN, VGLL1, B3GNT2, COL24A1, CXCL8, and PTGS2. The pregnancy-related state-associated genomic loci or genomic regions may be associated with gestational age, pre-term birth, due date, onset of labor, or other pregnancy-related states or complications, such as the genomic loci described by, for example, Ngo et al. ("Noninvasive blood tests for fetal development predict gestational age and preterm delivery," *Science*, 360(6393), pp. 1133-1136, 8 Jun. 2018), which is hereby incorporated by reference in its entirety.

The probes may be nucleic acid molecules (e.g., RNA or DNA) having sequence complementarity with nucleic acid sequences (e.g., RNA or DNA) of the one or more genomic loci (e.g., pregnancy-related state-associated genomic loci). These nucleic acid molecules may be primers or enrichment sequences. The assaying of the cell-free biological sample using probes that are selective for the one or more genomic loci (e.g., pregnancy-related state-associated genomic loci) may comprise use of array hybridization (e.g., microarray-based), polymerase chain reaction (PCR), or nucleic acid sequencing (e.g., RNA sequencing or DNA sequencing). In some embodiments, DNA or RNA may be assayed by one or more of: isothermal DNA/RNA amplification methods (e.g., loop-mediated isothermal amplification (LAMP), helicase dependent amplification (HDA), rolling circle amplification (RCA), recombinase polymerase amplification (RPA)), immunoassays, electrochemical assays, surface-enhanced Raman spectroscopy (SERS), quantum dot (QD)-based assays, molecular inversion probes, droplet digital PCR (ddPCR), CRISPR/Cas-based detection (e.g., CRISPR-typing PCR (ctPCR), specific high-sensitivity enzymatic reporter un-locking (SHERLOCK), DNA endonuclease targeted CRISPR trans reporter (DETECTR), and CRISPR-mediated analog multi-event recording apparatus (CAMERA)), and laser transmission spectroscopy (LTS).

The assay readouts may be quantified at one or more genomic loci (e.g., pregnancy-related state-associated genomic loci) to generate the data indicative of the pregnancy-related state. For example, quantification of array hybridization or polymerase chain reaction (PCR) corresponding to a plurality of genomic loci (e.g., pregnancy-related state-associated genomic loci) may generate data indicative of the pregnancy-related state. Assay readouts may comprise quantitative PCR (qPCR) values, digital PCR (dPCR) values, digital droplet PCR (ddPCR) values, fluorescence values, etc., or normalized values thereof. The assay may be a home use test configured to be performed in a home setting.

In some embodiments, multiple assays are used to process cell-free biological samples of a subject. For example, a first assay may be used to process a first cell-free biological sample obtained or derived from the subject to generate a first dataset; and based at least in part on the first dataset, a second assay different from said first assay may be used to process a second cell-free biological sample obtained or derived from the subject to generate a second dataset indicative of said pregnancy-related state. The first assay may be used to screen or process cell-free biological samples of a set of subjects, while the second or subsequent assays may be used to screen or process cell-free biological samples of a smaller subset of the set of subjects. The first assay may have a low cost and/or a high sensitivity of detecting one or more pregnancy-related states (e.g., pregnancy-related complication), that is amenable to screening or processing cell-free biological samples of a relatively large set of subjects. The second assay may have a higher cost and/or a higher specificity of detecting one or more pregnancy-related states (e.g., pregnancy-related complication), that is amenable to screening or processing cell-free biological samples of a relatively small set of subjects (e.g., a subset of the subjects screened using the first assay). The second assay may generate a second dataset having a specificity (e.g., for one or more pregnancy-related states such as pregnancy-related complications) greater than the first dataset generated using the first assay. As an example, one or more cell-free biological samples may be processed using a cfRNA assay on a large set of subjects and subsequently a metabolomics assay on a smaller subset of subjects, or vice versa. The smaller subset of subjects may be selected based at least in part on the results of the first assay.

Alternatively, multiple assays may be used to simultaneously process cell-free biological samples of a subject. For example, a first assay may be used to process a first cell-free biological sample obtained or derived from the subject to generate a first dataset indicative of the pregnancy-related state; and a second assay different from the first assay may be used to process a second cell-free biological sample obtained or derived from the subject to generate a second dataset indicative of the pregnancy-related state. Any or all of the first dataset and the second dataset may then be analyzed to assess the pregnancy-related state of the subject. For example, a single diagnostic index or diagnosis score can be generated based on a combination of the first dataset and the second dataset. As another example, separate diagnostic indexes or diagnosis scores can be generated based on the first dataset and the second dataset.

The cell-free biological samples may be processed using a metabolomics assay. For example, a metabolomics assay can be used to identify a quantitative measure (e.g., indicative of a presence, absence, or relative amount) of each of a plurality of pregnancy-related state-associated metabolites in a cell-free biological sample of the subject. The metabolomics assay may be configured to process cell-free biological samples such as a blood sample or a urine sample (or derivatives thereof) of the subject. A quantitative measure (e.g., indicative of a presence, absence, or relative amount) of pregnancy-related state-associated metabolites in the cell-free biological sample may be indicative of one or more pregnancy-related states. The metabolites in the cell-free biological sample may be produced (e.g., as an end product or a byproduct) as a result of one or more metabolic pathways corresponding to pregnancy-related state-associated genes. Assaying one or more metabolites of the cell-free biological sample may comprise isolating or extracting the metabolites from the cell-free biological sample. The metabolomics assay may be used to generate datasets indicative of the quantitative measure (e.g., indicative of a presence, absence, or relative amount) of each of a plurality of pregnancy-related state-associated metabolites in the cell-free biological sample of the subject.

The metabolomics assay may analyze a variety of metabolites in the cell-free biological sample, such as small molecules, lipids, amino acids, peptides, nucleotides, hormones and other signaling molecules, cytokines, minerals and elements, polyphenols, fatty acids, dicarboxylic acids, alcohols and polyols, alkanes and alkenes, keto acids, glycolipids, carbohydrates, hydroxy acids, purines, prostanoids, catecholamines, acyl phosphates, phospholipids, cyclic amines, amino ketones, nucleosides, glycerolipids, aromatic acids, retinoids, amino alcohols, pterins, steroids, carnitines, leukotrienes, indoles, porphyrins, sugar phosphates, coenzyme A derivatives, glucuronides, ketones, sugar phosphates, inorganic ions and gases, sphingolipids, bile acids, alcohol phosphates, amino acid phosphates, aldehydes, quinones, pyrimidines, pyridoxals, tricarboxylic acids, acyl glycines, cobalamin derivatives, lipoamides, biotin, and polyamines.

The metabolomics assay may comprise, for example, one or more of: mass spectroscopy (MS), targeted MS, gas chromatography (GC), high performance liquid chromatography (HPLC), capillary electrophoresis (CE), nuclear magnetic resonance (NMR) spectroscopy, ion-mobility spectrometry, Raman spectroscopy, electrochemical assay, or immune assay.

The cell-free biological samples may be processed using a methylation-specific assay. For example, a methylation-specific assay can be used to identify a quantitative measure (e.g., indicative of a presence, absence, or relative amount) of methylation each of a plurality of pregnancy-related state-associated genomic loci in a cell-free biological sample of the subject. The methylation-specific assay may be configured to process cell-free biological samples such as a blood sample or a urine sample (or derivatives thereof) of the subject. A quantitative measure (e.g., indicative of a presence, absence, or relative amount) of methylation of pregnancy-related state-associated genomic loci in the cell-free biological sample may be indicative of one or more pregnancy-related states. The methylation-specific assay may be used to generate datasets indicative of the quantitative measure (e.g., indicative of a presence, absence, or relative amount) of methylation of each of a plurality of pregnancy-related state-associated genomic loci in the cell-free biological sample of the subject.

The methylation-specific assay may comprise, for example, one or more of: a methylation-aware sequencing (e.g., using bisulfate treatment), pyrosequencing, methylation-sensitive single-strand conformation analysis (MS-SSCA), high-resolution melting analysis (HRM), methylation-sensitive single-nucleotide primer extension (MS-SnuPE), base-specific cleavage/MALDI-TOF, microarray-based methylation assay, methylation-specific PCR, targeted bisulfite sequencing, oxidative bisulfite sequencing, mass spectroscopy-based bisulfite sequencing, or reduced representation bisulfite sequence (RRBS).

The cell-free biological samples may be processed using a proteomics assay. For example, a proteomics assay can be used to identify a quantitative measure (e.g., indicative of a presence, absence, or relative amount) of each of a plurality of pregnancy-related state-associated proteins or polypeptides in a cell-free biological sample of the subject. The proteomics assay may be configured to process cell-free biological samples such as a blood sample or a urine sample (or derivatives thereof) of the subject. A quantitative measure (e.g., indicative of a presence, absence, or relative amount) of pregnancy-related state-associated proteins or polypeptides in the cell-free biological sample may be indicative of one or more pregnancy-related states. The proteins or polypeptides in the cell-free biological sample may be produced (e.g., as an end product or a byproduct) as a result of one or more biochemical pathways corresponding to pregnancy-related state-associated genes. Assaying one or more proteins or polypeptides of the cell-free biological sample may comprise isolating or extracting the proteins or polypeptides from the cell-free biological sample. The proteomics assay may be used to generate datasets indicative of the quantitative measure (e.g., indicative of a presence, absence, or relative amount) of each of a plurality of pregnancy-related state-associated proteins or polypeptides in the cell-free biological sample of the subject.

The proteomics assay may analyze a variety of proteins or polypeptides in the cell-free biological sample, such as proteins made under different cellular conditions (e.g., development, cellular differentiation, or cell cycle). The proteomics assay may comprise, for example, one or more of: an antibody-based immunoassay, an Edman degradation assay, a mass spectrometry-based assay (e.g., matrix-assisted laser desorption/ionization (MALDI) and electrospray ionization (ESI)), a top-down proteomics assay, a bottom-up proteomics assay, a mass spectrometric immunoassay (MSIA), a stable isotope standard capture with anti-peptide antibodies (SISCAPA) assay, a fluorescence two-dimensional differential gel electrophoresis (2-D DIGE) assay, a quantitative proteomics assay, a protein microarray assay, or a reverse-phased protein microarray assay. The proteomics assay may detect post-translational modifications of proteins or polypeptides (e.g., phosphorylation, ubiquitination, methylation, acetylation, glycosylation, oxidation, and nitrosylation). The proteomics assay may identify or quantify one or more proteins or polypeptides from a database (e.g., Human Protein Atlas, PeptideAtlas, and UniProt).

Kits

The present disclosure provides kits for identifying or monitoring a pregnancy-related state of a subject. A kit may comprise probes for identifying a quantitative measure (e.g., indicative of a presence, absence, or relative amount) of sequences at each of a plurality of pregnancy-related state-associated genomic loci in a cell-free biological sample of the subject. A quantitative measure (e.g., indicative of a presence, absence, or relative amount) of sequences at each of a plurality of pregnancy-related state-associated genomic loci in the cell-free biological sample may be indicative of one or more pregnancy-related states. The probes may be selective for the sequences at the plurality of pregnancy-related state-associated genomic loci in the cell-free biological sample. A kit may comprise instructions for using the probes to process the cell-free biological sample to generate datasets indicative of a quantitative measure (e.g., indicative of a presence, absence, or relative amount) of sequences at each of the plurality of pregnancy-related state-associated genomic loci in a cell-free biological sample of the subject.

The probes in the kit may be selective for the sequences at the plurality of pregnancy-related state-associated genomic loci in the cell-free biological sample. The probes in the kit may be configured to selectively enrich nucleic acid (e.g., RNA or DNA) molecules corresponding to the plurality of pregnancy-related state-associated genomic loci. The probes in the kit may be nucleic acid primers. The probes in the kit may have sequence complementarity with nucleic acid sequences from one or more of the plurality of pregnancy-related state-associated genomic loci or genomic regions. The plurality of pregnancy-related state-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more distinct pregnancy-related state-associated genomic loci or genomic regions. The plurality of pregnancy-related state-associated genomic loci or genomic regions may comprise one or more members selected from the group consisting of ACTB, ADAM12, ALPP, ANXA3, APLF, ARG1, AVPR1A, CAMP, CAPN6, CD180, CGA, CGB, CLCN3, CPVL, CSH1, CSH2, CSHL1, CYP3A7, DAPP1, DCX, DEFA4, DGCR14, ELANE, ENAH, EPB42, FABP1, FAM212B-AS1, FGA, FGB, FRMD4B, FRZB, FSTL3, GH2, GNAZ, HAL, HSD17B1, HSD3B1, HSPB8, Immune, ITIH2, KLF9, KNG1, KRT8, LGALS14, LTF, LYPLAL1, MAP3K7CL, MEF2C, MMD, MMP8, MOB1B, NFATC2, OTC, P2RY12, PAPPA, PGLYRP1, PKHD1L1, PKHD1L1, PLAC1, PLAC4, POLE2, PPBP, PSG1, PSG4, PSG7, PTGER3, RAB11A, RAB27B, RAP1GAP, RGS18, RPL23AP7, S100A8, S100A9, S100P, SERPINA7, SLC2A2, SLC38A4, SLC4A1, TBC1D15, VCAN, VGLL1, B3GNT2, COL24A1, CXCL8, and PTGS2.

The instructions in the kit may comprise instructions to assay the cell-free biological sample using the probes that are selective for the sequences at the plurality of pregnancy-related state-associated genomic loci in the cell-free biological sample. These probes may be nucleic acid molecules (e.g., RNA or DNA) having sequence complementarity with nucleic acid sequences (e.g., RNA or DNA) from one or more of the plurality of pregnancy-related state-associated genomic loci. These nucleic acid molecules may be primers or enrichment sequences. The instructions to assay the cell-free biological sample may comprise introductions to perform array hybridization, polymerase chain reaction (PCR), or nucleic acid sequencing (e.g., DNA sequencing or RNA sequencing) to process the cell-free biological sample to generate datasets indicative of a quantitative measure (e.g., indicative of a presence, absence, or relative amount) of sequences at each of the plurality of pregnancy-related state-associated genomic loci in the cell-free biological sample. A quantitative measure (e.g., indicative of a presence, absence, or relative amount) of sequences at each of a plurality of pregnancy-related state-associated genomic loci in the cell-free biological sample may be indicative of one or more pregnancy-related states.

The instructions in the kit may comprise instructions to measure and interpret assay readouts, which may be quantified at one or more of the plurality of pregnancy-related state-associated genomic loci to generate the datasets indicative of a quantitative measure (e.g., indicative of a presence, absence, or relative amount) of sequences at each of the plurality of pregnancy-related state-associated genomic loci in the cell-free biological sample. For example, quantification of array hybridization or polymerase chain reaction (PCR) corresponding to the plurality of pregnancy-related state-associated genomic loci may generate the datasets indicative of a quantitative measure (e.g., indicative of a presence, absence, or relative amount) of sequences at each of the plurality of pregnancy-related state-associated genomic loci in the cell-free biological sample. Assay readouts may comprise quantitative PCR (qPCR) values, digital PCR (dPCR) values, digital droplet PCR (ddPCR) values, fluorescence values, etc., or normalized values thereof.

A kit may comprise a metabolomics assay for identifying a quantitative measure (e.g., indicative of a presence, absence, or relative amount) of each of a plurality of pregnancy-related state-associated metabolites in a cell-free biological sample of the subject. A quantitative measure (e.g., indicative of a presence, absence, or relative amount) of pregnancy-related state-associated metabolites in the cell-free biological sample may be indicative of one or more pregnancy-related states. The metabolites in the cell-free biological sample may be produced (e.g., as an end product or a byproduct) as a result of one or more metabolic pathways corresponding to pregnancy-related state-associated genes. A kit may comprise instructions for isolating or extracting the metabolites from the cell-free biological sample and/or for using the metabolomics assay to generate datasets indicative of the quantitative measure (e.g., indicative of a presence, absence, or relative amount) of each of a plurality of pregnancy-related state-associated metabolites in the cell-free biological sample of the subject.

Trained Algorithms

After using one or more assays to process one or more cell-free biological samples derived from the subject to generate one or more datasets indicative of the pregnancy-related state or pregnancy-related complication, a trained algorithm may be used to process one or more of the datasets (e.g., at each of a plurality of pregnancy-related state-associated genomic loci) to determine the pregnancy-related state. For example, the trained algorithm may be used to determine quantitative measures of sequences at each of the plurality of pregnancy-related state-associated genomic loci in the cell-free biological samples. The trained algorithm may be configured to identify the pregnancy-related state with an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99% for at least about 25, at least about 50, at least about 100, at least about 150, at least about 200, at least about 250, at least about 300, at least about 350, at least about 400, at least about 450, at least about 500, or more than about 500 independent samples.

The trained algorithm may comprise a supervised machine learning algorithm. The trained algorithm may comprise a classification and regression tree (CART) algorithm. The supervised machine learning algorithm may comprise, for example, a Random Forest, a support vector machine (SVM), a neural network, or a deep learning algorithm. The trained algorithm may comprise an unsupervised machine learning algorithm.

The trained algorithm may be configured to accept a plurality of input variables and to produce one or more output values based on the plurality of input variables. The plurality of input variables may comprise one or more datasets indicative of a pregnancy-related state. For example, an input variable may comprise a number of sequences corresponding to or aligning to each of the plurality of pregnancy-related state-associated genomic loci. The plurality of input variables may also include clinical health data of a subject.

The trained algorithm may comprise a classifier, such that each of the one or more output values comprises one of a fixed number of possible values (e.g., a linear classifier, a logistic regression classifier, etc.) indicating a classification of the cell-free biological sample by the classifier. The trained algorithm may comprise a binary classifier, such that each of the one or more output values comprises one of two values (e.g., {0, 1}, {positive, negative}, or {high-risk, low-risk}) indicating a classification of the cell-free biological sample by the classifier. The trained algorithm may be another type of classifier, such that each of the one or more output values comprises one of more than two values (e.g., {0, 1, 2}, {positive, negative, or indeterminate}, or {high-risk, intermediate-risk, or low-risk}) indicating a classification of the cell-free biological sample by the classifier. The output values may comprise descriptive labels, numerical values, or a combination thereof. Some of the output values may comprise descriptive labels. Such descriptive labels may provide an identification or indication of the disease or disorder state of the subject, and may comprise, for example, positive, negative, high-risk, intermediate-risk, low-risk, or indeterminate. Such descriptive labels may provide an identification of a treatment for the subject's pregnancy-related state, and may comprise, for example, a therapeutic intervention, a duration of the therapeutic intervention, and/or a dosage of the therapeutic intervention suitable to treat a pregnancy-related condition. Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof. For example, such descriptive labels may provide a prognosis of the pregnancy-related state of the subject. As another example, such descriptive labels may provide a relative assessment of the pregnancy-related state (e.g., an estimated gestational age in number of days, weeks, or months) of the subject. Some descriptive labels may be mapped to numerical values, for example, by mapping "positive" to 1 and "negative" to 0.

Some of the output values may comprise numerical values, such as binary, integer, or continuous values. Such binary output values may comprise, for example, {0, 1}, {positive, negative}, or {high-risk, low-risk}. Such integer output values may comprise, for example, {0, 1, 2}. Such continuous output values may comprise, for example, a probability value of at least 0 and no more than 1. Such continuous output values may comprise, for example, an un-normalized probability value of at least 0. Such continuous output values may indicate a prognosis of the pregnancy-related state of the subject. Some numerical values may be mapped to descriptive labels, for example, by mapping 1 to "positive" and 0 to "negative."

Some of the output values may be assigned based on one or more cutoff values. For example, a binary classification of samples may assign an output value of "positive" or 1 if the sample indicates that the subject has at least a 50% probability of having a pregnancy-related state (e.g., pregnancy-related complication). For example, a binary classification of samples may assign an output value of "negative" or 0 if the sample indicates that the subject has less than a 50% probability of having a pregnancy-related state (e.g., pregnancy-related complication). In this case, a single cutoff value of 50% is used to classify samples into one of the two possible binary output values. Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, a classification of samples may assign an output value of "positive" or 1 if the sample indicates that the subject has a probability of having a pregnancy-related state (e.g., pregnancy-related complication) of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of samples may assign an output value of "positive" or 1 if the sample indicates that the subject has a probability of having a pregnancy-related state (e.g., pregnancy-related complication) of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classification of samples may assign an output value of "negative" or 0 if the sample indicates that the subject has a probability of having a pregnancy-related state (e.g., pregnancy-related complication) of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of samples may assign an output value of "negative" or 0 if the sample indicates that the subject has a probability of having a pregnancy-related state (e.g., pregnancy-related complication) of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classification of samples may assign an output value of "indeterminate" or 2 if the sample is not classified as "positive", "negative", 1, or 0. In this case, a set of two cutoff values is used to classify samples into one of the three possible output values. Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify samples into one of n+1 possible output values, where n is any positive integer.

The trained algorithm may be trained with a plurality of independent training samples. Each of the independent training samples may comprise a cell-free biological sample from a subject, associated datasets obtained by assaying the cell-free biological sample (as described elsewhere herein), and one or more known output values corresponding to the cell-free biological sample (e.g., a clinical diagnosis, prognosis, absence, or treatment efficacy of a pregnancy-related state of the subject). Independent training samples may comprise cell-free biological samples and associated datasets and outputs obtained or derived from a plurality of different subjects. Independent training samples may comprise cell-free biological samples and associated datasets and outputs obtained at a plurality of different time points from the same subject (e.g., on a regular basis such as weekly, biweekly, or monthly). Independent training samples may be associated with presence of the pregnancy-related state (e.g., training samples comprising cell-free biological samples and associated datasets and outputs obtained or derived from a plurality of subjects known to have the pregnancy-related state). Independent training samples may be associated with absence of the pregnancy-related state (e.g., training samples comprising cell-free biological samples and associated datasets and outputs obtained or derived from a plurality of subjects who are known to not have a previous diagnosis of the pregnancy-related state or who have received a negative test result for the pregnancy-related state).

The trained algorithm may be trained with at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The independent training samples may comprise cell-free biological samples associated with presence of the pregnancy-related state and/or cell-free biological samples associated with absence of the pregnancy-related state. The trained algorithm may be trained with no more than about 500, no more than about 450, no more than about 400, no more than about 350, no more than about 300, no more than about 250, no more than about 200, no more than about 150, no more than about 100, or no more than about 50 independent training samples associated with presence of the pregnancy-related state. In some embodiments, the cell-free biological sample is independent of samples used to train the trained algorithm.

The trained algorithm may be trained with a first number of independent training samples associated with presence of the pregnancy-related state and a second number of independent training samples associated with absence of the pregnancy-related state. The first number of independent training samples associated with presence of the pregnancy-related state may be no more than the second number of independent training samples associated with absence of the pregnancy-related state. The first number of independent training samples associated with presence of the pregnancy-related state may be equal to the second number of independent training samples associated with absence of the pregnancy-related state. The first number of independent training samples associated with presence of the pregnancy-related state may be greater than the second number of independent training samples associated with absence of the pregnancy-related state.

The trained algorithm may be configured to identify the pregnancy-related state at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The accuracy of identifying the pregnancy-related state by the trained algorithm may be calculated as the percentage of independent test samples (e.g., subjects known to have the pregnancy-related state or subjects with negative clinical test results for the pregnancy-related state) that are correctly identified or classified as having or not having the pregnancy-related state.

The trained algorithm may be configured to identify the pregnancy-related state with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the pregnancy-related state using the trained algorithm may be calculated as the percentage of cell-free biological samples identified or classified as having the pregnancy-related state that correspond to subjects that truly have the pregnancy-related state.

The trained algorithm may be configured to identify the pregnancy-related state with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the pregnancy-related state using the trained algorithm may be calculated as the percentage of cell-free biological samples identified or classified as not having the pregnancy-related state that correspond to subjects that truly do not have the pregnancy-related state.

The trained algorithm may be configured to identify the pregnancy-related state with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the pregnancy-related state using the trained algorithm may be calculated as the percentage of independent test samples associated with presence of the pregnancy-related state (e.g., subjects known to have the pregnancy-related state) that are correctly identified or classified as having the pregnancy-related state.

The trained algorithm may be configured to identify the pregnancy-related state with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the pregnancy-related state using the trained algorithm may be calculated as the percentage of independent test samples associated with absence of the pregnancy-related state (e.g., subjects with negative clinical test results for the pregnancy-related state) that are correctly identified or classified as not having the pregnancy-related state.

The trained algorithm may be configured to identify the pregnancy-related state with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operator Characteristic (ROC) curve (e.g., the area under the ROC curve) associated with the trained algorithm in classifying cell-free biological samples as having or not having the pregnancy-related state.

The trained algorithm may be adjusted or tuned to improve one or more of the performance, accuracy, PPV, NPV, clinical sensitivity, clinical specificity, or AUC of identifying the pregnancy-related state. The trained algorithm may be adjusted or tuned by adjusting parameters of the trained algorithm (e.g., a set of cutoff values used to classify a cell-free biological sample as described elsewhere herein, or weights of a neural network). The trained algorithm may be adjusted or tuned continuously during the training process or after the training process has completed.

After the trained algorithm is initially trained, a subset of the inputs may be identified as most influential or most important to be included for making high-quality classifications. For example, a subset of the plurality of pregnancy-related state-associated genomic loci may be identified as most influential or most important to be included for making high-quality classifications or identifications of pregnancy-related states (or sub-types of pregnancy-related states). The plurality of pregnancy-related state-associated genomic loci or a subset thereof may be ranked based on classification metrics indicative of each genomic locus's influence or importance toward making high-quality classifications or identifications of pregnancy-related states (or sub-types of pregnancy-related states). Such metrics may be used to reduce, in some cases significantly, the number of input variables (e.g., predictor variables) that may be used to train the trained algorithm to a desired performance level (e.g., based on a desired minimum accuracy, PPV, NPV, clinical sensitivity, clinical specificity, AUC, or a combination thereof). For example, if training the trained algorithm with a plurality comprising several dozen or hundreds of input variables in the trained algorithm results in an accuracy of classification of more than 99%, then training the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%). The subset may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics.

Identifying or Monitoring a Pregnancy-Related State

After using a trained algorithm to process the dataset, the pregnancy-related state or pregnancy-related complication may be identified or monitored in the subject. The identification may be based at least in part on quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites.

The pregnancy-related state may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the pregnancy-related state by the trained algorithm may be calculated as the percentage of independent test samples (e.g., subjects known to have the pregnancy-related state or subjects with negative clinical test results for the pregnancy-related state) that are correctly identified or classified as having or not having the pregnancy-related state.

The pregnancy-related state may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the pregnancy-related state using the trained algorithm may be calculated as the percentage of cell-free biological samples identified or classified as having the pregnancy-related state that correspond to subjects that truly have the pregnancy-related state.

The pregnancy-related state may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the pregnancy-related state using the trained algorithm may be calculated as the percentage of cell-free biological samples identified or classified as not having the pregnancy-related state that correspond to subjects that truly do not have the pregnancy-related state.

The pregnancy-related state may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the pregnancy-related state using the trained algorithm may be calculated as the percentage of independent test samples associated with presence of the pregnancy-related state (e.g., subjects known to have the pregnancy-related state) that are correctly identified or classified as having the pregnancy-related state.

The pregnancy-related state may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the pregnancy-related state using the trained algorithm may be calculated as the percentage of independent test samples associated with absence of the pregnancy-related state (e.g., subjects with negative clinical test results for the pregnancy-related state) that are correctly identified or classified as not having the pregnancy-related state.

In an aspect, the present disclosure provides a method for determining that a subject is at risk of pre-term birth, comprising assaying a cell-free biological sample derived from the subject to generate a dataset that is indicative of said pre-term birth risk at a specificity of at least 80%, and using a trained algorithm that is trained on samples independent of the cell-free biological sample to determine that the subject is at risk of pre-term birth at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

After the pregnancy-related state is identified in a subject, a sub-type of the pregnancy-related state (e.g., selected from among a plurality of sub-types of the pregnancy-related state) may further be identified. The sub-type of the pregnancy-related state may be determined based at least in part on the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites. For example, the subject may be identified as being at risk of a sub-type of pre-term birth (e.g., selected from among a plurality of sub-types of pre-term birth). After identifying the subject as being at risk of a sub-type of pre-term birth, a clinical intervention for the subject may be selected based at least in part on the sub-type of pre-term birth for which the subject is identified as being at risk. In some embodiments, the clinical intervention is selected from a plurality of clinical interventions (e.g., clinically indicated for different sub-types of pre-term birth).

In some embodiments, the trained algorithm may determine that the subject is at risk of pre-term birth of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of pre-term birth at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

Upon identifying the subject as having the pregnancy-related state, the subject may be optionally provided with a therapeutic intervention (e.g., prescribing an appropriate course of treatment to treat the pregnancy-related state of the subject). The therapeutic intervention may comprise a prescription of an effective dose of a drug, a further testing or evaluation of the pregnancy-related state, a further monitoring of the pregnancy-related state, an induction or inhibition of labor, or a combination thereof. If the subject is currently being treated for the pregnancy-related state with a course of treatment, the therapeutic intervention may comprise a subsequent different course of treatment (e.g., to increase treatment efficacy due to non-efficacy of the current course of treatment).

The therapeutic intervention may comprise recommending the subject for a secondary clinical test to confirm a diagnosis of the pregnancy-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

The quantitative measures of sequence reads of the dataset at the panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites may be assessed over a duration of time to monitor a patient (e.g., subject who has pregnancy-related state or who is being treated for pregnancy-related state). In such cases, the quantitative measures of the dataset of the patient may change during the course of treatment. For example, the quantitative measures of the dataset of a patient with decreasing risk of the pregnancy-related state due to an effective treatment may shift toward the profile or distribution of a healthy subject (e.g., a subject without a pregnancy-related complication). Conversely, for example, the quantitative measures of the dataset of a patient with increasing risk of the pregnancy-related state due to an ineffective treatment may shift toward the profile or distribution of a subject with higher risk of the pregnancy-related state or a more advanced pregnancy-related state.

The pregnancy-related state of the subject may be monitored by monitoring a course of treatment for treating the pregnancy-related state of the subject. The monitoring may comprise assessing the pregnancy-related state of the subject at two or more time points. The assessing may be based at least on the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites determined at each of the two or more time points.

In some embodiments, a difference in the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites determined between the two or more time points may be indicative of one or more clinical indications, such as (i) a diagnosis of the pregnancy-related state of the subject, (ii) a prognosis of the pregnancy-related state of the subject, (iii) an increased risk of the pregnancy-related state of the subject, (iv) a decreased risk of the pregnancy-related state of the subject, (v) an efficacy of the course of treatment for treating the pregnancy-related state of the subject, and (vi) a non-efficacy of the course of treatment for treating the pregnancy-related state of the subject.

In some embodiments, a difference in the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites determined between the two or more time points may be indicative of a diagnosis of the pregnancy-related state of the subject. For example, if the pregnancy-related state was not detected in the subject at an earlier time point but was detected in the subject at a later time point, then the difference is indicative of a diagnosis of the pregnancy-related state of the subject. A clinical action or decision may be made based on this indication of diagnosis of the pregnancy-related state of the subject, such as, for example, prescribing a new therapeutic intervention for the subject. The clinical action or decision may comprise recommending the subject for a secondary clinical test to confirm the diagnosis of the pregnancy-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In some embodiments, a difference in the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites determined between the two or more time points may be indicative of a prognosis of the pregnancy-related state of the subject.

In some embodiments, a difference in the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites determined between the two or more time points may be indicative of the subject having an increased risk of the pregnancy-related state. For example, if the pregnancy-related state was detected in the subject both at an earlier time point and at a later time point, and if the difference is a negative difference (e.g., the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites increased from the earlier time point to the later time point), then the difference may be indicative of the subject having an increased risk of the pregnancy-related state. A clinical action or decision may be made based on this indication of the increased risk of the pregnancy-related state, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the pregnancy-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In some embodiments, a difference in the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites determined between the two or more time points may be indicative of the subject having a decreased risk of the pregnancy-related state. For example, if the pregnancy-related state was detected in the subject both at an earlier time point and at a later time point, and if the difference is a positive difference (e.g., the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites decreased from the earlier time point to the later time point), then the difference may be indicative of the subject having a decreased risk of the pregnancy-related state. A clinical action or decision may be made based on this indication of the decreased risk of the pregnancy-related state (e.g., continuing or ending a current therapeutic intervention) for the subject. The clinical action or decision may comprise recommending the subject for a secondary clinical test to confirm the decreased risk of the pregnancy-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In some embodiments, a difference in the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites determined between the two or more time points may be indicative of an efficacy of the course of treatment for treating the pregnancy-related state of the subject. For example, if the pregnancy-related state was detected in the subject at an earlier time point but was not detected in the subject at a later time point, then the difference may be indicative of an efficacy of the course of treatment for treating the pregnancy-related state of the subject. A clinical action or decision may be made based on this indication of the efficacy of the course of treatment for treating the pregnancy-related state of the subject, e.g., continuing or ending a current therapeutic intervention for the subject. The clinical action or decision may comprise recommending the subject for a secondary clinical test to confirm the efficacy of the course of treatment for treating the pregnancy-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In some embodiments, a difference in the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites determined between the two or more time points may be indicative of a non-efficacy of the course of treatment for treating the pregnancy-related state of the subject. For example, if the pregnancy-related state was detected in the subject both at an earlier time point and at a later time point, and if the difference is a negative or zero difference (e.g., the quantitative measures of sequence reads of the dataset at a panel of pregnancy-related state-associated genomic loci (e.g., quantitative measures of RNA transcripts or DNA at the pregnancy-related state-associated genomic loci), proteomic data comprising quantitative measures of proteins of the dataset at a panel of pregnancy-related state-associated proteins, and/or metabolome data comprising quantitative measures of a panel of pregnancy-related state-associated metabolites increased or remained at a constant level from the earlier time point to the later time point), and if an efficacious treatment was indicated at an earlier time point, then the difference may be indicative of a non-efficacy of the course of treatment for treating the pregnancy-related state of the subject. A clinical action or decision may be made based on this indication of the non-efficacy of the course of treatment for treating the pregnancy-related state of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the pregnancy-related state. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, an amniocentesis, a non-invasive prenatal test (NIPT), or any combination thereof.

In another aspect, the present disclosure provides a computer-implemented method for predicting a risk of pre-term birth of a subject, comprising: (a) receiving clinical health data of the subject, wherein the clinical health data comprises a plurality of quantitative or categorical measures of said subject; (b) using a trained algorithm to process the clinical health data of the subject to determine a risk score indicative of the risk of pre-term birth of the subject; and (c) electronically outputting a report indicative of the risk score indicative of the risk of pre-term birth of the subject.

In some embodiments, for example, the clinical health data comprises one or more quantitative measures of the subject, such as age, weight, height, body mass index (BMI), blood pressure, heart rate, glucose levels, number of previous pregnancies, and number of previous births. As another example, the clinical health data can comprise one or more categorical measures, such as race, ethnicity, history of medication or other clinical treatment, history of tobacco use, history of alcohol consumption, daily activity or fitness level, genetic test results, blood test results, imaging results, and fetal screening results.

In some embodiments, the computer-implemented method for predicting a risk of pre-term birth of a subject is performed using a computer or mobile device application. For example, a subject can use a computer or mobile device application to input her own clinical health data, including quantitative and/or categorical measures. The computer or mobile device application can then use a trained algorithm to process the clinical health data to determine a risk score indicative of the risk of pre-term birth of the subject. The computer or mobile device application can then display a report indicative of the risk score indicative of the risk of pre-term birth of the subject.

In some embodiments, the risk score indicative of the risk of pre-term birth of the subject can be refined by performing one or more subsequent clinical tests for the subject. For example, the subject can be referred by a physician for one or more subsequent clinical tests (e.g., an ultrasound imaging or a blood test) based on the initial risk score. Next, the computer or mobile device application may process results from the one or more subsequent clinical tests using a trained algorithm to determine an updated risk score indicative of the risk of pre-term birth of the subject.

In some embodiments, the risk score comprises a likelihood of the subject having a pre-term birth within a pre-determined duration of time. For example, the pre-determined duration of time may be about 1 hour, about 2 hours, about 4 hours, about 6 hours, about 8 hours, about 10 hours, about 12 hours, about 14 hours, about 16 hours, about 18 hours, about 20 hours, about 22 hours, about 24 hours, about 1.5 days, about 2 days, about 2.5 days, about 3 days, about 3.5 days, about 4 days, about 4.5 days, about 5 days, about 5.5 days, about 6 days, about 6.5 days, about 7 days, about 8 days, about 9 days, about 10 days, about 12 days, about 14 days, about 3 weeks, about 4 weeks, about 5 weeks, about 6 weeks, about 7 weeks, about 8 weeks, about 9 weeks, about 10 weeks, about 11 weeks, about 12 weeks, about 13 weeks, or more than about 13 weeks.

Outputting a Report of the Pregnancy-Related State

After the pregnancy-related state is identified or an increased risk of the pregnancy-related state is monitored in the subject, a report may be electronically outputted that is indicative of (e.g., identifies or provides an indication of) the pregnancy-related state of the subject. The subject may not display a pregnancy-related state (e.g., is asymptomatic of the pregnancy-related state such as a pregnancy-related complication). The report may be presented on a graphical user interface (GUI) of an electronic device of a user. The user may be the subject, a caretaker, a physician, a nurse, or another health care worker.

The report may include one or more clinical indications such as (i) a diagnosis of the pregnancy-related state of the subject, (ii) a prognosis of the pregnancy-related state of the subject, (iii) an increased risk of the pregnancy-related state of the subject, (iv) a decreased risk of the pregnancy-related state of the subject, (v) an efficacy of the course of treatment for treating the pregnancy-related state of the subject, and (vi) a non-efficacy of the course of treatment for treating the pregnancy-related state of the subject. The report may include one or more clinical actions or decisions made based on these one or more clinical indications. Such clinical actions or decisions may be directed to therapeutic interventions, induction or inhibition of labor, or further clinical assessment or testing of the pregnancy-related state of the subject.

For example, a clinical indication of a diagnosis of the pregnancy-related state of the subject may be accompanied with a clinical action of prescribing a new therapeutic intervention for the subject. As another example, a clinical indication of an increased risk of the pregnancy-related state of the subject may be accompanied with a clinical action of prescribing a new therapeutic intervention or switching therapeutic interventions (e.g., ending a current treatment and prescribing a new treatment) for the subject. As another example, a clinical indication of a decreased risk of the pregnancy-related state of the subject may be accompanied with a clinical action of continuing or ending a current therapeutic intervention for the subject. As another example, a clinical indication of an efficacy of the course of treatment for treating the pregnancy-related state of the subject may be accompanied with a clinical action of continuing or ending a current therapeutic intervention for the subject. As another example, a clinical indication of a non-efficacy of the course of treatment for treating the pregnancy-related state of the subject may be accompanied with a clinical action of ending a current therapeutic intervention and/or switching to (e.g., prescribing) a different new therapeutic intervention for the subject.

Computer Systems

Figure 2:
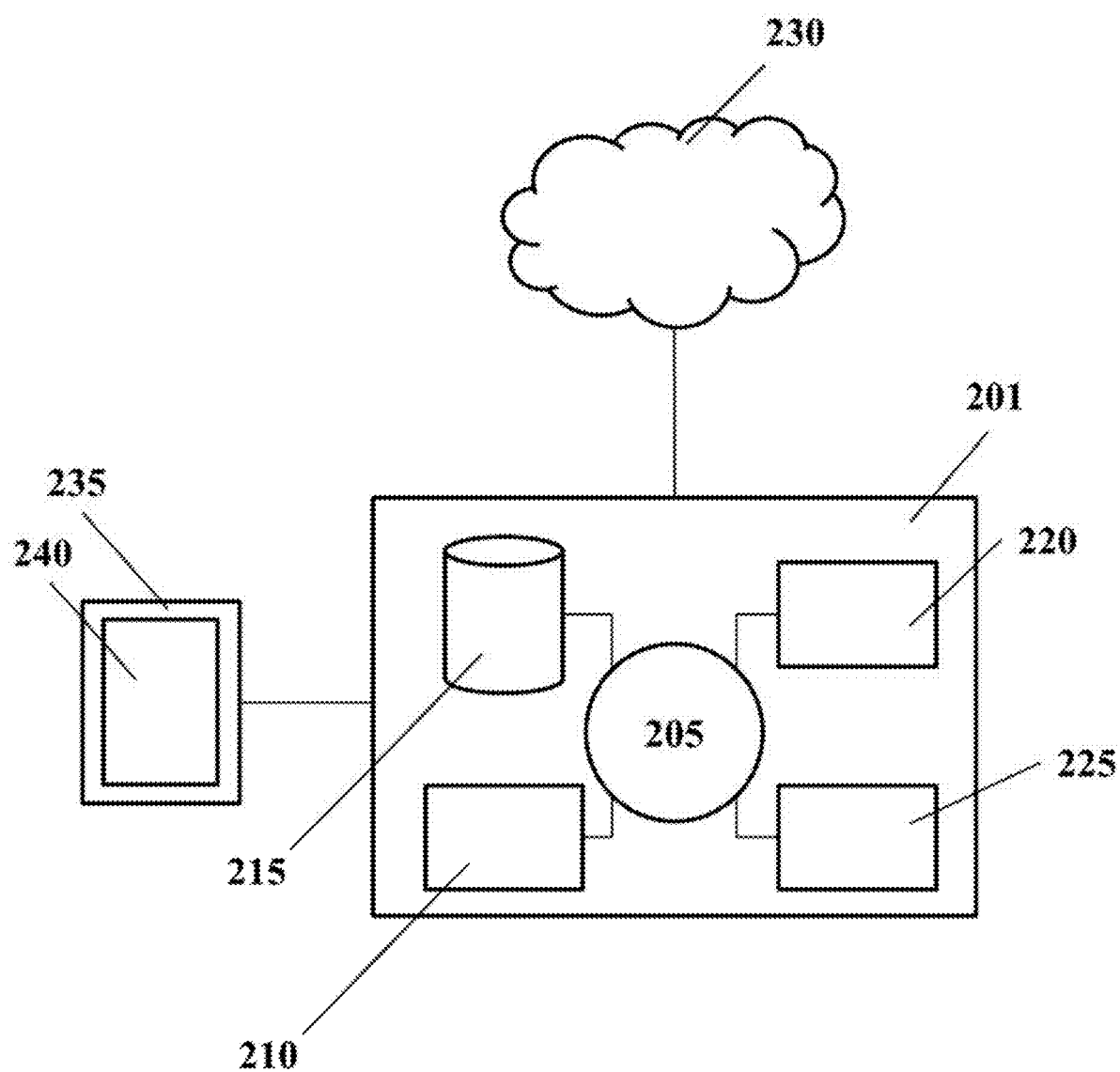
FIG. 2 illustrates a computer system that is programmed or otherwise configured to implement methods provided herein.

The present disclosure provides computer systems that are programmed to implement methods of the disclosure. FIG. 2 shows a computer system 201 that is programmed or otherwise configured to, for example, (i) train and test a trained algorithm, (ii) use the trained algorithm to process data to determine a pregnancy-related state of a subject, (iii) determine a quantitative measure indicative of a pregnancy-related state of a subject, (iv) identify or monitor the pregnancy-related state of the subject, and (v) electronically output a report that indicative of the pregnancy-related state of the subject.

The computer system 201 can regulate various aspects of analysis, calculation, and generation of the present disclosure, such as, for example, (i) training and testing a trained algorithm, (ii) using the trained algorithm to process data to determine a pregnancy-related state of a subject, (iii) determining a quantitative measure indicative of a pregnancy-related state of a subject, (iv) identifying or monitoring the pregnancy-related state of the subject, and (v) electronically outputting a report that indicative of the pregnancy-related state of the subject. The computer system 201 can be an electronic device of a user or a computer system that is remotely located with respect to the electronic device. The electronic device can be a mobile electronic device.

The computer system 201 includes a central processing unit (CPU, also "processor" and "computer processor" herein) 205, which can be a single core or multi core processor, or a plurality of processors for parallel processing. The computer system 201 also includes memory or memory location 210 (e.g., random-access memory, read-only memory, flash memory), electronic storage unit 215 (e.g., hard disk), communication interface 220 (e.g., network adapter) for communicating with one or more other systems, and peripheral devices 225, such as cache, other memory, data storage and/or electronic display adapters. The memory 210, storage unit 215, interface 220 and peripheral devices 225 are in communication with the CPU 205 through a communication bus (solid lines), such as a motherboard. The storage unit 215 can be a data storage unit (or data repository) for storing data. The computer system 201 can be operatively coupled to a computer network ("network") 230 with the aid of the communication interface 220. The network 230 can be the Internet, an internet and/or extranet, or an intranet and/or extranet that is in communication with the Internet.

The network 230 in some cases is a telecommunication and/or data network. The network 230 can include one or more computer servers, which can enable distributed computing, such as cloud computing. For example, one or more computer servers may enable cloud computing over the network 230 ("the cloud") to perform various aspects of analysis, calculation, and generation of the present disclosure, such as, for example, (i) training and testing a trained algorithm, (ii) using the trained algorithm to process data to determine a pregnancy-related state of a subject, (iii) determining a quantitative measure indicative of a pregnancy-related state of a subject, (iv) identifying or monitoring the pregnancy-related state of the subject, and (v) electronically outputting a report that indicative of the pregnancy-related state of the subject. Such cloud computing may be provided by cloud computing platforms such as, for example, Amazon Web Services (AWS), Microsoft Azure, Google Cloud Platform, and IBM cloud. The network 230, in some cases with the aid of the computer system 201, can implement a peer-to-peer network, which may enable devices coupled to the computer system 201 to behave as a client or a server.

The CPU 205 may comprise one or more computer processors and/or one or more graphics processing units (GPUs). The CPU 205 can execute a sequence of machine-readable instructions, which can be embodied in a program or software. The instructions may be stored in a memory location, such as the memory 210. The instructions can be directed to the CPU 205, which can subsequently program or otherwise configure the CPU 205 to implement methods of the present disclosure. Examples of operations performed by the CPU 205 can include fetch, decode, execute, and writeback.

The CPU 205 can be part of a circuit, such as an integrated circuit. One or more other components of the system 201 can be included in the circuit. In some cases, the circuit is an application specific integrated circuit (ASIC).

The storage unit 215 can store files, such as drivers, libraries and saved programs. The storage unit 215 can store user data, e.g., user preferences and user programs. The computer system 201 in some cases can include one or more additional data storage units that are external to the computer system 201, such as located on a remote server that is in communication with the computer system 201 through an intranet or the Internet.

The computer system 201 can communicate with one or more remote computer systems through the network 230. For instance, the computer system 201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 201 via the network 230.

Methods as described herein can be implemented by way of machine (e.g., computer processor) executable code stored on an electronic storage location of the computer system 201, such as, for example, on the memory 210 or electronic storage unit 215. The machine executable or machine readable code can be provided in the form of software. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 201 can include or be in communication with an electronic display 235 that comprises a user interface (UI) 240 for providing, for example, (i) a visual display indicative of training and testing of a trained algorithm, (ii) a visual display of data indicative of a pregnancy-related state of a subject, (iii) a quantitative measure of a pregnancy-related state of a subject, (iv) an identification of a subject as having a pregnancy-related state, or (v) an electronic report indicative of the pregnancy-related state of the subject. Examples of UIs include, without limitation, a graphical user interface (GUI) and web-based user interface. Methods and systems of the present disclosure can be implemented by way of one or more algorithms. An algorithm can be implemented by way of software upon execution by the central processing unit 205. The algorithm can, for example, (i) train and test a trained algorithm, (ii) use the trained algorithm to process data to determine a pregnancy-related state of a subject, (iii) determine a quantitative measure indicative of a pregnancy-related state of a subject, (iv) identify or monitor the pregnancy-related state of the subject, and (v) electronically output a report that indicative of the pregnancy-related state of the subject.

EXAMPLES

Example 1: Cohorts of Subjects

Figure 3A:
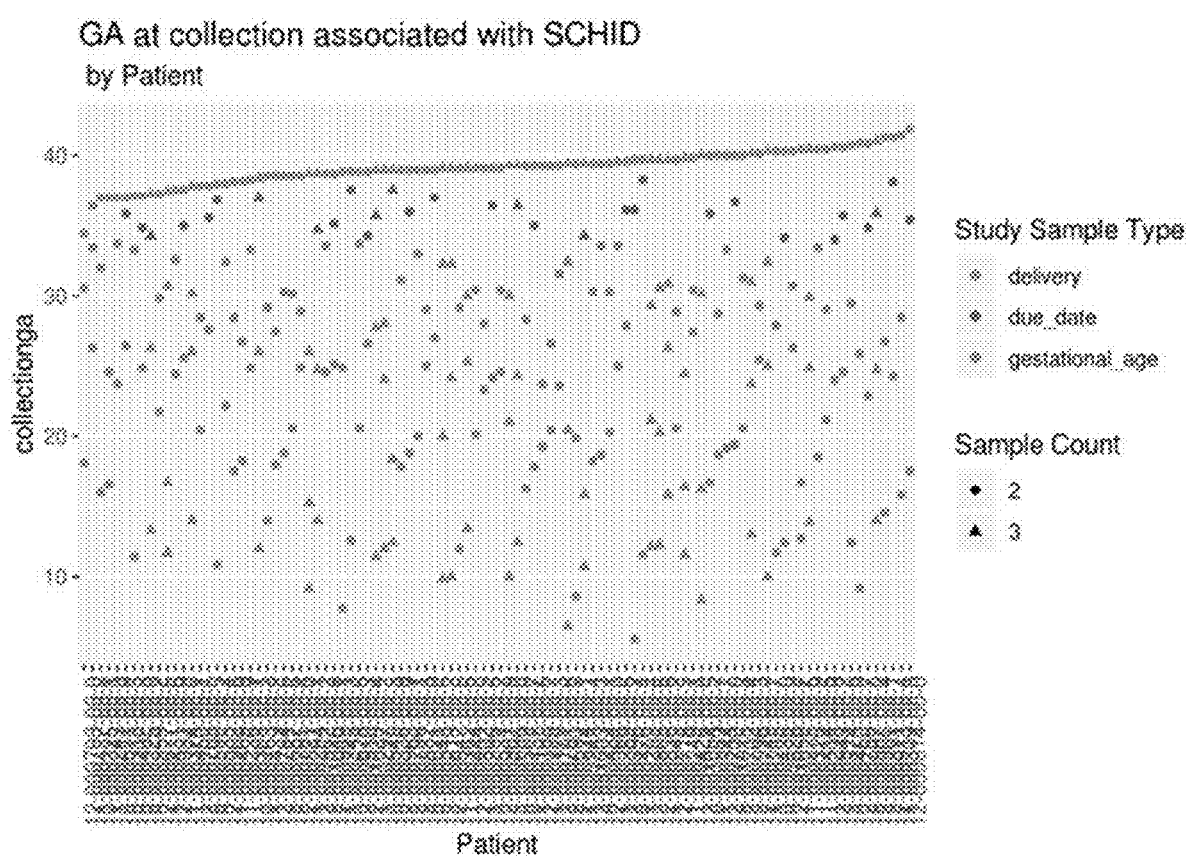
FIG. 3A shows a first cohort of subjects (e.g., pregnant women) that was established (with patient identification numbers shown on the x-axis), from which one or more biological samples (e.g., 2 or 3 each) were collected and assayed at different time points corresponding to an estimated gestational age (shown on the y-axis, in increasing order of estimated gestational age at delivery) of a fetus of each subject, in accordance with disclosed embodiments.
Figure 3B:
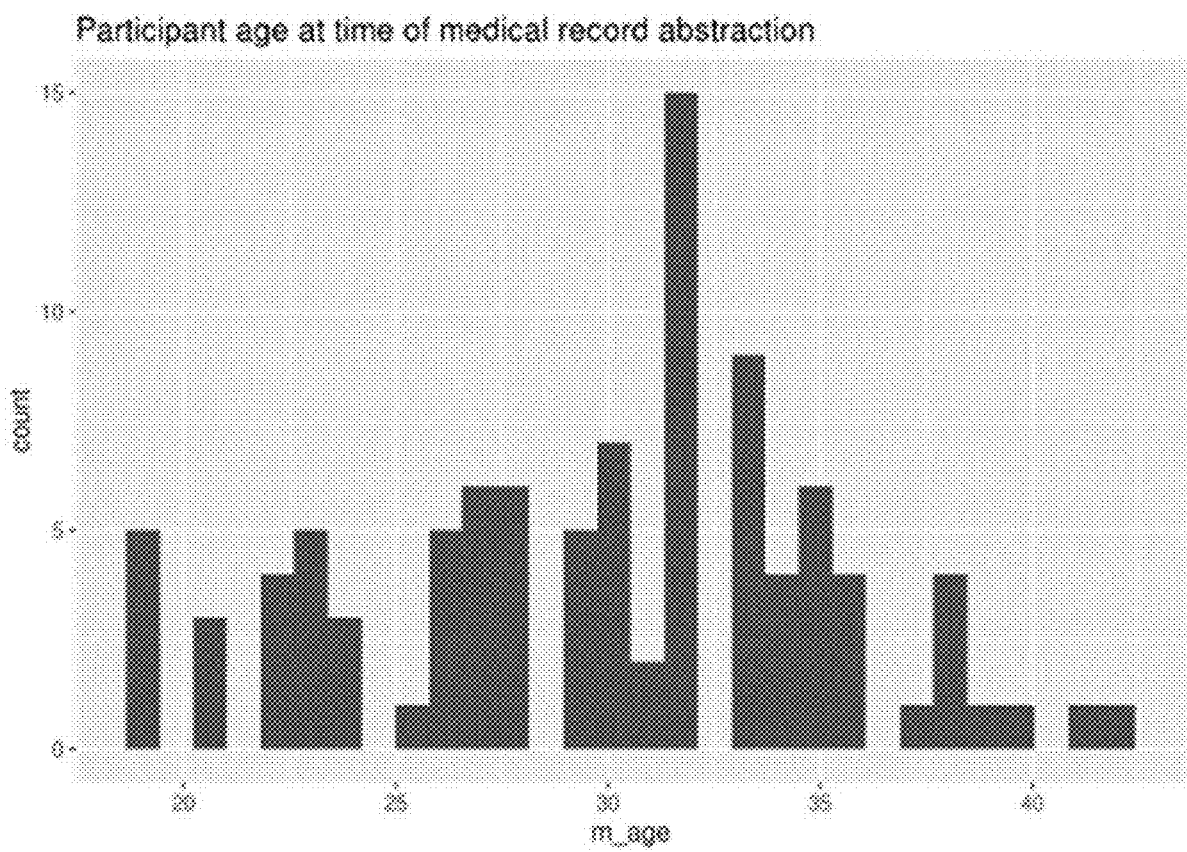
FIG. 3B shows a distribution of participants in the first cohort based on each participant's age at the time of medical record abstraction, in accordance with disclosed embodiments.
Figure 3C:
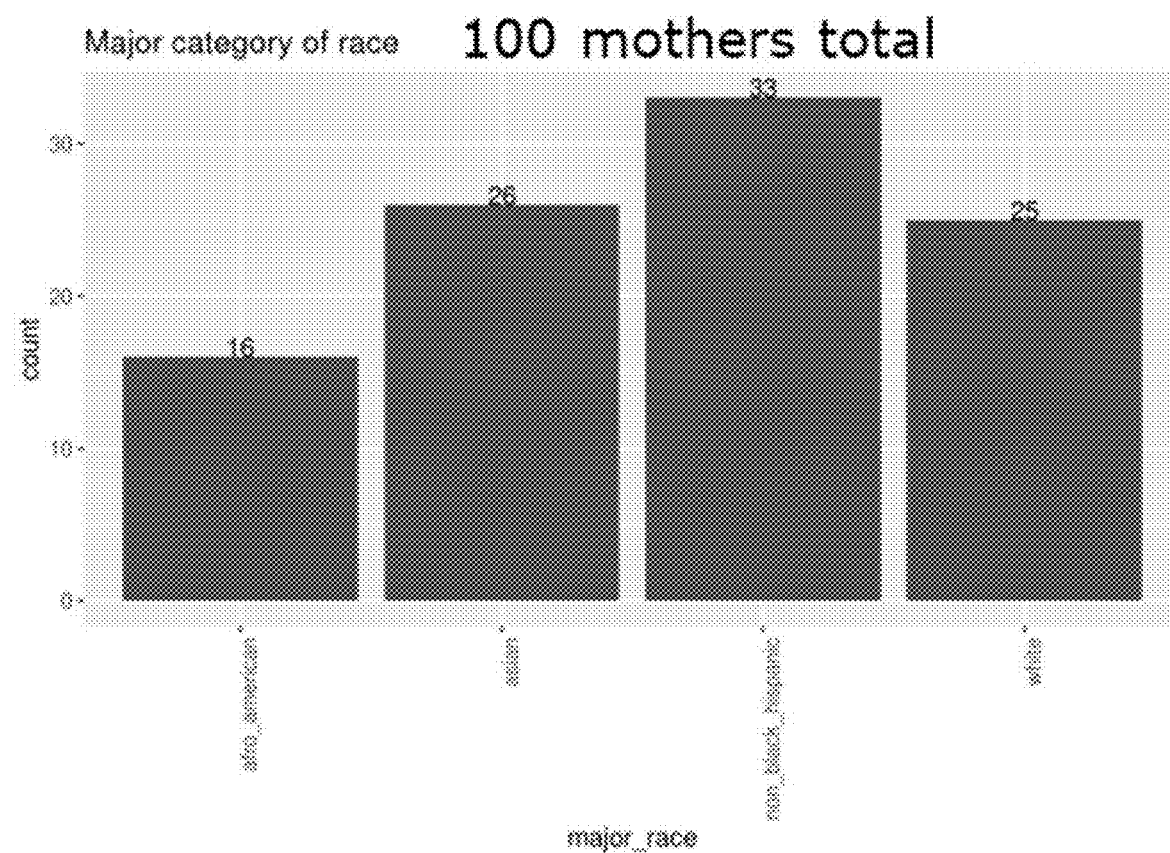
FIG. 3C shows a distribution of 100 participants in the first cohort based on each participant's race, in accordance with disclosed embodiments.
Figure 3D:
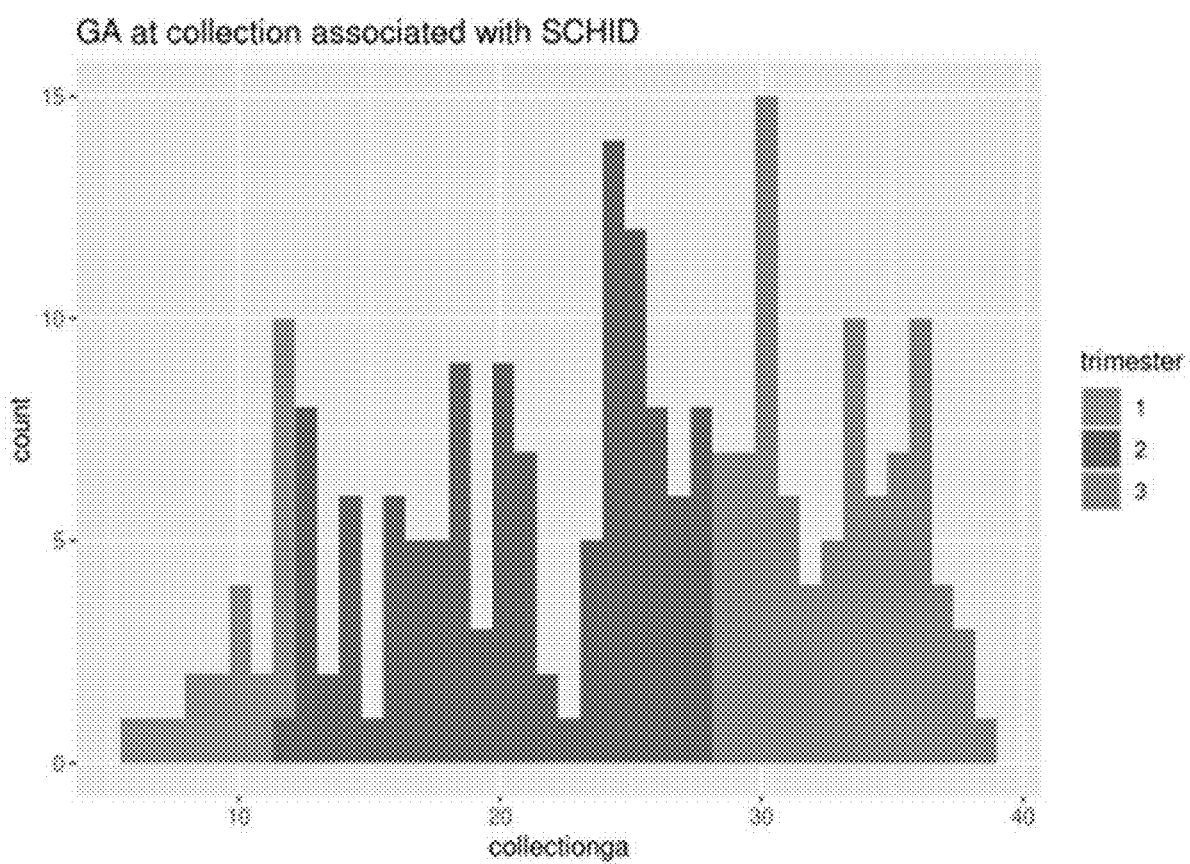
FIG. 3D shows a distribution of collected samples in the gestational age cohort based on each participant's estimated gestational age and trimester at the time of collection of each sample, in accordance with disclosed embodiments.
Figure 3E:
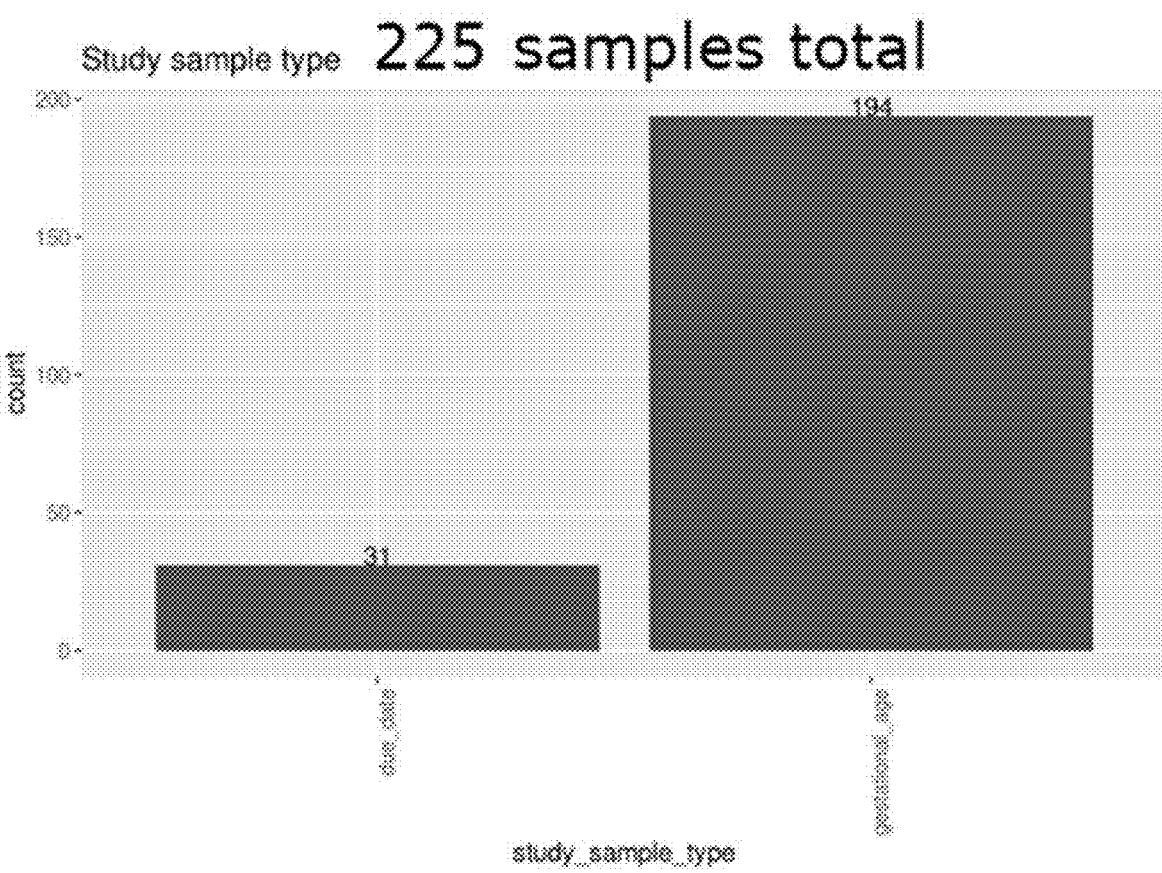
FIG. 3E shows a distribution of 225 collected samples in the first cohort based on the study sample type of the collected samples, in accordance with disclosed embodiments.

As shown in FIG. 3A, a first cohort of subjects (e.g., pregnant women) was established (with patient identification numbers shown on the x-axis), from which one or more biological samples (e.g., 2 or 3 each) were collected and assayed at different time points corresponding to an estimated gestational age (shown on the y-axis, in increasing order of estimated gestational age at delivery) of a fetus of each subject, using methods and systems of the present disclosure. For example, the estimated gestational age (shown on the y-axis) may be determined using methods such as ultrasound imaging, a last menstrual period (LMP) date, or a combination thereof, and may range from 0 to about 42 weeks. The first cohort includes subjects from whom different sample types were collected for use in different studies, including studies for the prediction of delivery, prediction of due date, and prediction of actual gestational age of a fetus of each subject. FIG. 3B shows a distribution of participants in the first cohort based on each participant's age at the time of medical record abstraction. FIG. 3C shows a distribution of 100 participants in the first cohort based on each participant's race. FIG. 3D shows a distribution of collected samples in the gestational age cohort based on each participant's estimated gestational age and trimester at the time of collection of each sample. FIG. 3E shows a distribution of 225 collected samples in the first cohort based on the study sample type of the collected samples.

Figure 4A:
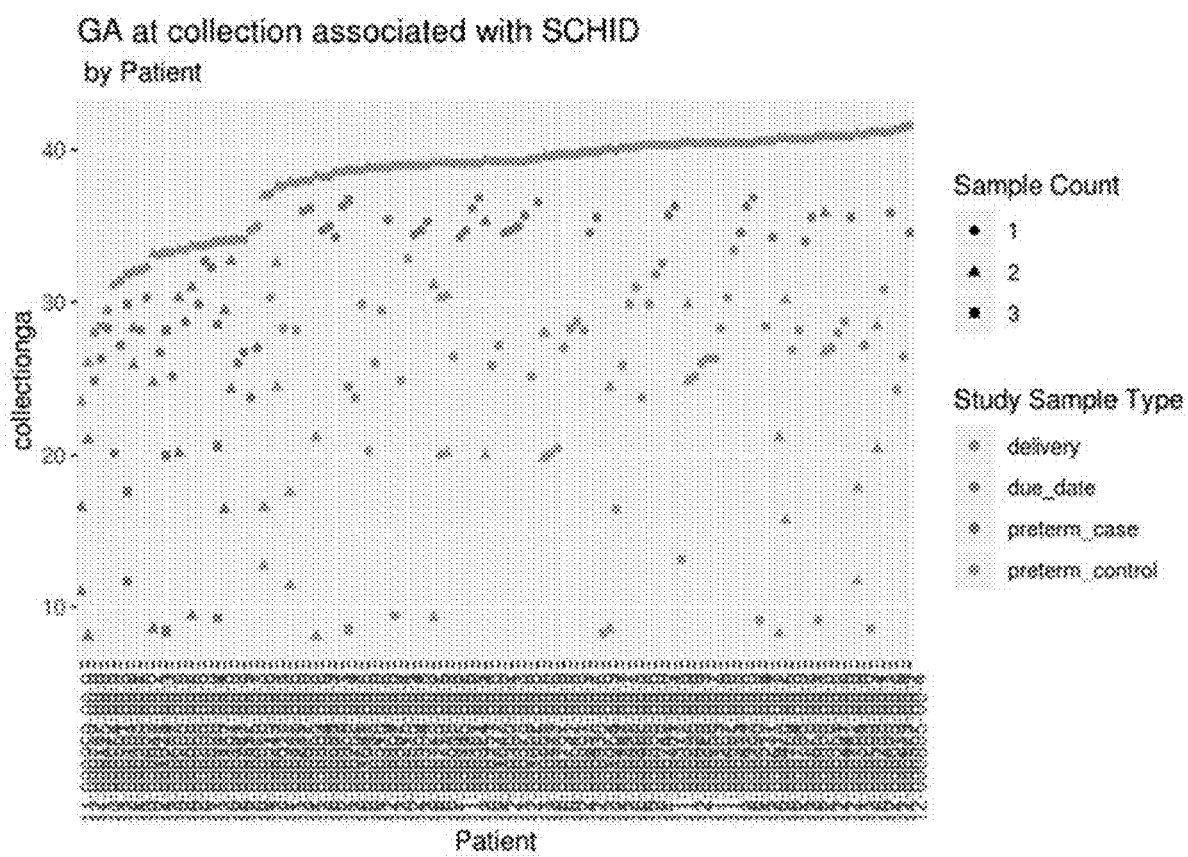
FIG. 4A shows a second cohort of subjects (e.g., pregnant women) that was established (with patient identification numbers shown on the x-axis), from which one or more biological samples (e.g., 1, 2, or 3 each) were collected and assayed at different time points corresponding to an estimated gestational age (shown on the y-axis, in increasing order of estimated gestational age at delivery) of a fetus of each subject, in accordance with disclosed embodiments.
Figure 4B:
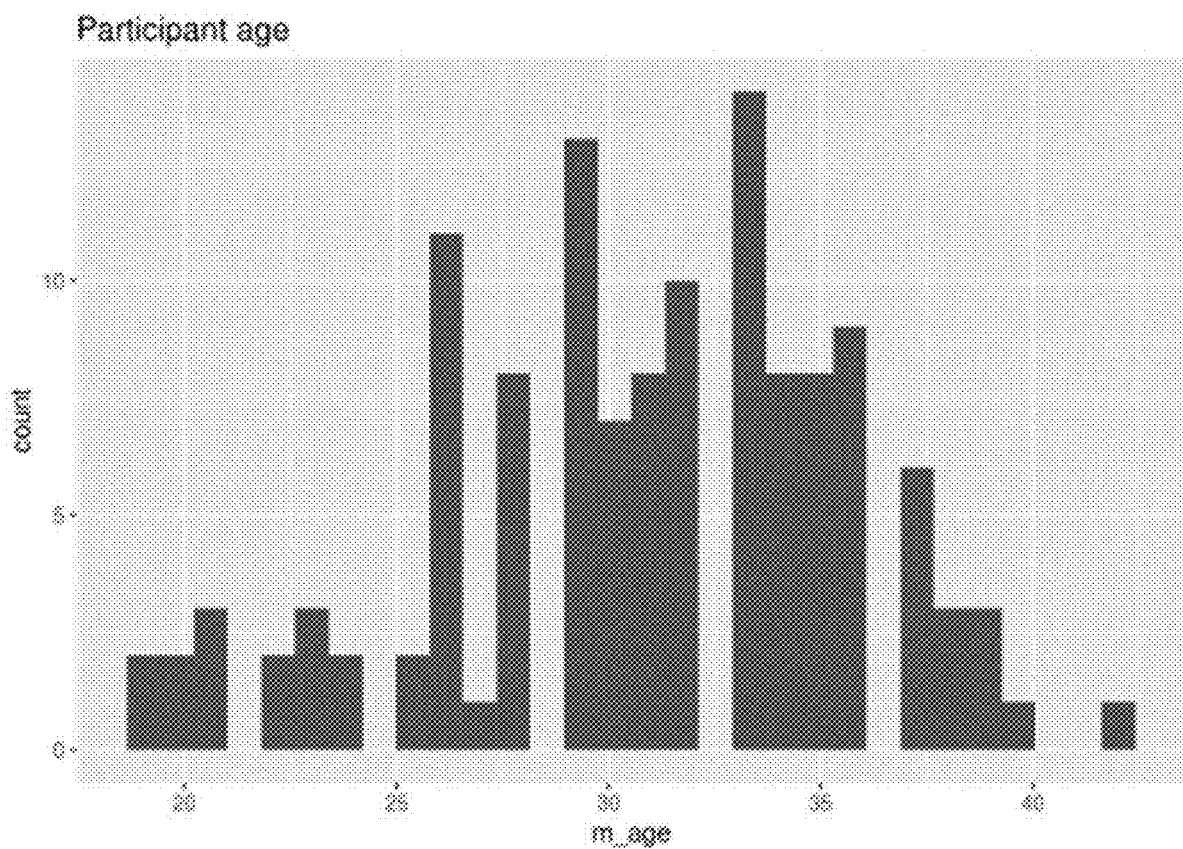
FIG. 4B shows a distribution of participants in the second cohort based on each participant's age at the time of medical record abstraction, in accordance with disclosed embodiments.
Figure 4C:
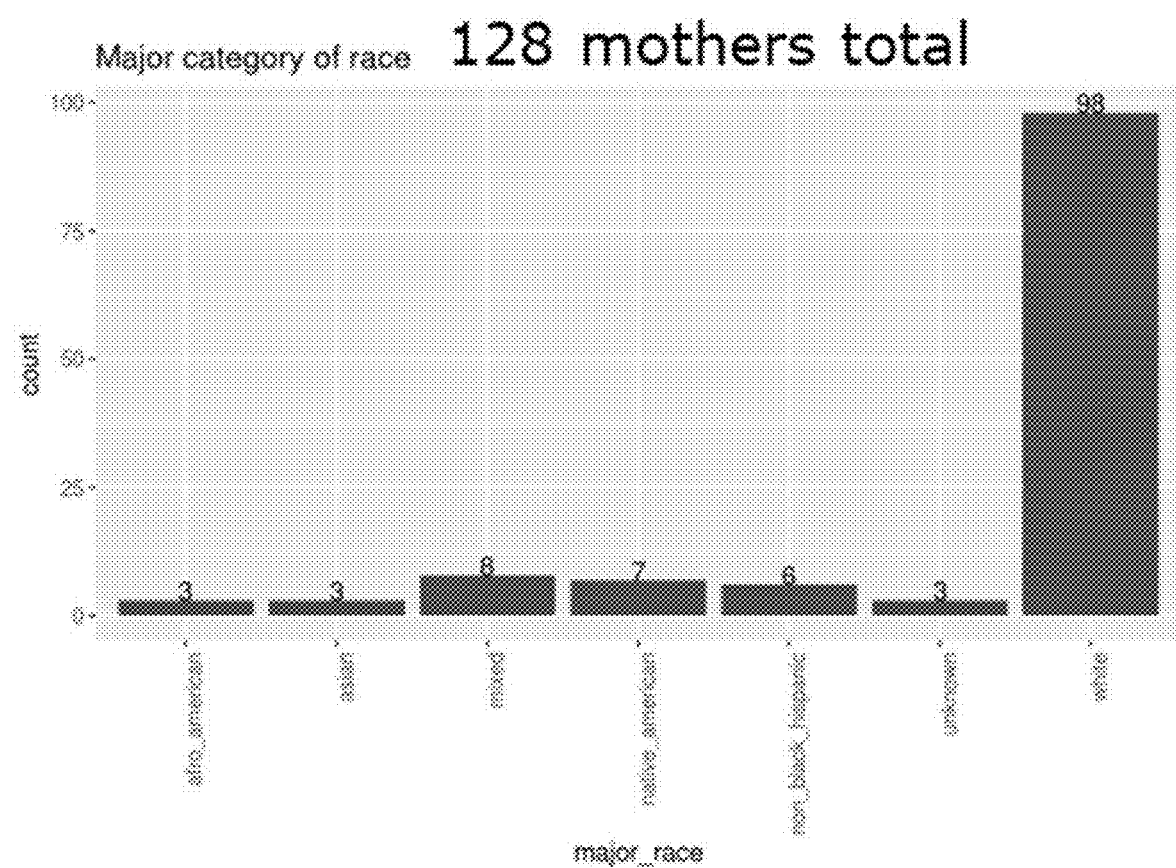
FIG. 4C shows a distribution of 128 participants in the second cohort based on each participant's race, in accordance with disclosed embodiments.
Figure 4D:
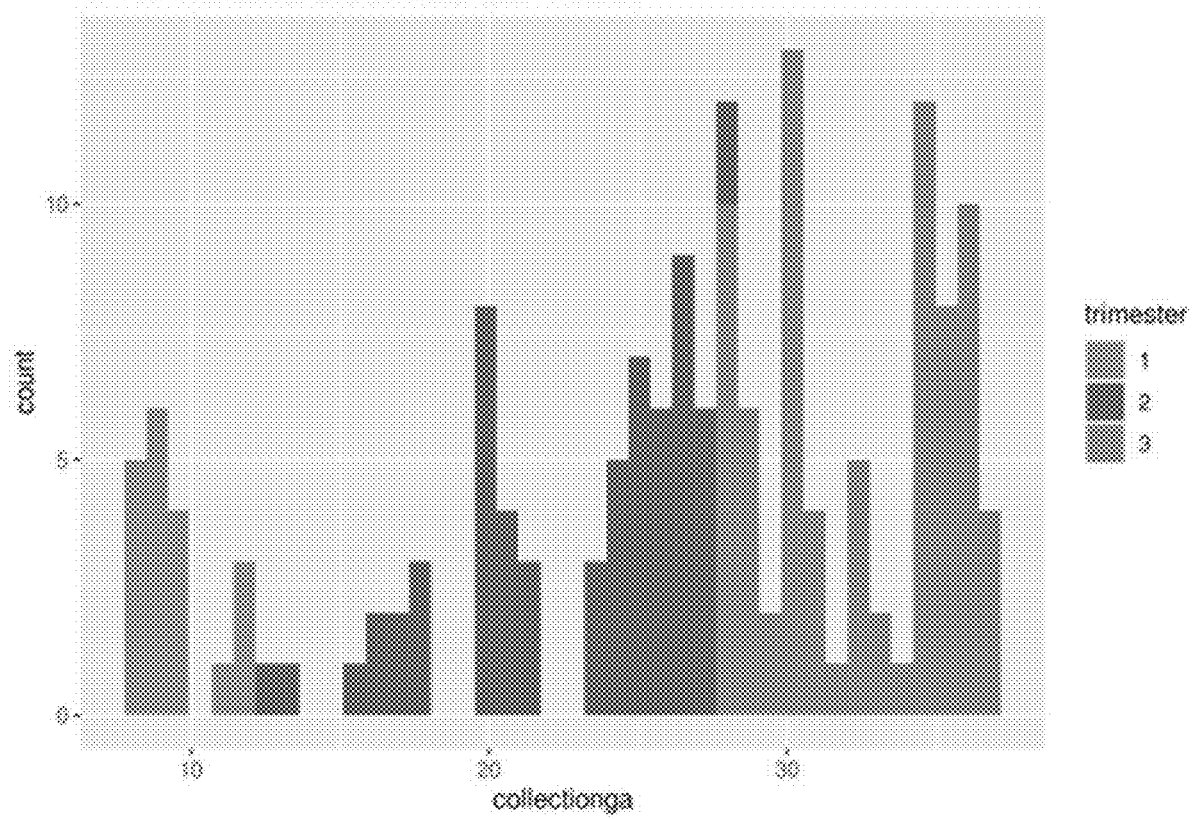
FIG. 4D shows a distribution of collected samples in the second cohort based on each participant's estimated gestational age and trimester at the time of collection of each sample, in accordance with disclosed embodiments.
Figure 4E:
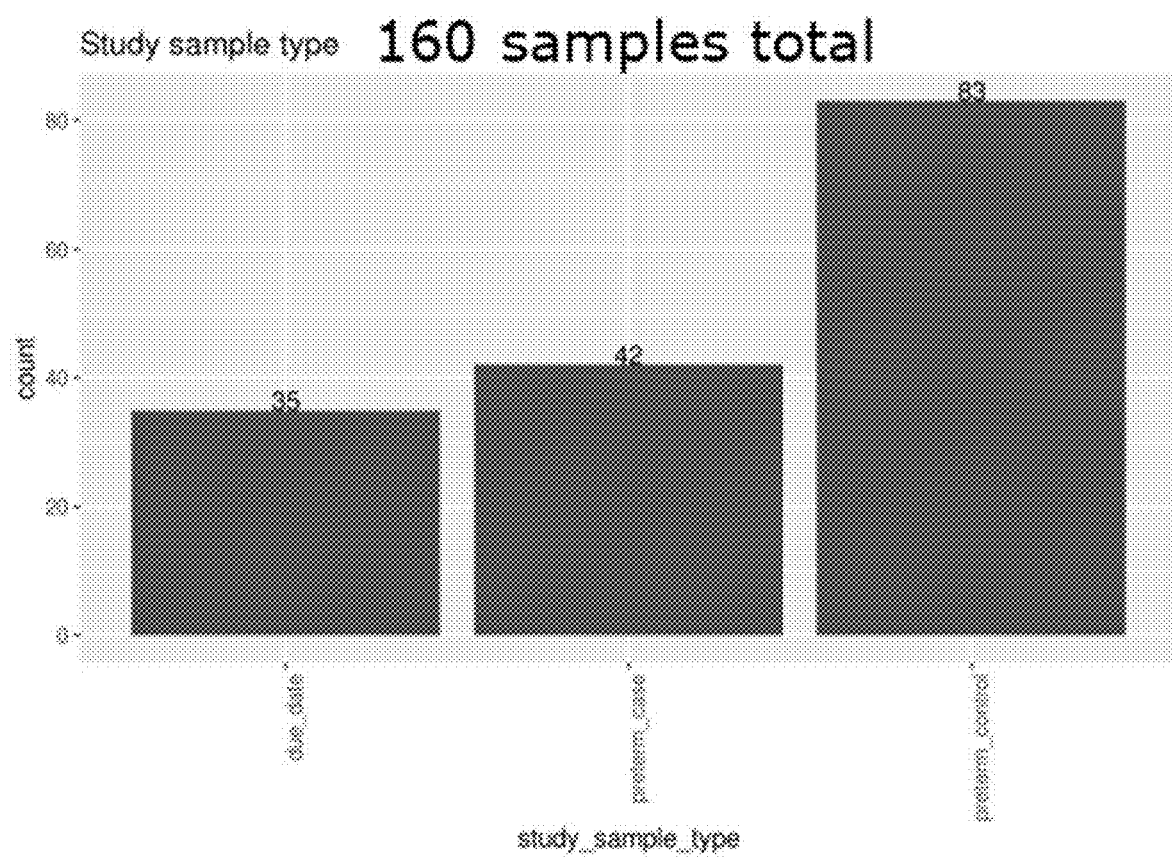
FIG. 4E shows a distribution of 160 collected samples in the second cohort based on the study sample type of the collected samples, in accordance with disclosed embodiments.

As shown in FIG. 4A, a second cohort of subjects (e.g., pregnant women) was established (with patient identification numbers shown on the x-axis), from which one or more biological samples (e.g., 1, 2, or 3 each) were collected and assayed at different time points corresponding to an estimated gestational age (shown on the y-axis, in increasing order of estimated gestational age at delivery) of a fetus of each subject, using methods and systems of the present disclosure. For example, the estimated gestational age (shown on the y-axis) may be determined using methods such as ultrasound imaging, a last menstrual period (LMP) date, or a combination thereof, and may range from 0 to about 42 weeks. The second cohort includes subjects from whom different sample types were collected for use in different studies, including studies for the prediction of pre-term birth, prediction of delivery, prediction of due date, and prediction of actual gestational age of a fetus of each subject. FIG. 4B shows a distribution of participants in the second cohort based on each participant's age at the time of medical record abstraction. FIG. 4C shows a distribution of 128 participants in the second cohort based on each participant's race. FIG. 4D shows a distribution of collected samples in the second cohort based on each participant's estimated gestational age and trimester at the time of collection of each sample. FIG. 4E shows a distribution of 160 collected samples in the second cohort based on the study sample type of the collected samples.

Example 2: Prediction of Due Date

Figure 5A:
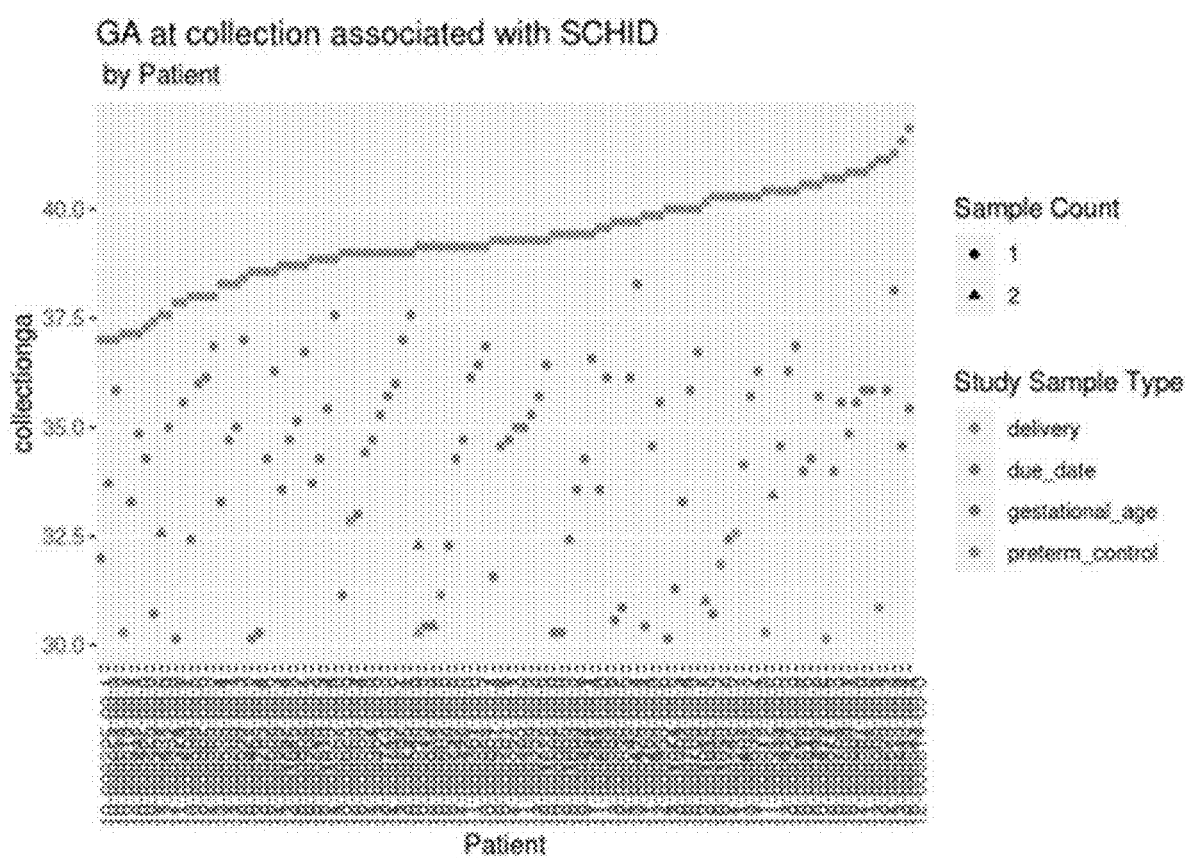
FIG. 5A shows a due date cohort of subjects (e.g., pregnant women) that was established (with patient identification numbers shown on the x-axis), from which one or more biological samples (e.g., 1 or 2 each) were collected and assayed at different time points corresponding to an estimated gestational age (shown on the y-axis, in increasing order of estimated gestational age at delivery) of a fetus of each subject, in accordance with disclosed embodiments.

As shown in FIG. 5A, a due date cohort of subjects (e.g., pregnant women) was established (with patient identification numbers shown on the x-axis), from which one or more biological samples (e.g., 1 or 2 each) were collected and assayed at different time points corresponding to an estimated gestational age (shown on the y-axis, in increasing order of estimated gestational age at delivery) of a fetus of each subject, using methods and systems of the present disclosure. The due date cohort included subjects from the first cohort and second cohort, as described in Example 1. The due date cohort includes subjects from whom different sample types were collected for use in different studies, including studies for the prediction of pre-term birth (e.g., as controls), prediction of delivery, prediction of due date, and prediction of actual gestational age of a fetus of each subject.

Figure 5B:
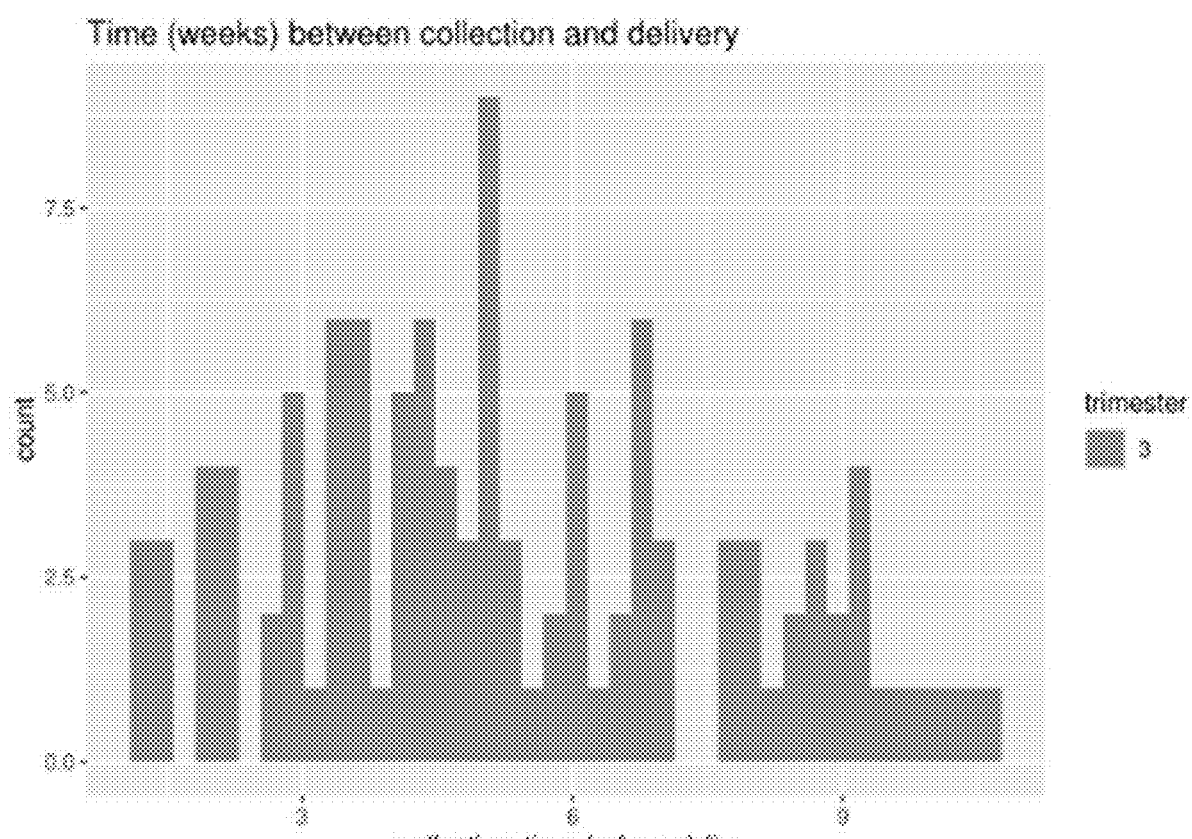
FIG. 5B shows a distribution of collected samples in the due date cohort based on the time between the date of sample collection and the date of delivery (time to delivery), in accordance with disclosed embodiments.

FIG. 5B shows a distribution of collected samples in the due date cohort based on the time between the date of sample collection and the date of delivery (time to delivery). All samples were collected in the third trimester of pregnancy, less than 12 weeks before the date of delivery, of which 59 samples had a time-to-delivery of less than 7.5 weeks and 43 samples had a time-to-delivery of less than 5 weeks. Using systems and methods of the present disclosure, a first set of predictive models was generated from the 59 samples with a time-to-delivery of less than 7.5 weeks, and a second set of predictive models was generated from the 43 samples with a time-to-delivery of less than 5 weeks. The sets of predictive models included a predictive model generated with estimated due date information (e.g., determined using estimated gestational age from ultrasound measurements) and without the estimated due date information. Each of the predictive models comprised a linear regression model with elastic net regularization. The generation of the predictive models included identifying four sets of genes which had the highest correlation with (e.g., were most predictive of) due date (e.g., as measured by time to delivery) among the respective cohorts, including (1) less than 7.5 weeks time-to-delivery with estimated due date information, (2) less than 7.5 weeks time-to-delivery without estimated due date information, (3) less than 5 weeks time-to-delivery with estimated due date information, and (4) less than 5 weeks time-to-delivery without estimated due date information. These four sets of genes that are predictive for due date are listed in Table 1.

TABLE 1

Sets of Genes Predictive for Due Date by Cohort

| Cohort | Predictive Genes Included in Predictive Model | Predictive Genes Not Included in Predictive Model |
| --- | --- | --- |
| <7.5 weeks time-to-delivery with estimated due date info | ACKR2, AKAP3, ANO5, C1orf21, C2orf42, CARNS1, CASC15, CCDC102B, CDC45, CDIPT, CMTM1, collectionga, COPS8, CTD-2267D19.3, CTD-2349P21.9, DDX11L1, DGUOK, DPAGT1, EIF4A1P2, FANK1, FERMT1, FKRP, GAMT, GOLGA6L4, KLLN, LINC01347, LTA, MAPK12, METRN, MPC2, MYL12BP1, NME4, NPM1P30, PCLO, PIF1, PTP4A3, RIMKLB, RP13-88F20.1, S100B, SIGLEC14, SLAIN1, | ADAMTS10, ADCY6, ATP9A, CCDC173, CLIC4P1, CXorf65, KBTBD11, MKRN4P, MKRN9P, NEXN-AS1, SMG1P2, ST13P3, XXbac-BPG252P9.9, ZNF114 |

TABLE 1-continued

Sets of Genes Predictive for Due Date by Cohort

| Cohort | Predictive Genes Included in Predictive Model | Predictive Genes Not Included in Predictive Model |
|---|---|---|
| | SPATA33, STAT1, TFAP2C, TMEM94, TMSB4XP8, TRGV10, ZNF124, ZNF713 | |
| <7.5 weeks time-to-delivery without estimated due date info | ACKR2, AKAP3, ANO5, C1orf21, C2orf42, CARNS1, CASC15, CCDC102B, CDC45, CDIPT, CMTM1, COPS8, CTD-2267D19.3, CTD-2349P21.9, CXorf65, DDX11L1, DGUOK, DPAGT1, EIF4A1P2, FANK1, FERMT1, FKRP, GAMT, GOLGA6L4, KLLN, LINC01347, LTA, MAPK12, METRN, MKRN4P, MPC2, MYL12BP1, NME4, NPM1P30, PCLO, PIF1, PTP4A3, RIMKLB, RP13-88F20.1, S100B, SIGLEC14, SLAIN1, SPATA33, TFAP2C, TMSB4XP8, TRGV10, ZNF124 | ADAMTS10, ADCY6, ATP9A, CCDC173, CLIC4P1, KBTBD11, MKRN9P, NEXN-AS1, SMG1P2, ST13P3, STAT1, TMEM94, XXbac-BPG252P9.9, ZNF114, ZNF713 |
| <5 weeks time-to-delivery with estimated due date info | ATP6V1E1P1, ATP8A2, C2orf68, CACNB3, CD40, CDKL4, CDKL5, CEP152, CLEC4D, COL18A1, collectionga, COX16, CTBS, CTD-2272G21.2, CXCL2, CXCL8, DHRS7B, DPPA4, EIF5A2, FERMT1, GNB1L, IFITM3, KATNAL1, LRCH4, MBD6, MIR24-2, MTSS1, MYSM1, NCK1-AS1, NPIPB4, NR1H4, PDE1C, PEMT, PEX7, PIF1, PPP2R3A, PXDN, RABIF, SERTAD3, SIGLEC14, SLC25A53, SPANXN4, SSH3, SUPT3H, TMEM150C, TNFAIP6, UPP1, XKR8, ZC2HC1C, ZMYM1, ZNF124 | AB019441.29, AC004076.9, ACKR2, ADAMTS10, ADM, AP5B1, APOE, AQP9, ARHGEF40, BCL3, CA4, CCDC84, CCR3, CD177, CDPF1, CFAP46, CHST7, CLYBL, CMTM1, CRADD, CSF3R, CXCL1, DAPK2, DLEC1, DPAGT1, ECHDC2, ERP27, FCGR3B, FKRP, FUT7, GZMM, HAUS4, HKDC1, HMGB1P11, IGLV3-21, IL18R1, IRX3, KBTBD11, KCNJ2, KDM6B, LEMD2, LINC00694, LIPE[31 AS1, LMF2, LMLN-AS1, LPCAT4, LRG1, MAP3K10, MAP3K6, MAPK12, METTL26, MGAM, MID1IP1, MIF-AS1, MME, MRPL23, NAP1L4P3, NLRP6, NPIPA5, NUP58, OPRL1, PADI2, PGS1, POR, RBKS, RNASET2, SDCBPP2, SHE, SUMO2, SUOX, SURF1, TATDN2, TFE3, TMCC3, TMEM8A, TMEM94, TOR1B, UNKL, ZDHHC18, ZNF668 |
| <5 weeks time-to-delivery without estimated due date info | C2orf68, CACNB3, CD40, CDKL5, CTBS, CTD-2272G21.2, CXCL8, DHRS7B, EIF5A2, IFITM3, MIR24-2, MTSS1, MYSM1, NCK1-AS1, NR1H4, PDE1C, PEMT, PEX7, PIF1, PPP2R3A, RABIF, SIGLEC14, 5LC25A53, SPANXN4, SUPT3H, ZC2HC1C, ZMYM1, ZNF124 | AB019441.29, AC004076.9, ACKR2, ADAMTS10, ADM, AP5B1, APOE, AQP9, ARHGEF40, ATP6V1E1P1, ATP8A2, BCL3, CA4, CCDC84, CCR3, CD177, CDKL4, CDPF1, CEP152, CFAP46, CHST7, CLEC4D, CLYBL, CMTM1, COL18A1, COX16, CRADD, CSF3R, CXCL1, CXCL2, DAPK2, DLEC1, DPAGT1, DPPA4, ECHDC2, ERP27, FCGR3B, FERMT1, FKRP, FUT7, GNB1L, GZMM, HAUS4, HKDC1, HMGB1P11, IGLV3-21, IL18R1, IRX3, KATNAL1, KBTBD11, KCNJ2, KDM6B, LEMD2, LINC00694, LIPE[31 AS1, LMF2, LMLN-AS1, LPCAT4, LRCH4, LRG1, MAP3K10, MAP3K6, |

TABLE 1-continued

Sets of Genes Predictive for Due Date by Cohort

| Cohort | Predictive Genes Included in Predictive Model | Predictive Genes Not Included in Predictive Model |
|---|---|---|
| | | MAPK12, MBD6, METTL26, MGAM, MID1IP1, MIF-AS1, MME, MRPL23, NAP1L4P3, NLRP6, NPIPA5, NPIPB4, NUP58, OPRL1, PADI2, PGS1, POR, PXDN, RBKS, RNASET2, SDCBPP2, SERTAD3, SHE, SSH3, SUMO2, SUOX, SURF1, TATDN2, TFE3, TMCC3, TMEM150C, TMEM8A, TMEM94, TNFAIP6, TOR1B, UNKL, UPP1, XKR8, ZDHHC18, ZNF668 |

Figure 5C:
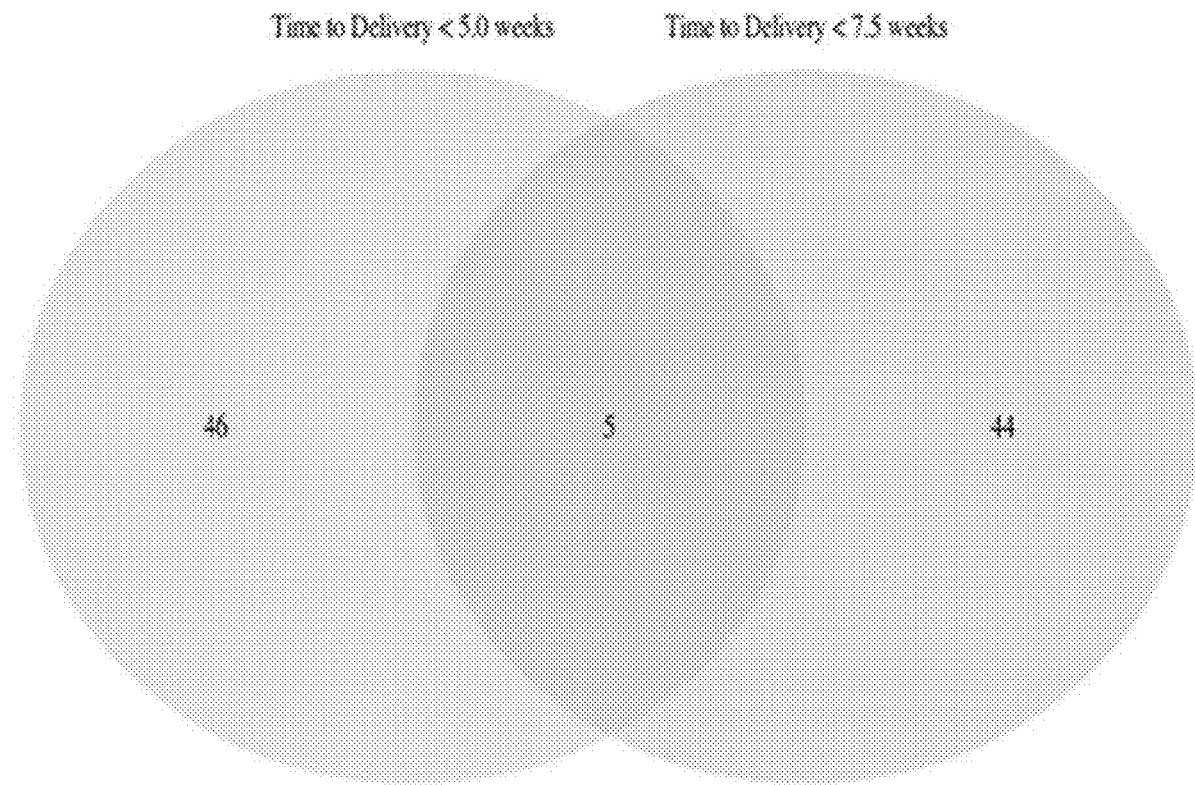
FIG. 5C is a Venn diagram showing the overlap of genes used in the first and second predictive models of due date, in accordance with disclosed embodiments. The first predictive model had a total of 51 most predictive genes, and the second predictive model had a total of 49 most predictive genes; further, only 5 genes overlapped between the two predictive models.

FIG. 5C is a Venn diagram showing the overlap of genes used in the first and second predictive models of due date. The first predictive model had a total of 51 most predictive genes, and the second predictive model had a total of 49 most predictive genes; further, only 5 genes overlapped between the two predictive models.

Figure 5D:
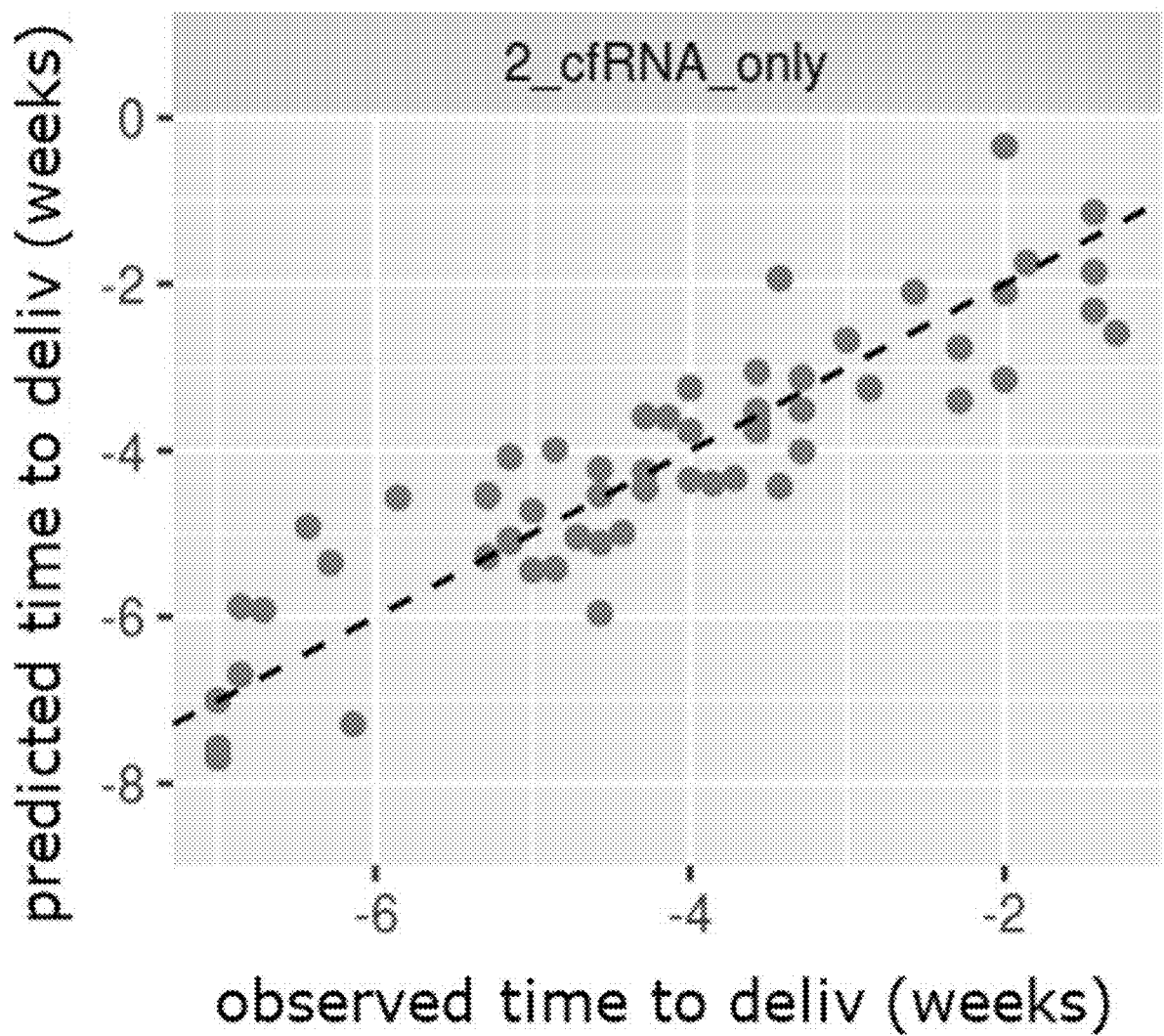
FIG. 5D is a plot showing the concordance between a predicted time to delivery (in weeks) and the observed (actual) time to delivery (in weeks) for the subjects in the due date cohort, in accordance with disclosed embodiments.

FIG. 5D is a plot showing the concordance between a predicted time to delivery (in weeks) and the observed (actual) time to delivery (in weeks) for the subjects in the due date cohort. The predicted time to delivery outcomes were generated using the respective predictive model based on the predictive genes listed in Table 1.

FIG. 5E shows a summary of the predictive models for predicting due date, including a predictive model using samples with a time-to-delivery of less than 5 weeks and predictive model using samples with a time-to-delivery of less than 7.5 weeks; different predictive models were generated with estimated due date information (e.g., determined using estimated gestational age from ultrasound measurements) and without the estimated due date information. A total of about 15,000 genes were evaluated for use in the predictive model (e.g., as part of the gene discovery process). Further, a total of 130 genes and 62 genes were identified as being predictive for due date among the "<5-week" and "<7.5-week" sample sets, respectively. A total of 28 and 47 genes were identified for inclusion in the predictive model for predicting due date without estimated due date information (e.g., from ultrasound) among the "<5-week" and "<7.5-week" sample sets, respectively. A total of 50 and 48 genes were identified for inclusion in the predictive model for predicting due date with estimated due date information (e.g., from ultrasound) among the "<5-week" and "<7.5-week" sample sets, respectively.

Example 3: Prediction of Gestational Age (GA)

Figure 6A:
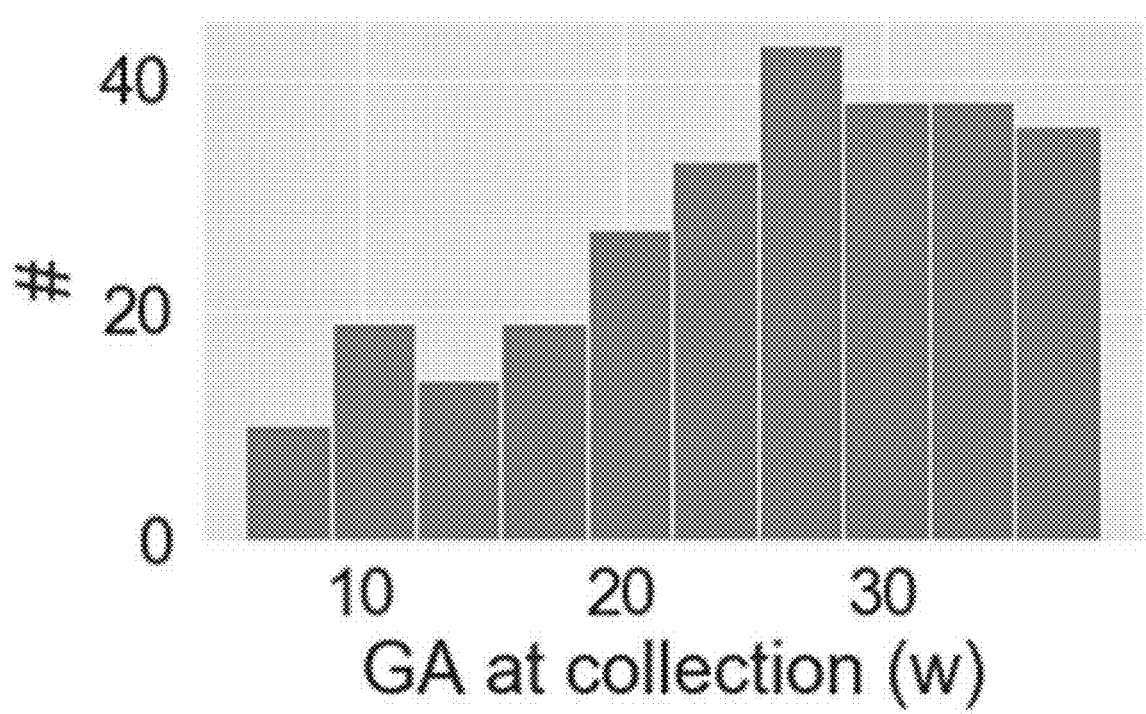
FIG. 6A shows a gestational age cohort of subjects (e.g., pregnant women) that was established (with patient identification numbers shown on the x-axis), from which one or more biological samples (e.g., 1 or 2 each) were collected and assayed at different time points corresponding to an estimated gestational age (shown on the y-axis, in increasing order of estimated gestational age at delivery) of a fetus of each subject, in accordance with disclosed embodiments.

As shown in FIG. 6A, a gestational age cohort of subjects (e.g., pregnant women) was established, from which one or more biological samples (e.g., 1 or 2 each) were collected and assayed at different time points corresponding to an estimated gestational age of a fetus of each subject, using methods and systems of the present disclosure. The gestational age cohort included subjects from the first cohort, as described in Example 1. The gestational age cohort includes subjects from whom different sample types were collected for use in different studies, including studies for the prediction of delivery, prediction of due date, and prediction of actual gestational age of a fetus of each subject.

Figure 6B:
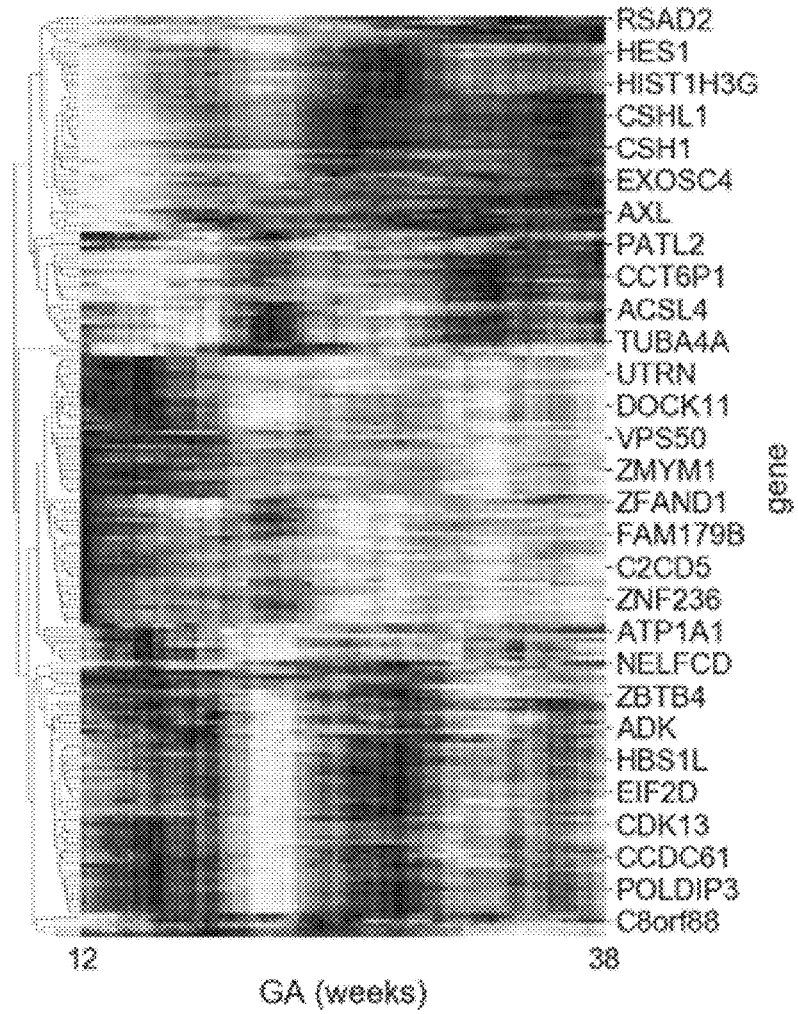
FIG. 6B is a visual model showing mutual information of the whole transcriptome, where expression of a plurality of gestational age-associated genes varies with gestational age throughout the course of a pregnancy, in accordance with disclosed embodiments.

FIG. 6B is a visual model showing mutual information of the whole transcriptome, where expression of a plurality of gestational age-associated genes varies with gestational age throughout the course of a pregnancy. As shown in the figure, different clusters of genes exhibit fluctuations (e.g., increases and decreases) during different times (e.g., at different estimated gestational ages) throughout the course of a pregnancy. For example, genes associated with innate immunity (e.g., RSAD2, HES1, HIST1H3G, CSHL1, CSH1, EXOSC4, and AXL) and genes associated with cell adhesion (e.g., PATL2, CCT6P1, ACSL4, and TUBA4A) exhibited increased expression during the latter portion of pregnancy as compared to the earlier portion of pregnancy. As another example, genes associated with cell cycle (e.g., UTRN, DOCK11, VPS50, ZMYM1, ZFAND1, FAM179B, C2CD5, and ZNF236) exhibited increased expression during the earlier portion of pregnancy as compared to the latter portion of pregnancy. As another example, genes associated with RNA processing (e.g., ZBTB4, ADK, HBS1L, EIF2D, CDK13, CCDC61, POLDIP3, and C8orf88) exhibited increased expression during the earlier and middle portions of pregnancy as compared to the latter portion of pregnancy. Therefore, different sets or clusters of genes can be assayed for use as a "molecular clock" to track and predict different gestational ages of a fetus during the course of a pregnancy. These sets of genes that are predictive for gestational age are listed in Table 2. Further, pathways that are predictive for gestational age are listed in Table 3 by cluster.

TABLE 2

Sets of Genes Predictive for Gestational Age by Cluster

| Cluster | Genes |
|---|---|
| 1 | CSHL1, CAPN6, PAPPA, LGALS14, SVEP1, VGLL3, ARMCX6, EXPH5, HDGF, HSD3B1, OSBP2, BEX1, CSH2, HIST1H2AL, HCFC1R1, AL773572.7, ACTG1, |

TABLE 2-continued

Sets of Genes Predictive for Gestational Age by Cluster

| Cluster | Genes |
|---|---|
|   | MMP8, UBE2L6, CPNE2, EFHD1, CSH1, HES1, RSAD2, RNASE3, CARD16, S100A12, NDUFS5, LRIF1, EXOSC4, CYP19A1, NXF3, STAT1, G6PC3, TACC2, HIST1H3G, BCL7B, DEFA4, OLFM4, OXTR, IF16, RDX, CAT, PLAC4, FAM207A, AXL, PGLYRP1 |
| 2 | PATL2, NAPA, PRUNE1, ST20, ATF4, FAXDC2, BEX3, ZNF117, TCEAL3, EHD3, TUBA1B, GPR180, SUCNR1, OTUD5, ACSL4, PDIA3, ZBED5-AS1, VIL1, ITM2B, TUBA4A, CECR2, RPAP3, CCT6P1, KCNMB1 |
| 3 | SCAF8, SEC24B, MYCBP2, FNDC3A, C2CD5, FRA10AC1, KIAA0368, PLOD1, ZNF44, SLC12A2, RARS, AUP1, NARS2, GON4L, RBL1, SPG11, C3orf62, VPS50, AKAP7, CEP290, WAPL, RIC1, EXOC4, UTRN, BIRC6, FASTKD1, SNRNP48, CEP128, BPTF, RLF, ZNF236, MAP4K3, DYRK1A, ZMYM1, TTC13, RNF121, REPS1, CCDC141, DOCK11, DEK, CCNL1, ATP1A1, NSD1, MIPOL1, VCAN, ZNRF2, ITSN2, EZH1, CACUL1, MIS18BP1, USP48, KMT5B, MCCC1, TBC1D32, CCDC66, ENSG00000173088, SMAD4, ATAD5, FAM179B, KPNA5, ZFAND1, CARNMT1, ZDHHC5, TASP1, PCGF6, PHIP |
| 4 | CCDC61, POLDIP3, IKBKE, SIPA1L1, NOC2L, PLEC, PLXND1, MAP2K2, HIVEP3, FAM111A, AOAH, ARHGAP30, DOCK10, FAM217B, NBPF1, HNRNPA1, DTX2, MTBP, SLC26A2, LRRK1, NFATC1, FLNB, MARCKS, BRD9, SNRPA1, TAF3, MYO1G, ZNF557, CD53, HBS1L, NFKBIE, EIF2D, PARP14, NCL, VPS18, ADK, PSMG4, IMP3, SH2D1B, CHTOP, NELFCD, PABPC1, TSHZ1, ZNF383, SDCCAG3, CDK13, TTC39C, ZBTB4, PUM2, C1orf123, GCDH, SGTA, NOL4L, LMCD1, KLHL2 |
| 5 | GABARAPL2, RAB6C, RAB6A |
| 6 | MBNL3, MYL4, C8orf88, FTLP3, RAB2B |

TABLE 3

Pathways Predictive for Gestational Age by Cluster

| Cluster | Pathway Identifier | Pathway Name | Entities p Value | Entities False Detection Rate (FDR) |
|---|---|---|---|---|
| 1 | R-HSA-909733 | Interferon alpha/beta signaling | 1.16E-04 | 0.030180579 |
| 1 | R-HSA-913531 | Interferon Signaling | 2.08E-04 | 0.030180579 |
| 1 | R-HSA-9013508 | NOTCH3 Intracellular Domain Regulates Transcription | 4.72E-04 | 0.037300063 |
| 1 | R-HSA-1280215 | Cytokine Signaling in Immune system | 5.18E-04 | 0.037300063 |
| 1 | R-HSA-196025 | Formation of annular gap junctions | 9.90E-04 | 0.056424803 |
| 1 | R-HSA-190873 | Gap junction degradation | 0.001175517 | 0.056424803 |
| 1 | R-HSA-437239 | Recycling pathway of L1 | 0.001591097 | 0.060736546 |
| 1 | R-HSA-8941856 | RUNX3 regulates NOTCH signaling | 0.002067719 | 0.060736546 |
| 1 | R-HSA-2197563 | NOTCH2 intracellular domain regulates transcription | 0.002067719 | 0.060736546 |
| 1 | R-HSA-1059683 | Interleukin-6 signaling | 0.002328072 | 0.060736546 |
| 1 | R-HSA-9012852 | Signaling by NOTCH3 | 0.002336021 | 0.060736546 |
| 1 | R-HSA-446353 | Cell-extracellular matrix interactions | 0.002892685 | 0.060737316 |
| 1 | R-HSA-196071 | Metabolism of steroid hormones | 0.003139605 | 0.060737316 |
| 1 | R-HSA-210744 | Regulation of gene expression in late stage (branching morphogenesis) pancreatic bud precursor cells | 0.003196701 | 0.060737316 |
| 1 | R-HSA-193993 | Mineralocorticoid biosynthesis | 0.003196701 | 0.060737316 |
| 1 | R-HSA-6798695 | Neutrophil degranulation | 0.003621161 | 0.065180904 |
| 1 | R-HSA-9013695 | NOTCH4 Intracellular Domain Regulates Transcription | 0.005317217 | 0.085315773 |
| 1 | R-HSA-194002 | Glucocorticoid biosynthesis | 0.005718941 | 0.085315773 |
| 1 | R-HSA193048 | Androgen biosynthesis | 0.005718941 | 0.085315773 |
| 1 | R-HSA-912694 | Regulation of IFNA signaling | 0.006134158 | 0.085315773 |
| 1 | R-HSA-982772 | Growth hormone receptor signaling | 0.006562752 | 0.085315773 |
| 1 | R-HSA-6783589 | Interleukin-6 family signaling | 0.00700461 | 0.091059924 |
| 1 | R-HSA-168256 | Immune System | 0.007818938 | 0.093827257 |
| 2 | R-HSA-8955332 | Carboxyterminal post-translational modifications of tubulin | 1.49E-04 | 0.01808342 |
| 2 | R-HSA-983231 | Factors involved in megakaryocyte development and platelet production | 5.42E-04 | 0.01808342 |
| 2 | R-HSA-190840 | Microtubule-dependent trafficking of connexons from Golgi to the plasma membrane | 8.77E-04 | 0.01808342 |
| 2 | R-HSA-190872 | Transport of connexons to the plasma membrane | 9.58E-04 | 0.01808342 |
| 2 | R-HSA-389977 | Post-chaperonin tubulin folding pathway | 0.001128943 | 0.01808342 |
| 2 | R-HSA-6811434 | COPI-dependent Golgi-to-ER retrograde traffic | 0.001205561 | 0.01808342 |

TABLE 3-continued

Pathways Predictive for Gestational Age by Cluster

| Cluster | Pathway Identifier | Pathway Name | Entities p Value | Entities False Detection Rate (FDR) |
|---|---|---|---|---|
| 2 | R-HSA-6807878 | COPI-mediated anterograde transport | 0.001205561 | 0.01808342 |
| 2 | R-HSA-389960 | Formation of tubulin folding intermediates by CCT/TriC | 0.001615847 | 0.022621853 |
| 2 | R-HSA-9619483 | Activation of AMPK downstream of NMDARs | 0.002065423 | 0.024371102 |
| 2 | R-HSA-5626467 | RHO GTPases activate IQGAPs | 0.002309953 | 0.024371102 |
| 2 | R-HSA-389958 | Cooperation of Prefoldin and TriC/CCT in actin and tubulin folding | 0.00243711 | 0.024371102 |
| 2 | R-HSA-190861 | Gap junction assembly | 0.002978066 | 0.024970608 |
| 2 | R-HSA-8856688 | Golgi-to-ER retrograde transport | 0.003023387 | 0.024970608 |
| 2 | R-HSA-381042 | PERK regulates gene expression | 0.003121326 | 0.024970608 |
| 2 | R-HSA-199977 | ER to Golgi Anterograde Transport | 0.004028523 | 0.027278879 |
| 2 | R-HSA-9609736 | Assembly and cell surface presentation of NMDA receptors | 0.004047319 | 0.027278879 |
| 2 | R-HSA-190828 | Gap junction trafficking | 0.004727036 | 0.027278879 |
| 2 | R-HSA-437239 | Recycling pathway of L1 | 0.005269036 | 0.027278879 |
| 2 | R-HSA-5620924 | Intraflagellar transport | 0.005455776 | 0.027278879 |
| 2 | R-HSA-157858 | Gap junction trafficking and regulation | 0.005455776 | 0.027278879 |
| 2 | R-HSA-6811436 | COPI-independent Golgi-to-ER retrograde traffic | 0.006846767 | 0.034233833 |
| 2 | R-HSA-983189 | Kinesins | 0.00792863 | 0.03517302 |
| 2 | R-HSA-3371497 | HSP90 chaperone cycle for steroid hormone receptors (SHR) | 0.008381604 | 0.03517302 |
| 2 | R-HSA-6811442 | Intra-Golgi and retrograde Golgi-to-ER traffic | 0.008817252 | 0.03517302 |
| 2 | R-HSA-446203 | Asparagine N-linked glycosylation | 0.00885181 | 0.03517302 |
| 2 | R-HSA-948021 | Transport to the Golgi and subsequent modification | 0.008927485 | 0.03517302 |
| 2 | R-HSA-1445148 | Translocation of SLC2A4 (GLUT4) to the plasma membrane | 0.010560059 | 0.03517302 |
| 2 | R-HSA-392499 | Metabolism of proteins | 0.0111176 | 0.03517302 |
| 2 | R-HSA-8852276 | The role of GTSE1 in G2/M progression after G2 checkpoint | 0.011600388 | 0.03517302 |
| 2 | R-HSA-205025 | NADE modulates death signalling | 0.01172434 | 0.03517302 |
| 2 | R-HSA-438064 | Post NMDA receptor activation events | 0.01527754 | 0.045832619 |
| 2 | R-HSA-380320 | Recruitment of NuMA to mitotic centrosomes | 0.015578704 | 0.046736112 |
| 2 | R-HSA-390466 | Chaperonin-mediated protein folding | 0.016497529 | 0.049492587 |
| 2 | R-HSA-434313 | Intracellular metabolism of fatty acids regulates insulin secretion | 0.017536692 | 0.052610075 |
| 2 | R-HSA-391251 | Protein folding | 0.018403238 | 0.055209713 |
| 2 | R-HSA-1296052 | Ca2+ activated K+ channels | 0.019466807 | 0.056873842 |
| 2 | R-HSA-109582 | Hemostasis | 0.020531826 | 0.056873842 |
| 2 | R-HSA-442755 | Activation of NMDA receptors and postsynaptic events | 0.020738762 | 0.056873842 |
| 2 | R-HSA-5610787 | Hedgehog 'off' state | 0.024645005 | 0.056873842 |
| 2 | R-HSA-373760 | L1CAM interactions | 0.026893295 | 0.056873842 |
| 2 | R-HSA-2500257 | Resolution of Sister Chromatid Cohesion | 0.028436921 | 0.056873842 |
| 2 | R-HSA-381183 | ATF6 (ATF6-alpha) activates chaperone genes | 0.029062665 | 0.05812533 |
| 2 | R-HSA-381033 | ATF6 (ATF6-alpha) activates chaperones | 0.032875598 | 0.065751195 |
| 2 | R-HSA-2132295 | MHC class II antigen presentation | 0.034112102 | 0.068224205 |
| 2 | R-HSA-5663220 | RHO GTPases Activate Formins | 0.034533251 | 0.069066501 |
| 2 | R-HSA-418457 | cGMP effects | 0.034776645 | 0.069553291 |
| 2 | R-HSA-381119 | Unfolded Protein Response (UPR) | 0.037102976 | 0.074205952 |
| 2 | R-HSA-5358351 | Signaling by Hedgehog | 0.042915289 | 0.077519335 |
| 2 | R-HSA-400451 | Free fatty acids regulate insulin secretion | 0.051724699 | 0.077519335 |
| 2 | R-HSA-389957 | Prefoldin mediated transfer of substrate to CCT/TriC | 0.055451773 | 0.077519335 |
| 2 | R-HSA-2467813 | Separation of Sister Chromatids | 0.055478287 | 0.077519335 |
| 2 | R-HSA-68877 | Mitotic Prometaphase | 0.062192558 | 0.077519335 |
| 2 | R-HSA-5617833 | Cilium Assembly | 0.062720246 | 0.077519335 |
| 2 | R-HSA-68882 | Mitotic Anaphase | 0.062720246 | 0.077519335 |
| 2 | R-HSA-2555396 | Mitotic Metaphase and Anaphase | 0.064312651 | 0.077519335 |
| 2 | R-HSA-380994 | ATF4 activates genes in response to endoplasmic reticulum stress | 0.064707762 | 0.077519335 |
| 2 | R-HSA-69275 | G2/M Transition | 0.064846542 | 0.077519335 |
| 2 | R-HSA-453274 | Mitotic G2-G2/M phases | 0.06591891 | 0.077519335 |
| 2 | R-HSA-936440 | Negative regulators of DDX58/IFIH1 signaling | 0.068385614 | 0.077519335 |
| 2 | R-HSA-112316 | Neuronal System | 0.07344898 | 0.077519335 |
| 2 | R-HSA-112314 | Neurotransmitter receptors and postsynaptic signal transmission | 0.075836046 | 0.077519335 |

TABLE 3-continued

Pathways Predictive for Gestational Age by Cluster

| Cluster | Pathway Identifier | Pathway Name | Entities p Value | Entities False Detection Rate (FDR) |
|---|---|---|---|---|
| 2 | R-HSA-901042 | Calnexin/calreticulin cycle | 0.077519335 | 0.077519335 |
| 2 | R-HSA-392154 | Nitric oxide stimulates guanylate cyclase | 0.077519335 | 0.077519335 |
| 2 | R-HSA-5689896 | Ovarian tumor domain proteases | 0.081148593 | 0.081148593 |
| 2 | R-HSA-597592 | Post-translational protein modification | 0.085097153 | 0.085097153 |
| 2 | R-HSA-6811438 | Intra-Golgi traffic | 0.090161601 | 0.090161601 |
| 2 | R-HSA-75876 | Synthesis of very long-chain fatty acyl-CoAs | 0.095528421 | 0.095528421 |
| 2 | R-HSA-5683826 | Surfactant metabolism | 0.099089328 | 0.099089328 |
| 3 | R-HSA-1538133 | G0 and Early G1 | 8.71E−04 | 0.206527784 |
| 3 | R-HSA-1362277 | Transcription of E2F targets under negative control by DREAM complex | 0.006680493 | 0.291565226 |
| 3 | R-HSA-453279 | Mitotic G1-G1/S phases | 0.010050075 | 0.291565226 |
| 3 | R-HSA-3304347 | Loss of Function of SMAD4 in Cancer | 0.014424835 | 0.291565226 |
| 3 | R-HSA-3311021 | SMAD4 MH2 Domain Mutants in Cancer | 0.014424835 | 0.291565226 |
| 3 | R-HSA-3315487 | SMAD2/3 MH2 Domain Mutants in Cancer | 0.014424835 | 0.291565226 |
| 3 | R-HSA-2173796 | SMAD2/SMAD3:SMAD4 heterotrimer regulates transcription | 0.015567079 | 0.291565226 |
| 3 | R-HSA-3214841 | PKMTs methylate histone lysines | 0.023826643 | 0.291565226 |
| 3 | R-HSA-8952158 | RUNX3 regulates BCL2L11 (BIM) transcription | 0.028644567 | 0.291565226 |
| 3 | R-HSA-2173793 | Transcriptional activity of SMAD2/SMAD3:SMAD4 heterotrimer | 0.029469648 | 0.291565226 |
| 3 | R-HSA-8941855 | RUNX3 regulates CDKN1A transcription | 0.038011863 | 0.291565226 |
| 3 | R-HSA-3304349 | Loss of Function of SMAD2/3 in Cancer | 0.038011863 | 0.291565226 |
| 3 | R-HSA-444821 | Relaxin receptors | 0.038011863 | 0.291565226 |
| 3 | R-HSA-9645135 | STAT5 Activation | 0.04266207 | 0.291565226 |
| 3 | R-HSA-3595174 | Defective CHST14 causes EDS, musculocontractural type | 0.04266207 | 0.291565226 |
| 3 | R-HSA-3595172 | Defective CHST3 causes SEDCJD | 0.04266207 | 0.291565226 |
| 3 | R-HSA-3304351 | Signaling by TGF-beta Receptor Complex in Cancer | 0.04266207 | 0.291565226 |
| 3 | R-HSA-379724 | tRNA Aminoacylation | 0.043286108 | 0.291565226 |
| 3 | R-HSA-1640170 | Cell Cycle | 0.04679213 | 0.291565226 |
| 3 | R-HSA-3595177 | Defective CHSY1 causes TPBS | 0.047290122 | 0.291565226 |
| 3 | R-HSA-2470946 | Cohesin Loading onto Chromatin | 0.047290122 | 0.291565226 |
| 3 | R-HSA-426117 | Cation-coupled Chloride cotransporters | 0.047290122 | 0.291565226 |
| 3 | R-HSA-3371599 | Defective HLCS causes multiple carboxylase deficiency | 0.047290122 | 0.291565226 |
| 3 | R-HSA-351906 | Apoptotic cleavage of cell adhesion proteins | 0.051896124 | 0.291565226 |
| 3 | R-HSA-176974 | Unwinding of DNA | 0.056480178 | 0.291565226 |
| 3 | R-HSA-3323169 | Defects in biotin (Btn) metabolism | 0.056480178 | 0.291565226 |
| 3 | R-HSA-1445148 | Translocation of SLC2A4 (GLUT4) to the plasma membrane | 0.056493106 | 0.291565226 |
| 3 | R-HSA-69278 | Cell Cycle, Mitotic | 0.057847859 | 0.291565226 |
| 3 | R-HSA-2022923 | Dermatan sulfate biosynthesis | 0.061042388 | 0.291565226 |
| 3 | R-HSA-2468052 | Establishment of Sister Chromatid Cohesion | 0.061042388 | 0.291565226 |
| 3 | R-HSA-170834 | Signaling by TGF-beta Receptor Complex | 0.064216491 | 0.291565226 |
| 3 | R-HSA-68884 | Mitotic Telophase/Cytokinesis | 0.070101686 | 0.291565226 |
| 3 | R-HSA-1502540 | Signaling by Activin | 0.070101686 | 0.291565226 |
| 3 | R-HSA-8983432 | Interleukin-15 signaling | 0.074598978 | 0.291565226 |
| 3 | R-HSA-196780 | Biotin transport and metabolism | 0.087962635 | 0.291565226 |
| 3 | R-HSA-1362300 | Transcription of E2F targets under negative control by p107 (RBL1) and p130 (RBL2) in complex with HDAC1 | 0.092374782 | 0.291565226 |
| 3 | R-HSA-3560783 | Defective B4GALT7 causes EDS, progeroid type | 0.096765893 | 0.291565226 |
| 3 | R-HSA-4420332 | Defective B3GALT6 causes EDSP2 and SEMDJL1 | 0.096765893 | 0.291565226 |
| 3 | R-HSA-6804114 | TP53 Regulates Transcription of Genes Involved in G2 Cell Cycle Arrest | 0.096765893 | 0.291565226 |
| 4 | R-HSA-8953854 | Metabolism of RNA | 0.008040167 | 0.222786123 |
| 4 | R-HSA-9013508 | NOTCH3 Intracellular Domain Regulates Transcription | 0.011600797 | 0.222786123 |
| 4 | R-HSA-3304347 | Loss of Function of SMAD4 in Cancer | 0.013386586 | 0.222786123 |
| 4 | R-HSA-3560792 | Defective 5LC26A2 causes chondrodysplasias | 0.013386586 | 0.222786123 |
| 4 | R-HSA-3311021 | SMAD4 MH2 Domain Mutants in Cancer | 0.013386586 | 0.222786123 |
| 4 | R-HSA-3315487 | SMAD2/3 MH2 Domain Mutants in Cancer | 0.013386586 | 0.222786123 |

TABLE 3-continued

Pathways Predictive for Gestational Age by Cluster

| Cluster | Pathway Identifier | Pathway Name | Entities p Value | Entities False Detection Rate (FDR) |
|---|---|---|---|---|
| 4 | R-HSA-73857 | RNA Polymerase II Transcription | 0.014524942 | 0.222786123 |
| 4 | R-HSA-8952158 | RUNX3 regulates BCL2L11 (BIM) transcription | 0.026596735 | 0.222786123 |
| 4 | R-HSA-72203 | Processing of Capped Intron-Containing Pre-mRNA | 0.028244596 | 0.222786123 |
| 4 | R-HSA-72187 | mRNA 3'-end processing | 0.028277064 | 0.222786123 |
| 4 | R-HSA-74160 | Gene expression (Transcription) | 0.02961978 | 0.222786123 |
| 4 | R-HSA-9012852 | Signaling by NOTCH3 | 0.032891337 | 0.222786123 |

Figure 6C:
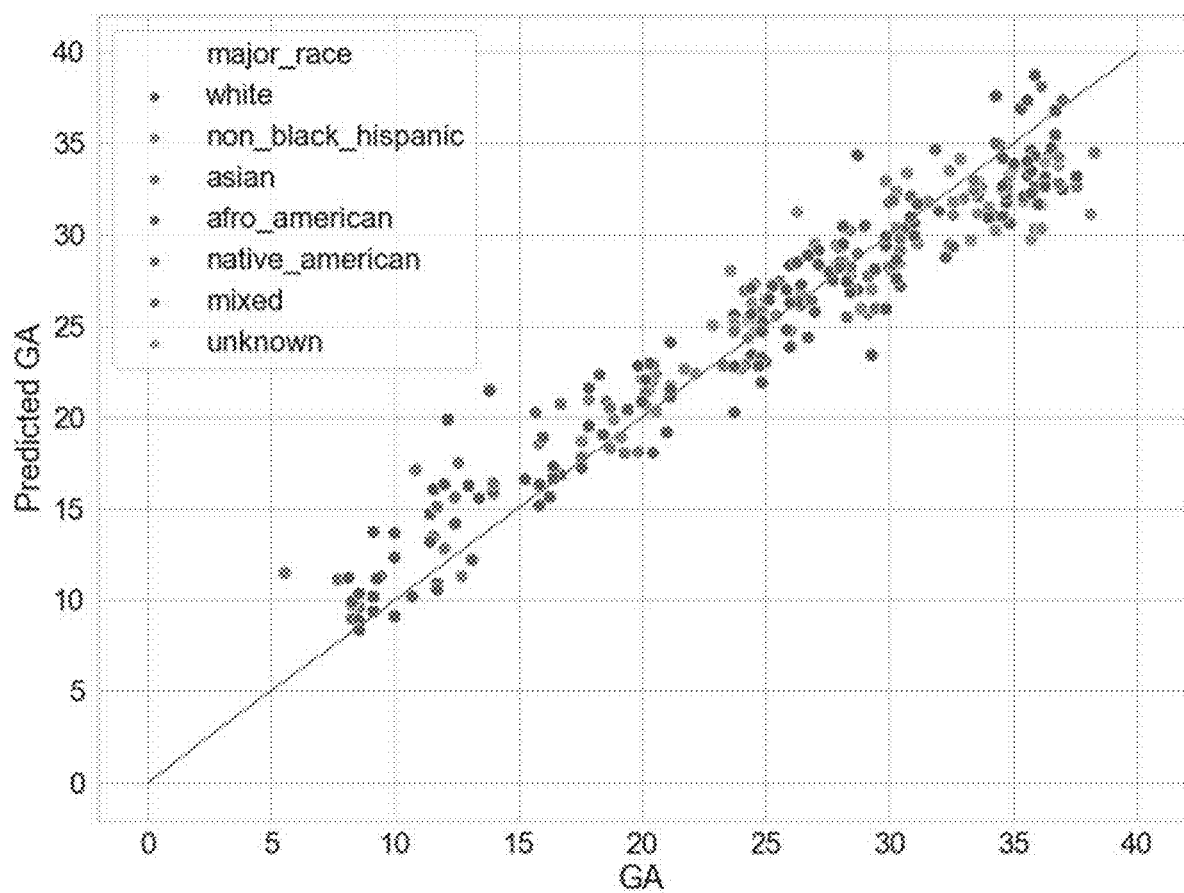
FIG. 6C is a plot showing the concordance between a predicted gestational age (in weeks) and the measured gestational age (in weeks) for the subjects in the gestational age cohort, in accordance with disclosed embodiments. The subjects are stratified in the plot by major race (e.g., white, non-black Hispanic, Asian, Afro-American, Native American, mixed race (e.g., two or more races), or unknown).

FIG. 6C is a plot showing the concordance between a predicted gestational age (in weeks) and the measured gestational age (in weeks) for the subjects in the gestational age cohort. The subjects are stratified in the plot by major race (e.g., white, non-black Hispanic, Asian, Afro-American, Native American, mixed race (e.g., two or more races), or unknown). It is noteworthy that the data shows that, unlike many biological phenotypes, the gestational biomarkers model (e.g., prediction of gestational age based on a set of gestational age-associated biomarker genes) is independent of race or ethnicity. This observation indicates that the underlying molecular clock of pregnancy is highly conserved across races/ethnicities, which has a practical implication of making a universal assay for gestational age feasible. The predicted gestational ages were generated using a predictive model for gestational age (a Lasso model generating with a 10-fold cross-validation) based on the predictive genes listed in Table 2 and/or the predictive pathways listed in Table 3. Further, the predictive model weights of genes that are predictive for gestational age are listed in Table 4.

TABLE 4

Predictive Model Weights of Genes Predictive for Gestational Age

| Gene | Weight |
|---|---|
| CGA | −2.3291809 |
| CSH1 | 2.0997422 |
| CAPN6 | 1.58718823 |
| UBE2L6 | 0.78006933 |
| CYP19A1 | 0.7495651 |
| MCEMP1 | 0.66188425 |
| STAT1 | 0.62796009 |
| ANGPT2 | −0.61766869 |
| SUCNR1 | 0.60439183 |
| EXPH5 | 0.55503889 |
| LRMP | −0.53240046 |
| RGS9 | 0.43352062 |
| NXF3 | 0.40263822 |
| DDI2 | −0.39475793 |
| PPP2CB | −0.34436392 |
| BBX | 0.34034586 |
| FCGR2A | 0.33904027 |
| NREP | 0.33265012 |
| BEX1 | 0.27078087 |
| RYR3 | −0.25427064 |
| IGHA1 | −0.24225842 |
| IL18BP | −0.22511377 |
| SLC7A11 | 0.21310441 |
| TCHH | 0.2115899 |
| SMAD5 | −0.19126152 |
| FAM114A1 | −0.18288572 |
| CCDC66 | −0.18079341 |
| PLS3 | −0.17781532 |

TABLE 4-continued

Predictive Model Weights of Genes Predictive for Gestational Age

| Gene | Weight |
|---|---|
| BCAT1 | 0.17680457 |
| RECQL | 0.17503129 |
| CD96 | 0.15741167 |
| FAM214A | −0.15229302 |
| GCNT1 | 0.14693661 |
| DCAF17 | −0.14675868 |
| HIST1H2BB | 0.1407058 |
| CCT6B | 0.13180261 |
| FBXL20 | −0.12456705 |
| H19 | −0.12185332 |
| SKIL | 0.11799157 |
| ABCB10 | 0.11737993 |
| FARS2 | 0.11728322 |
| SERPINB10 | 0.11535642 |
| MCCC1 | −0.10689218 |
| FTH1P7 | 0.10503966 |
| SLC4A7 | −0.10328859 |
| TCN1 | 0.10244934 |
| ARHGAP42 | −0.10056675 |
| RAC1 | 0.09965553 |
| EED | −0.09795522 |
| RAB8B | 0.09392322 |
| SOX12 | −0.09281749 |
| UBE2G1 | −0.09063966 |
| CFAP70 | −0.09009795 |
| SPA17 | 0.08878255 |
| RASAL2 | −0.08386265 |
| RHAG | 0.07777724 |
| NQO2 | 0.07671752 |
| NKAPL | 0.07183955 |
| SORBS2 | 0.07127603 |
| BTRC | −0.07061876 |
| LAMTOR3 | 0.06135476 |
| RDX | 0.06114729 |
| APOL4 | 0.06043051 |
| SVEP1 | 0.06015624 |
| IGHV3-23 | −0.05726866 |
| PPCS | 0.05506125 |
| TNIP3 | 0.05448006 |
| WDSUB1 | −0.05228332 |
| TMEM14A | 0.0522635 |
| SEMA3C | 0.05196743 |
| SUZ12 | −0.04935669 |
| GATSL2 | −0.0426659 |
| TMEM109 | 0.03944985 |
| CPNE2 | 0.03713674 |
| REEP5 | 0.03492848 |
| GCSAML | 0.03481997 |
| LYRM9 | 0.03446721 |
| CENPV | −0.03301296 |
| NEK6 | 0.03186441 |
| PET100 | −0.03081952 |
| FAM221A | −0.0293719 |
| ZDHHC8 | −0.02866679 |
| IGSF21 | 0.02810308 |

TABLE 4-continued

Predictive Model Weights of Genes Predictive for Gestational Age

| Gene | Weight |
|---|---|
| FAM63B | −0.0259032 |
| HABP4 | −0.02585663 |
| LEMD3 | −0.01949602 |
| WDR27 | −0.01899405 |
| AXL | 0.01873862 |
| SMARCA1 | 0.01789833 |
| GNPAT | 0.01659611 |
| IGHV3-7 | −0.01587266 |
| DYNC2LI1 | −0.01543354 |
| PROS2P | 0.01216718 |
| ATP9A | 0.01210078 |
| HBEGF | −0.01123074 |
| COMT | 0.01102531 |
| DYNLT3 | 0.00555317 |
| TBC1D32 | −0.00434216 |
| MYL12B | 0.0037807 |

Example 4: Prediction of Pre-Term Birth (PTB)

Figure 7A:
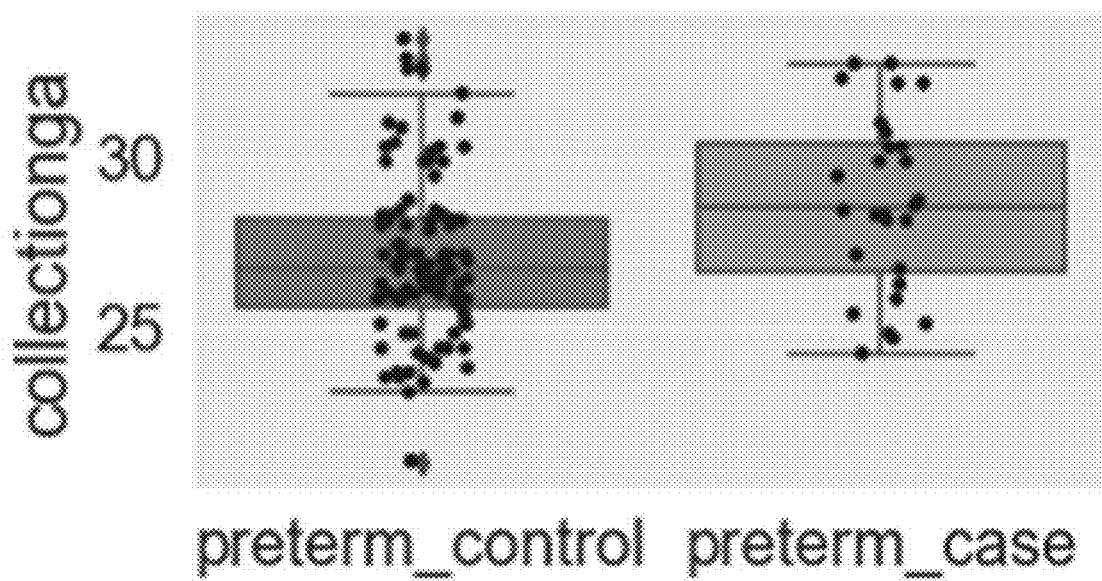
FIGS. 7A-7B show results for a pre-term birth (PTB) cohort of subjects (e.g., pregnant women), which included a set of pre-term case samples (e.g., from women having pre-term births) and a set of pre-term control samples (e.g., from women having full-term births), in accordance with disclosed embodiments. Across the pre-term case samples and pre-term control samples, the distributions of gestational age at time of collection were similar (FIG. 7A), while the distributions of gestational age at delivery were clearly distinguishable to a statistically significant extent (FIG. 7B).
Figure 7B:
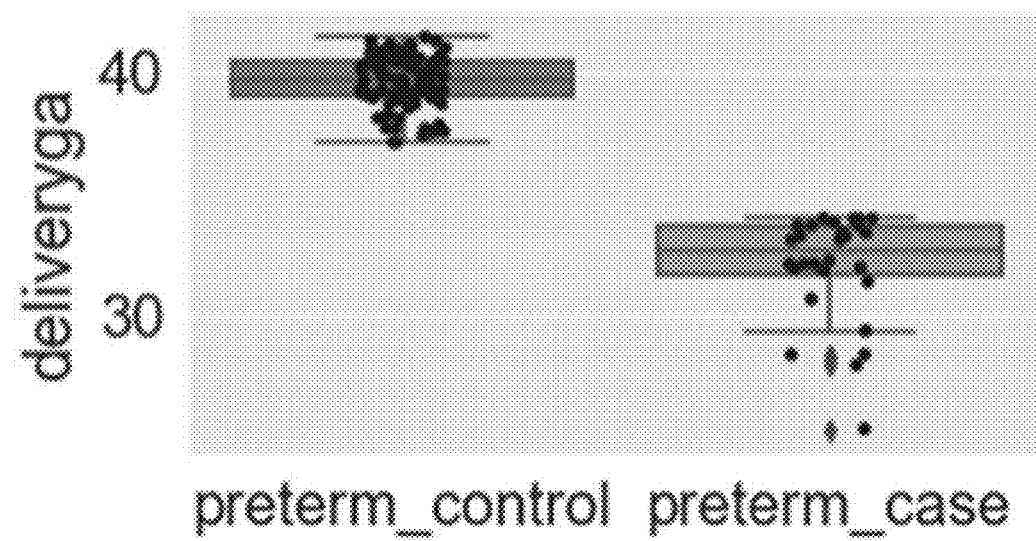

As shown in FIGS. 7A-7B, a pre-term birth (PTB) cohort of subjects (e.g., pregnant women) was established, from which one or more biological samples (e.g., 1, 2, 3, or more than 3 each) were collected and assayed at different time points corresponding to an estimated gestational age of a fetus of each subject, using methods and systems of the present disclosure. The pre-term birth cohort included subjects from the second cohort, as described in Example 1. The pre-term birth cohort includes subjects from whom different sample types were collected for use in different studies, including studies for the prediction of pre-term birth, prediction of delivery, prediction of due date, and prediction of actual gestational age of a fetus of each subject. As shown in the figure, a total of 160 samples from 128 pregnant subjects of the pre-term birth cohort were collected and assayed, of which 118 samples were collected from 100 pregnant subjects having full-term births and 42 samples were collected from 28 pregnant subjects having pre-term births (e.g., defined as occurring before an estimated gestational age of 37 weeks). The pre-term birth (PTB) cohort included a set of pre-term case samples (e.g., from women having pre-term births) and a set of pre-term control samples (e.g., from women having full-term births). Across the pre-term case samples and pre-term control samples, the distributions of gestational age at time of collection were similar (FIG. 7A), while the distributions of gestational age at delivery were clearly distinguishable to a statistically significant extent (FIG. 7B).

Figure 7C:
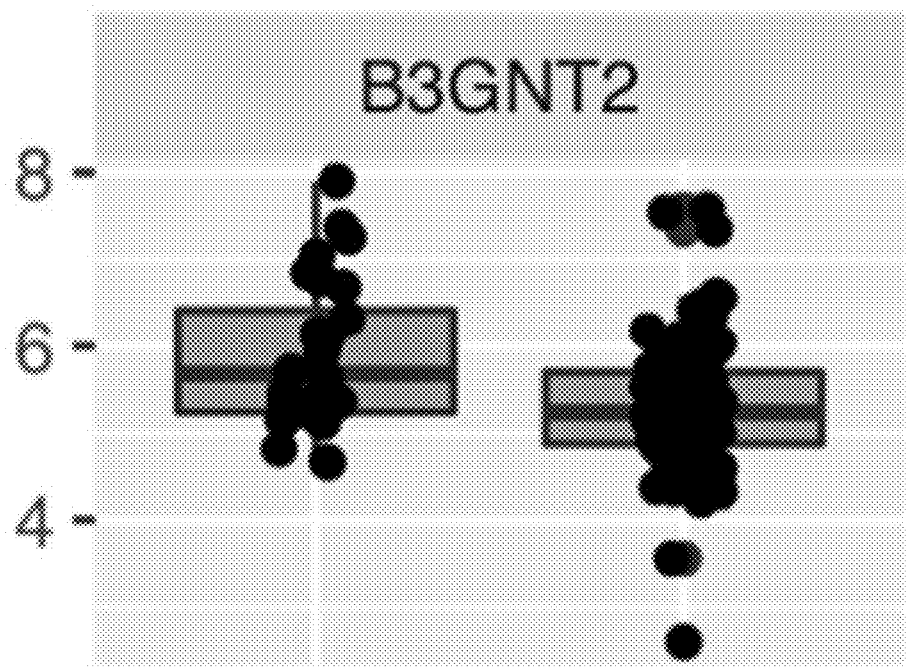
FIGS. 7C-7E show differential gene expression of the B3GNT2, BPI, and ELANE genes, respectively, between the pre-term case samples (left) and pre-term control samples (right), in accordance with disclosed embodiments.
Figure 7D:
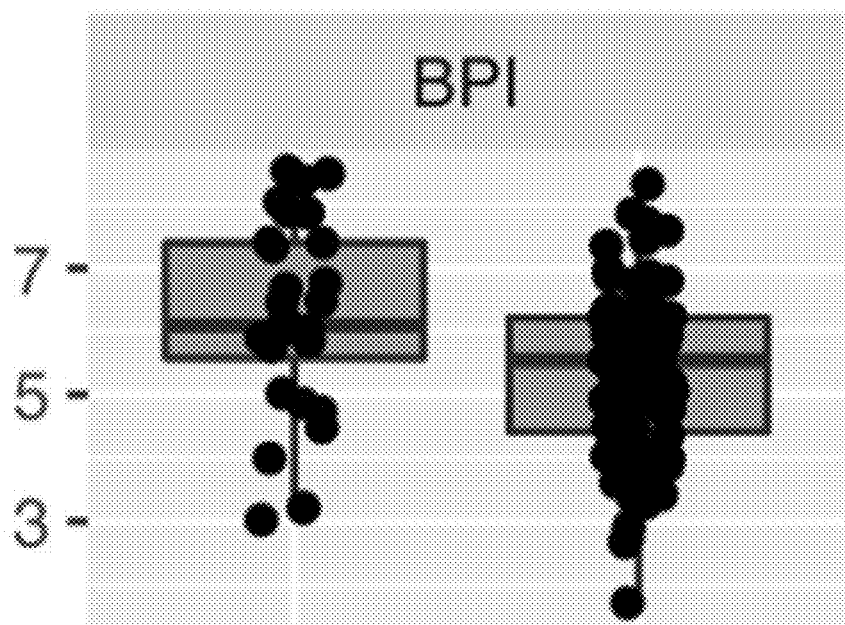
Figure 7E:
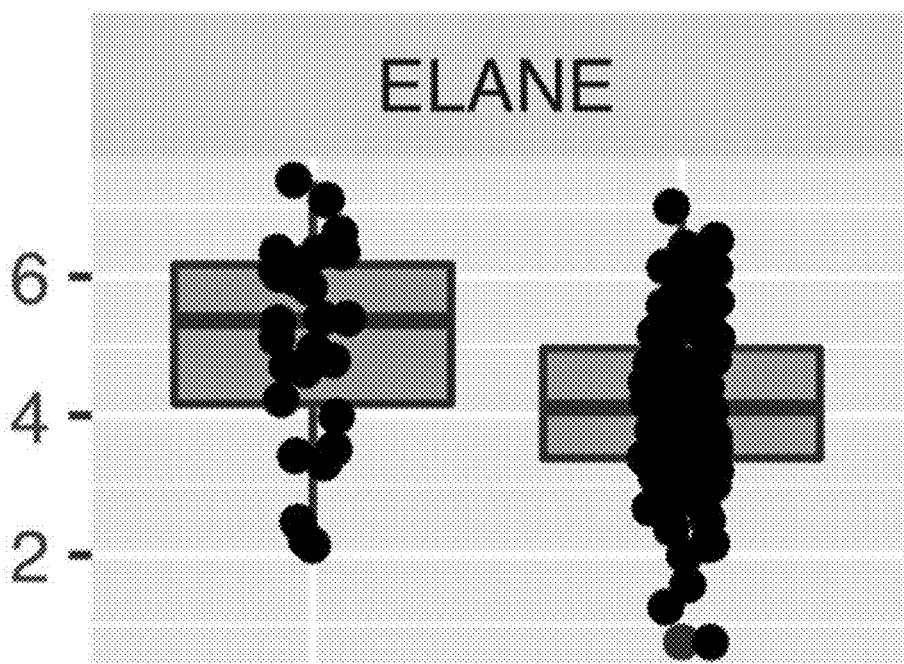
Figure 7F:
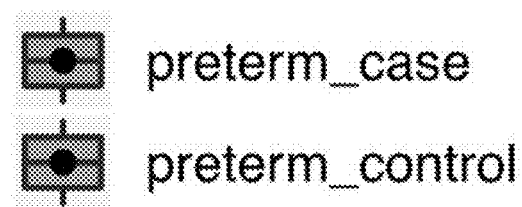
FIG. 7F shows a legend for the results from pre-term case samples and pre-term control samples shown in FIGS. 7C-7E, in accordance with disclosed embodiments.

An analysis for differentially expressed genes between the pre-term case samples and pre-term control samples was performed, revealing that 151 genes were unregulated and 37 genes were downregulated. For example, FIGS. 7C-7E show differential gene expression of the B3GNT2, BPI, and ELANE genes, respectively, between the pre-term case samples (left) and pre-term control samples (right). FIG. 7F shows a legend for the results from pre-term case samples and pre-term control samples shown in FIGS. 7C-7E. A set of genes that are predictive for pre-term birth (PTB) are listed in Table 5. Further, the predictive model weights of genes that are predictive for pre-term birth (PTB) are listed in Table 6.

TABLE 5

Set of Genes Predictive for Pre-Term Birth (PTB)

| Gene | BaseMean | Log2FoldChange | lfcSE | Stat | P Value | P_adj |
|---|---|---|---|---|---|---|
| MKI67 | 400.830667 | −0.601319668 | 0.108179231 | 32.84474216 | 9.98207E-09 | 9.05274E-05 |
| TPX2 | 65.5033344 | −0.581186144 | 0.110641746 | 29.0631565 | 7.00567E-08 | 0.000317672 |
| B3GNT2 | 50.6724879 | −0.811226454 | 0.166164856 | 24.85992629 | 6.16508E-07 | 0.001863703 |
| TOP2A | 216.98909 | −0.405447156 | 0.086617399 | 22.58819561 | 2.00714E-06 | 0.004550689 |
| CFAP45 | 124.955577 | −0.775232315 | 0.16837313 | 21.97718654 | 2.75911E-06 | 0.005004467 |
| RABEP1 | 589.967939 | 0.172443456 | 0.037329151 | 21.04101979 | 4.49555E-06 | 0.00502318 |
| SPAG5 | 23.1133858 | −0.653772557 | 0.145799452 | 20.86325357 | 4.93267E-06 | 0.00502318 |
| MRVI1 | 124.226298 | −0.680912281 | 0.155527024 | 20.7857985 | 5.13624E-06 | 0.00502318 |
| HIST1H2BB | 67.0856736 | −0.621390031 | 0.142395396 | 20.78222285 | 5.14584E-06 | 0.00502318 |
| IRX3 | 24.1768218 | −1.212908431 | 0.274268915 | 20.64129438 | 5.53885E-06 | 0.00502318 |
| PRC1 | 93.5892327 | −0.3611091 | 0.081976316 | 19.92418748 | 8.05745E-06 | 0.006094756 |
| ACSM3 | 27.2003648 | −0.716459154 | 0.161223045 | 19.92251129 | 8.06451E-06 | 0.006094756 |
| LTF | 95.8462149 | −1.197283648 | 0.285286547 | 19.21981298 | 1.16498E-05 | 0.008127079 |
| CLSPN | 101.400363 | −0.379383578 | 0.088756166 | 18.72100697 | 1.51306E-05 | 0.009801412 |
| ABCA13 | 28.4998585 | −1.147381421 | 0.276646667 | 18.52138019 | 1.68009E-05 | 0.009992992 |
| DAP3 | 276.946453 | 0.200259669 | 0.046325618 | 18.38293849 | 1.80668E-05 | 0.009992992 |
| CLPX | 260.222378 | 0.208245562 | 0.048240765 | 18.31405149 | 1.8732E-05 | 0.009992992 |
| PRDM4 | 73.7117025 | −0.280318521 | 0.068189159 | 17.43554082 | 2.97216E-05 | 0.014220995 |
| HJURP | 49.7967158 | −0.48470193 | 0.118013732 | 17.43093908 | 2.97937E-05 | 0.014220995 |
| CEACAM8 | 40.6294185 | −1.167910698 | 0.291855251 | 17.00860876 | 3.72107E-05 | 0.016873202 |
| WDR43 | 162.21835 | 0.201833504 | 0.048851646 | 16.90058186 | 3.93895E-05 | 0.01701064 |
| PHGDH | 64.6602039 | −1.038524899 | 0.272984761 | 16.10479806 | 5.9932E-05 | 0.024705606 |
| SPRY1 | 18.6318178 | −0.739453446 | 0.191408208 | 15.96857116 | 6.44028E-05 | 0.025394321 |
| COQ2 | 32.7210234 | −0.494334868 | 0.129086701 | 15.47489359 | 8.36084E-05 | 0.031168137 |
| SGO2 | 79.0913883 | −0.278147351 | 0.071596767 | 15.42336324 | 8.59194E-05 | 0.031168137 |
| FBN1 | 18.0266461 | −0.786173751 | 0.199134531 | 15.16720482 | 9.83976E-05 | 0.034321842 |
| GPSM2 | 63.6368478 | −0.305850326 | 0.079647479 | 15.04158139 | 0.000105168 | 0.034781625 |
| WASL | 69.0262558 | −0.314359854 | 0.082595598 | 15.00219484 | 0.000107386 | 0.034781625 |
| C10orf88 | 34.4590779 | −0.561281119 | 0.150387991 | 14.86051191 | 0.000115761 | 0.036201295 |
| MAPK10 | 62.7246279 | −0.787771018 | 0.214606489 | 14.75561567 | 0.000122382 | 0.036996225 |
| SDAD1 | 119.719558 | 0.323236991 | 0.083187212 | 14.62160832 | 0.000131399 | 0.038440635 |
| AP1AR | 52.9450923 | 0.296319236 | 0.07703744 | 14.44196908 | 0.000144545 | 0.039709576 |
| CEACAM6 | 17.6472741 | −1.040919908 | 0.28533353 | 14.37541601 | 0.000149745 | 0.039709576 |
| VPS9D1 | 31.4783536 | −0.64593929 | 0.173835235 | 14.35682089 | 0.000151231 | 0.039709576 |
| MEAF6 | 181.85469 | 0.234732787 | 0.061260932 | 14.3070259 | 0.000155284 | 0.039709576 |

TABLE 5-continued

Set of Genes Predictive for Pre-Term Birth (PTB)

| Gene | BaseMean | Log2FoldChange | lfcSE | Stat | P Value | P_adj |
|---|---|---|---|---|---|---|
| FOXM1 | 20.5441036 | −0.636516603 | 0.171727594 | 14.23388904 | 0.000161437 | 0.039709576 |
| SHCBP1 | 21.3472375 | −0.459928249 | 0.124085932 | 14.22723861 | 0.000162008 | 0.039709576 |
| CIT | 124.514777 | −0.328433636 | 0.088967509 | 13.99039883 | 0.000183747 | 0.043852559 |
| ACADVL | 137.011451 | −0.430868422 | 0.117813378 | 13.82728288 | 0.000200405 | 0.044288458 |
| BCORL1 | 111.923293 | −0.402393529 | 0.109550057 | 13.80336562 | 0.000202972 | 0.044288458 |
| HIST1H3F | 33.0009859 | −0.537748862 | 0.147682317 | 13.79931363 | 0.000203411 | 0.044288458 |
| ERI2 | 29.8917001 | −0.429671723 | 0.11865343 | 13.70904243 | 0.000213424 | 0.044288458 |
| ASPM | 108.467082 | −0.303317686 | 0.083048184 | 13.6994066 | 0.000214522 | 0.044288458 |
| LATS2 | 72.1128433 | −0.43419763 | 0.120730726 | 13.61286351 | 0.000224641 | 0.044288458 |
| P4HB | 308.144977 | −0.467363453 | 0.130617695 | 13.59109153 | 0.000227261 | 0.044288458 |
| RRM2 | 57.4816431 | −0.639528628 | 0.178697012 | 13.55808795 | 0.000231293 | 0.044288458 |
| HIST1H2AH | 39.7276884 | −0.738920384 | 0.209333866 | 13.55131997 | 0.000232128 | 0.044288458 |
| TBC1D7 | 20.8101265 | −0.491912362 | 0.137149751 | 13.53297652 | 0.000234408 | 0.044288458 |
| ZSCAN29 | 85.830534 | −0.403022474 | 0.113370078 | 13.47259044 | 0.000242074 | 0.044803426 |
| MRTO4 | 16.8779413 | 0.691948182 | 0.183119079 | 13.42031428 | 0.000248914 | 0.04514802 |
| ELANE | 29.9488832 | −0.86703039 | 0.248991041 | 13.32739769 | 0.000261556 | 0.045573275 |
| CCNA2 | 20.5346159 | −0.627654197 | 0.175281296 | 13.30323568 | 0.000264948 | 0.045573275 |
| NXF3 | 21.9931399 | −0.874037001 | 0.246746166 | 13.29345619 | 0.000266334 | 0.045573275 |
| C11orf24 | 39.2455928 | −0.422115026 | 0.118646242 | 13.24101829 | 0.000273889 | 0.045998149 |
| NUSAP1 | 163.110628 | −0.312315279 | 0.087355935 | 13.1574169 | 0.000286383 | 0.04722202 |
| CPNE2 | 98.1394967 | −0.412819488 | 0.115624299 | 13.1056335 | 0.000294409 | 0.047678502 |
| ENPP4 | 21.988534 | −0.702457326 | 0.199003539 | 13.00559611 | 0.000310561 | 0.049411963 |
| TADA3 | 384.86541 | −0.461754693 | 0.132540423 | 12.96637032 | 0.000317136 | 0.049588081 |
| CENPJ | 86.1330533 | −0.400578337 | 0.113794638 | 12.91463148 | 0.000326024 | 0.049862843 |
| BPI | 70.1177976 | −0.889016784 | 0.256224363 | 12.8843149 | 0.000331347 | 0.049862843 |
| FAM117B | 78.1729146 | 0.485833993 | 0.13119025 | 12.86163207 | 0.000335388 | 0.049862843 |
| HIBADH | 70.6973939 | 0.306490029 | 0.084559119 | 12.80182626 | 0.000346281 | 0.050537255 |
| DEFA3 | 67.2275316 | −1.117768363 | 0.327944883 | 12.7746206 | 0.000351354 | 0.050537255 |
| TAF1A | 25.0593769 | 0.374110248 | 0.103231417 | 12.74667933 | 0.000356642 | 0.050537255 |
| HIST1H1B | 194.721138 | −0.716085762 | 0.209616837 | 12.64672494 | 0.000376224 | 0.052491955 |
| NCAPG2 | 81.8608202 | −0.2529091 | 0.072071056 | 12.58777256 | 0.000388279 | 0.052889151 |
| MTG1 | 24.3831654 | 0.341740344 | 0.095511983 | 12.57598756 | 0.000390735 | 0.052889151 |
| CKAP2L | 58.9317012 | −0.343643101 | 0.098381001 | 12.52409347 | 0.000401738 | 0.053578821 |
| TRA2B | 676.542908 | −0.25572298 | 0.073568397 | 12.45496838 | 0.000416881 | 0.05479272 |
| ZBTB26 | 19.2710753 | −0.541284898 | 0.159692134 | 12.22219578 | 0.000472243 | 0.060690018 |
| ITGAE | 55.6496691 | −0.580656414 | 0.170762602 | 12.19638948 | 0.000478821 | 0.060690018 |
| TMEM204 | 24.0591736 | −0.617192385 | 0.182647993 | 12.18471832 | 0.000481826 | 0.060690018 |
| DNAJC9 | 194.988335 | −0.462822231 | 0.13578141 | 12.12914118 | 0.0004964 | 0.061483925 |
| ARG1 | 72.4908196 | −0.796757664 | 0.24170391 | 12.07453342 | 0.000511153 | 0.061483925 |
| TRA2A | 242.818114 | −0.370177056 | 0.10842455 | 12.05283964 | 0.000517135 | 0.061483925 |
| HIST1H2AG | 375.263091 | −0.293447479 | 0.085887285 | 12.04075155 | 0.0005205 | 0.061483925 |
| PPP2R5C | 408.606687 | 0.137459246 | 0.039550539 | 12.00514553 | 0.000530539 | 0.061483925 |
| UTP3 | 79.2980827 | 0.461692517 | 0.129523005 | 11.97005354 | 0.000540624 | 0.061483925 |
| BMS1 | 183.723177 | 0.241018859 | 0.068716246 | 11.95976754 | 0.000543617 | 0.061483925 |
| WHSC1 | 185.31172 | −0.226521785 | 0.066425648 | 11.92423415 | 0.000554084 | 0.061483925 |
| NUP133 | 110.269171 | 0.156526589 | 0.04522125 | 11.91679955 | 0.0005563 | 0.061483925 |
| SLC25A15 | 42.0037796 | −0.596960989 | 0.178414071 | 11.860334 | 0.000573423 | 0.061483925 |
| MYO1E | 88.9824676 | 0.404503129 | 0.114157332 | 11.84234693 | 0.000578988 | 0.061483925 |
| TLE1 | 22.5766189 | 0.54382872 | 0.153891879 | 11.84212637 | 0.000579057 | 0.061483925 |
| CENPF | 286.307473 | −0.601321328 | 0.18356273 | 11.81108262 | 0.000588792 | 0.061483925 |
| HNRNPM | 1750.4597 | 0.170158862 | 0.04909502 | 11.81061753 | 0.000588939 | 0.061483925 |
| CCNE2 | 19.1264461 | −0.354971369 | 0.104477344 | 11.77598515 | 0.000599998 | 0.061483925 |
| TNKS2 | 219.507656 | 0.158809062 | 0.046014002 | 11.7758489 | 0.000600041 | 0.061483925 |
| TYMS | 62.2905051 | −0.499118477 | 0.148971538 | 11.73008608 | 0.000614977 | 0.061483925 |
| ATP1B1 | 66.7258463 | −0.78171204 | 0.242172775 | 11.7283898 | 0.000615538 | 0.061483925 |
| HSPA4 | 603.817699 | 0.130939432 | 0.038066225 | 11.70951895 | 0.000621812 | 0.061483925 |
| KIF11 | 74.4096422 | −0.291879346 | 0.086082108 | 11.68479707 | 0.000630129 | 0.061483925 |
| GPR155 | 31.7649463 | −0.478814886 | 0.143773625 | 11.66861505 | 0.000635633 | 0.061483925 |
| KCTD18 | 81.6905015 | −0.494420831 | 0.149178602 | 11.66380216 | 0.00063728 | 0.061483925 |
| CHMP1A | 78.9514046 | −0.28448745 | 0.084366365 | 11.6295058 | 0.000649138 | 0.061968763 |
| CYB5R4 | 245.544953 | −0.240885249 | 0.071641203 | 11.58170704 | 0.000666038 | 0.062919751 |
| SURF4 | 39.7092905 | −0.423964499 | 0.127821348 | 11.55995935 | 0.000673873 | 0.063003677 |
| UBFD1 | 23.440026 | 0.51702477 | 0.1473821 | 11.49849634 | 0.000696525 | 0.064457005 |
| MS4A3 | 45.4722541 | −0.846596609 | 0.259710365 | 11.42078505 | 0.00072627 | 0.066474938 |
| ZNF100 | 72.7823971 | −0.313967903 | 0.093889894 | 11.40367192 | 0.000732991 | 0.066474938 |
| FBRSL1 | 157.84346 | −0.423476217 | 0.129442424 | 11.34208635 | 0.000757702 | 0.067456821 |
| HIST1H3B | 160.992723 | −0.563354995 | 0.172589487 | 11.33283675 | 0.000761485 | 0.067456821 |
| JMJD1C | 1173.54762 | −0.321356114 | 0.096927602 | 11.32153835 | 0.000766132 | 0.067456821 |
| HDGF | 1516.62537 | −0.320347942 | 0.097986788 | 11.29956087 | 0.000775254 | 0.067603661 |
| GFOD1 | 46.2615555 | −0.390620305 | 0.120574865 | 11.26119987 | 0.00079144 | 0.067733245 |
| ZNF347 | 56.7785617 | −0.483136357 | 0.147301071 | 11.24435606 | 0.000798658 | 0.067733245 |
| NT5C2 | 315.658417 | −0.288282573 | 0.087621237 | 11.24321471 | 0.000799146 | 0.067733245 |
| SERPINB10 | 30.1641459 | −0.91614822 | 0.286942518 | 11.16704123 | 0.000832633 | 0.069647542 |
| ADCY3 | 131.715381 | −0.755386896 | 0.235882849 | 11.15713403 | 0.000837091 | 0.069647542 |
| HDAC6 | 85.9990103 | −0.257845644 | 0.078305194 | 11.12402269 | 0.000852168 | 0.07025735 |
| FNBP1L | 688.822315 | −0.583258432 | 0.179846878 | 11.02494984 | 0.000898937 | 0.073445592 |

TABLE 5-continued

Set of Genes Predictive for Pre-Term Birth (PTB)

| Gene | BaseMean | Log2FoldChange | lfcSE | Stat | P Value | P_adj |
|---|---|---|---|---|---|---|
| CDCA2 | 27.9846514 | −0.351604469 | 0.106383011 | 10.96863027 | 0.000926672 | 0.074331571 |
| PKP2 | 59.0515065 | −0.5919732 | 0.185121482 | 10.93505182 | 0.000943618 | 0.074331571 |
| MAFG | 62.4155814 | −0.475736151 | 0.148504114 | 10.92588387 | 0.0009483 | 0.074331571 |
| HIST1H2AL | 100.449723 | −0.549602282 | 0.171209237 | 10.91134298 | 0.000955772 | 0.074331571 |
| CD109 | 226.319539 | −0.722114926 | 0.221290922 | 10.9069803 | 0.000958026 | 0.074331571 |
| MMP8 | 61.7414815 | −0.963025712 | 0.306340595 | 10.89073584 | 0.000966464 | 0.074331571 |
| ANLN | 115.731414 | −0.295842283 | 0.090850141 | 10.88941321 | 0.000967155 | 0.074331571 |
| MTMR10 | 733.404726 | −0.480452862 | 0.149333198 | 10.85233363 | 0.000986713 | 0.075197506 |
| PMPCB | 132.728427 | 0.238068066 | 0.071311803 | 10.80424715 | 0.001012675 | 0.076052074 |
| ZDHHC3 | 66.0394411 | −0.260252119 | 0.080306011 | 10.80055166 | 0.001014699 | 0.076052074 |
| STRN4 | 542.589927 | −0.403498387 | 0.125812989 | 10.75598871 | 0.001039424 | 0.077266708 |
| SLC30A1 | 41.582641 | −0.48709392 | 0.153134635 | 10.73638939 | 0.001050491 | 0.077454495 |
| THUMPD1 | 309.207619 | −0.406262264 | 0.127203679 | 10.67845738 | 0.001083904 | 0.079219698 |
| UNC13D | 448.751353 | −0.435984447 | 0.136240502 | 10.66273958 | 0.001093154 | 0.079219698 |
| COL6A3 | 229.356044 | −0.871540967 | 0.279680555 | 10.64316563 | 0.001104784 | 0.079219698 |
| DACH1 | 49.7307281 | −0.357313535 | 0.109906151 | 10.60586614 | 0.001127294 | 0.079219698 |
| PDZD8 | 154.486387 | −0.257891719 | 0.079851585 | 10.59729745 | 0.001132531 | 0.079219698 |
| MCM7 | 83.7976273 | −0.306443012 | 0.09451062 | 10.59553298 | 0.001133612 | 0.079219698 |
| H2AFX | 26.7167358 | −0.621633373 | 0.195620526 | 10.59232889 | 0.001135578 | 0.079219698 |
| PDLIM7 | 380.727424 | −0.505011238 | 0.160089466 | 10.53019631 | 0.001174397 | 0.080999672 |
| XRCC2 | 19.1233452 | −0.678008232 | 0.21669442 | 10.52303581 | 0.001178957 | 0.080999672 |
| HIST1H2AD | 97.3430238 | −0.34596932 | 0.108676691 | 10.44132953 | 0.001232265 | 0.083449616 |
| SNX2 | 647.453038 | 0.202977723 | 0.061821064 | 10.4402004 | 0.001233019 | 0.083449616 |
| CDK1 | 18.0714248 | −0.51816235 | 0.162355531 | 10.33963387 | 0.001302038 | 0.087226169 |
| CCDC71L | 37.33982 | −0.400919901 | 0.127802181 | 10.32455688 | 0.001312718 | 0.087226169 |
| CKLF | 37.8805589 | −0.462449877 | 0.14699266 | 10.29862805 | 0.001331292 | 0.087226169 |
| NBEAL2 | 340.162037 | −0.432033009 | 0.136441565 | 10.29489473 | 0.001333988 | 0.087226169 |
| BLK | 43.4801839 | 0.634035324 | 0.188877899 | 10.29085666 | 0.00133691 | 0.087226169 |
| TBC1D17 | 58.4749713 | −0.373545049 | 0.118601337 | 10.24113633 | 0.00137343 | 0.087484066 |
| LEF1 | 151.118851 | 0.643948384 | 0.191173884 | 10.23488179 | 0.001378094 | 0.087484066 |
| ZMIZ2 | 192.67977 | −0.414950646 | 0.133664118 | 10.22724077 | 0.001383815 | 0.087484066 |
| PROSC | 153.538309 | 0.198924963 | 0.061677357 | 10.22540842 | 0.001385191 | 0.087484066 |
| HBG2 | 345.124523 | −0.918493788 | 0.296215427 | 10.21880457 | 0.001390159 | 0.087484066 |
| G6PD | 636.863085 | −0.407286058 | 0.13130294 | 10.20745346 | 0.001398742 | 0.087484066 |
| SCAMP2 | 67.7773099 | −0.394249471 | 0.126956056 | 10.16850961 | 0.001428597 | 0.088739365 |
| ADSL | 225.751847 | 0.196671315 | 0.061110072 | 10.14454322 | 0.00144729 | 0.089288946 |
| TTC14 | 35.3500103 | −0.41643018 | 0.131587484 | 10.10593962 | 0.001477922 | 0.090562679 |
| SNX19 | 56.1029379 | −0.586594521 | 0.192975491 | 10.07305605 | 0.001504533 | 0.091574547 |
| SSH1 | 283.720048 | −0.430272183 | 0.139594448 | 10.01954535 | 0.001548877 | 0.092537718 |
| PUDP | 20.5130162 | 0.344091852 | 0.108081232 | 10.01828007 | 0.001549941 | 0.092537718 |
| MECP2 | 485.159305 | −0.330039312 | 0.106259251 | 10.01705997 | 0.001550968 | 0.092537718 |
| CD63 | 369.814694 | −0.370604322 | 0.119643709 | 9.97005192 | 0.00159107 | 0.093697832 |
| KCNMB1 | 50.8034229 | −0.621752932 | 0.205706399 | 9.966132454 | 0.001594461 | 0.093697832 |
| MAPKAPK5 | 123.545681 | 0.16432536 | 0.051688944 | 9.958128716 | 0.001601407 | 0.093697832 |
| GSN | 1142.9619 | −0.513473609 | 0.167530371 | 9.917485992 | 0.001637159 | 0.095175581 |
| LOXHD1 | 199.692968 | −0.731866353 | 0.24195628 | 9.90140628 | 0.001651525 | 0.095364629 |
| RSRC2 | 830.686621 | −0.262498114 | 0.084618777 | 9.890390225 | 0.001661441 | 0.095364629 |
| NLRX1 | 30.7233614 | −0.509357783 | 0.166698746 | 9.843889299 | 0.001703968 | 0.095988604 |
| SEPT1 | 110.886498 | 0.323262856 | 0.101511457 | 9.840581353 | 0.001707035 | 0.095988604 |
| CD69 | 38.0149845 | −0.674155226 | 0.219370446 | 9.834226717 | 0.001712943 | 0.095988604 |
| ZWINT | 24.8850687 | −0.39823044 | 0.128888897 | 9.819550962 | 0.001726665 | 0.095988604 |
| MPZL3 | 113.172834 | −0.654041276 | 0.209805319 | 9.802115693 | 0.001743112 | 0.095988604 |
| C19orf60 | 16.0678764 | 0.360656348 | 0.114692869 | 9.795694668 | 0.001749209 | 0.095988604 |
| DHRS7 | 141.576438 | −0.39952924 | 0.130352818 | 9.792485914 | 0.001752264 | 0.095988604 |
| HIST1H3D | 53.2585736 | −0.400948931 | 0.129905156 | 9.781128458 | 0.001763121 | 0.095988604 |
| URGCP | 27.7194428 | 0.340624969 | 0.106525549 | 9.762391628 | 0.00178118 | 0.095988604 |
| SLFN5 | 215.94271 | 0.480638388 | 0.148370925 | 9.739063308 | 0.001803928 | 0.095988604 |
| DENND5B | 61.3148853 | 0.314946804 | 0.099031453 | 9.735650377 | 0.001807281 | 0.095988604 |
| HDAC8 | 41.9432708 | −0.268324265 | 0.087630995 | 9.735604359 | 0.001807326 | 0.095988604 |
| MPO | 58.7414306 | −0.702404473 | 0.234008372 | 9.732980597 | 0.001809908 | 0.095988604 |
| LBR | 97.386483 | −0.388828754 | 0.12690985 | 9.718285563 | 0.001824436 | 0.096196585 |
| SLC25A17 | 26.6395003 | −0.435027079 | 0.141781328 | 9.693486997 | 0.001849223 | 0.096939895 |
| PHF10 | 89.6542661 | 0.211046689 | 0.067249259 | 9.670560543 | 0.001872442 | 0.097592955 |
| C5orf51 | 85.5546517 | −0.439052137 | 0.144932302 | 9.651442593 | 0.001892029 | 0.09763215 |
| LIMA1 | 90.6336708 | −0.243337275 | 0.079242036 | 9.61963325 | 0.001925082 | 0.09763215 |
| KIF4A | 42.6606646 | −0.303097287 | 0.099303103 | 9.597227403 | 0.001948714 | 0.09763215 |
| HOMER2 | 762.904045 | −0.64907536 | 0.218124585 | 9.596591311 | 0.001949389 | 0.09763215 |
| MYB | 80.830462 | −0.386211669 | 0.126466593 | 9.595490392 | 0.001950558 | 0.09763215 |
| NMT2 | 49.2941549 | 0.453745355 | 0.141576441 | 9.579588804 | 0.001967525 | 0.09763215 |
| ERICH1 | 445.217991 | −0.412096292 | 0.134791355 | 9.570673095 | 0.001977103 | 0.09763215 |
| LOX | 38.7753467 | −0.837609776 | 0.282800795 | 9.568551905 | 0.001979389 | 0.09763215 |
| EMC7 | 38.9232153 | −0.297068531 | 0.097179965 | 9.56836946 | 0.001979585 | 0.09763215 |
| RNF167 | 143.994981 | −0.28593229 | 0.094447548 | 9.567198302 | 0.001980849 | 0.09763215 |
| SVIL | 640.967988 | −0.425770686 | 0.139799407 | 9.551376014 | 0.001997996 | 0.097944996 |

TABLE 5-continued

Set of Genes Predictive for Pre-Term Birth (PTB)

| Gene | BaseMean | Log2FoldChange | lfcSE | Stat | P Value | P_adj |
|---|---|---|---|---|---|---|
| SGMS1 | 55.9206306 | −0.461626108 | 0.15425216 | 9.533346984 | 0.002017718 | 0.098380034 |
| IMPAD1 | 53.4291124 | −0.579371195 | 0.19336976 | 9.502711545 | 0.002051685 | 0.099376942 |
| MAPK6 | 287.705426 | −0.48667072 | 0.162417619 | 9.495218971 | 0.00206008 | 0.099376942 |

TABLE 6

Predictive Model Weights of Genes Predictive for Pre-Term Birth (PTB)

| Gene | Weight |
|---|---|
| ELANE | 0.0989222 |
| ACSM3 | 0.07557269 |
| MAPK10 | 0.06882871 |
| IRX3 | 0.06702434 |
| SPAG5 | 0.06010713 |
| B3GNT2 | 0.05968447 |
| LOX | 0.05033319 |
| H2AFX | 0.04841582 |
| ITGAE | 0.03649107 |
| ARL4A | −0.0354448 |
| ZBTB26 | 0.03028558 |
| BEX1 | 0.02647277 |
| HBG2 | 0.02617242 |
| SNX19 | 0.0248166 |
| CCNA2 | 0.02240897 |
| TLE1 | −0.0213883 |
| TMEM204 | 0.01798467 |
| MRTO4 | −0.0124935 |
| PHGDH | 0.01168144 |
| IMPAD1 | 0.00555929 |
| KCNMB1 | 0.00518973 |
| ENPP4 | 0.00388786 |
| MMP8 | −0.0029393 |
| MPZL3 | 0.00211636 |
| NLRX1 | 0.00085898 |

Figure 7G:
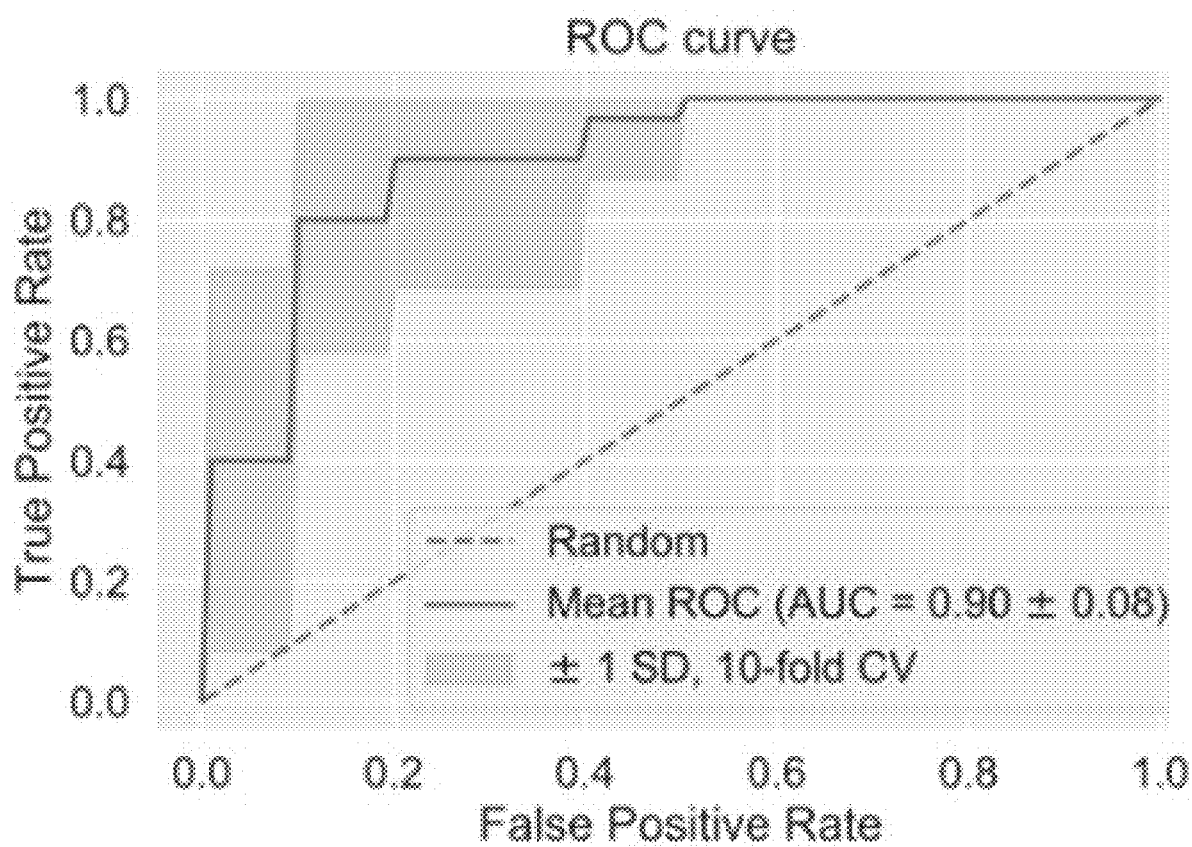
FIG. 7G shows a receiver-operating characteristic (ROC) curve showing the performance of the predictive model for pre-term delivery across the 10-fold cross-validation, in accordance with disclosed embodiments.

FIG. 7G shows a receiver-operating characteristic (ROC) curve showing the performance of the predictive model for pre-term delivery across the 10-fold cross-validation. As shown in the figure, the predictive model for predicting pre-term delivery achieved a mean area under the curve (AUC) of 0.90±0.08, thereby demonstrating the excellent performance of the predictive model for predicting pre-term delivery.

Example 5: Prediction of Due Date (DD)

Using systems and methods of the present disclosure, a prediction model is developed to predict a due date of a fetus of a pregnant subject. For example, the predicted due date can be a number of days (e.g., 1 day, 2 days, 3 days, 4 days, 5 days, 6 days, or 7 days) or weeks (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, or 45 weeks) until an expected delivery of the fetus of the pregnant subject. As another example, the predicted due date can be a future date on which the delivery of the fetus of the pregnant subject is expected to occur.

The prediction model may be based on assaying a sample (e.g., a blood draw) of a pregnant subject at a given time point (e.g., at an estimated gestational age of 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, or 45 weeks).

Figure 8:
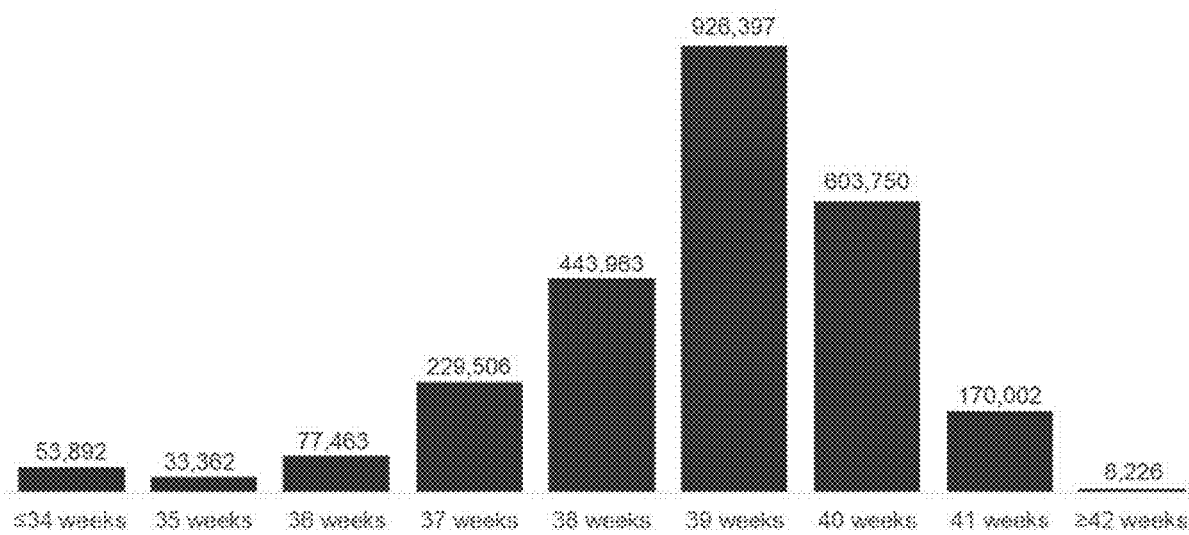
FIG. 8 shows an example of a distribution of vaginal singleton births by obstetrician-estimated gestational age in the U.S.

FIG. 8 shows an example of a distribution of vaginal singleton births by obstetrician-estimated gestational age in the U.S. This figure shows that only 23.7% of vaginal singleton births occur at an estimated gestational age of 40 weeks, and about 67% of vaginal singleton births occur at an estimated gestational age of 39-41 weeks. Therefore, such variation of time of delivery illustrates the need for a better predictor of delivery date that uses a molecular clock, using systems and methods of the present disclosure.

Figure 9A:
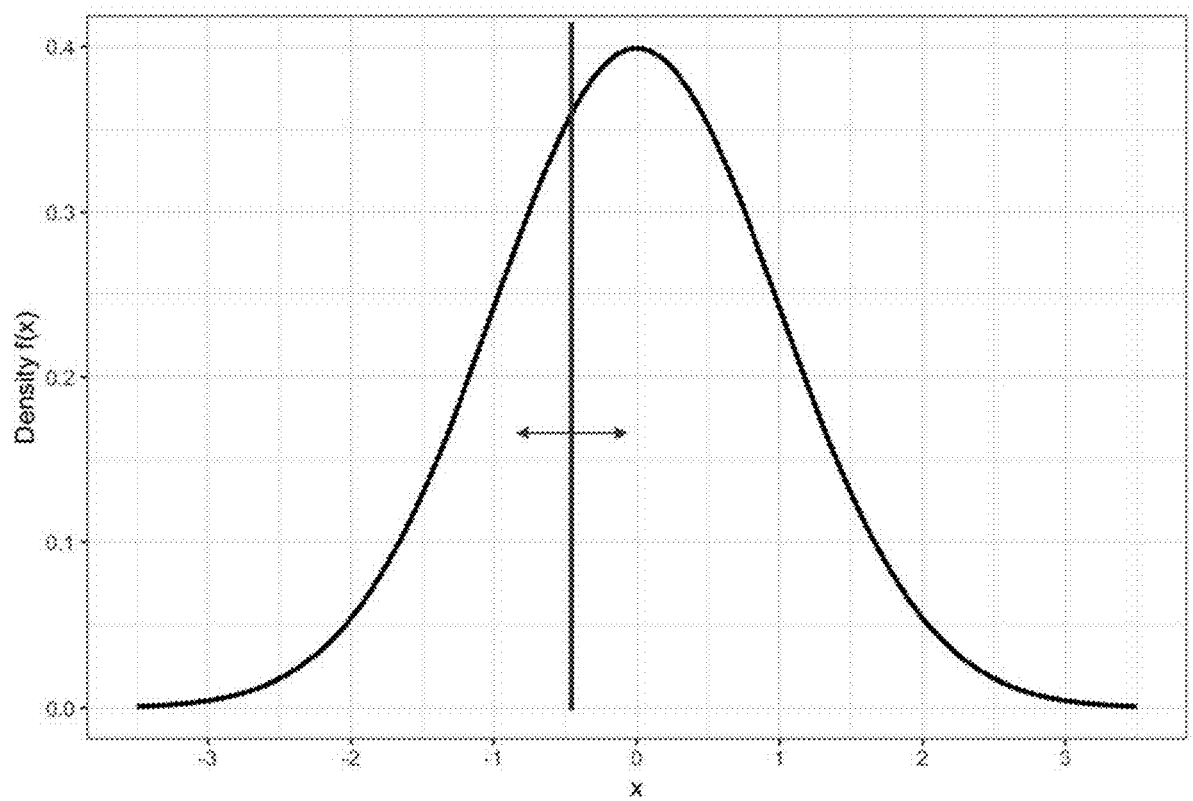
FIG. 9A-9E show different methods of predicting due date for a fetus of a pregnant subject, including predicting an actual day (with error) (FIG. 9A), predicting a week (or other window) of delivery (FIG. 9B), predicting whether a delivery is expected to occur before or after a certain time boundary (FIG. 9C), predicting in which bin among a plurality of bins (e.g., 6 bins) a delivery is expected to occur (FIG. 9D), and predicting a relative risk or relative likelihood of an early delivery or a late delivery (FIG. 9E).
Figure 9B:
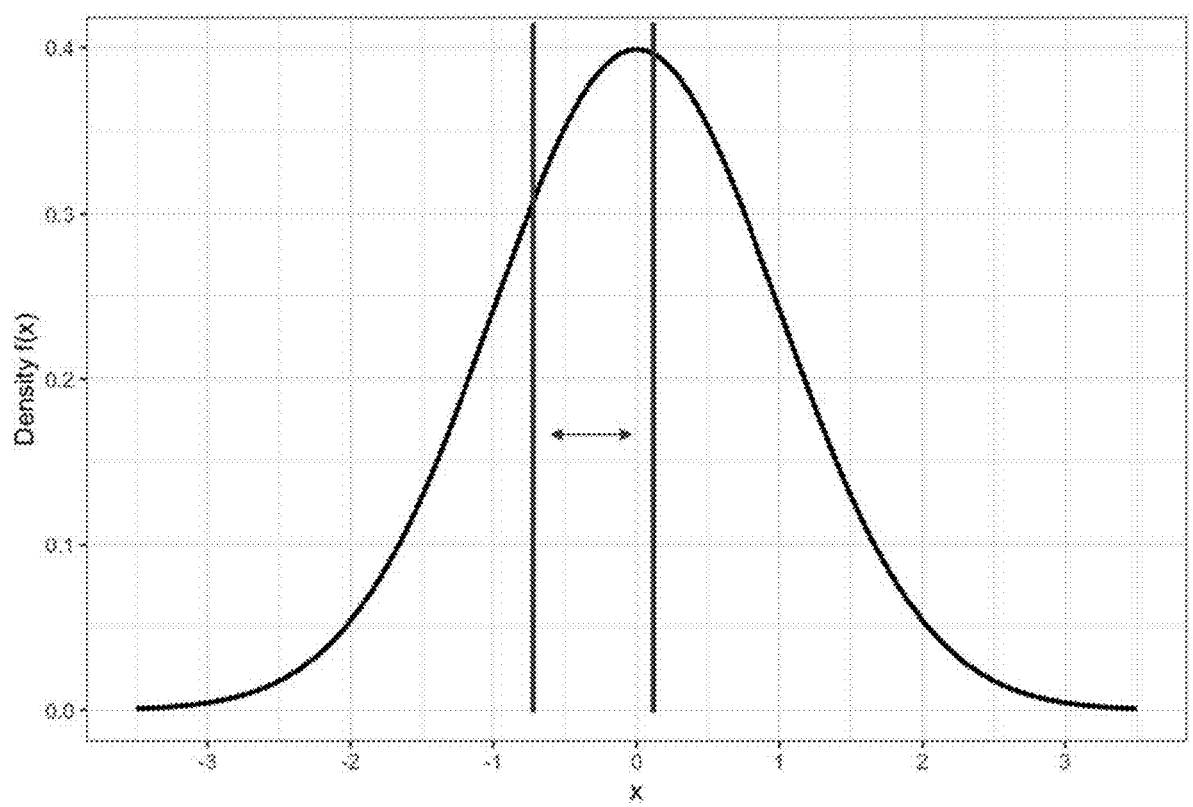
Figure 9C:
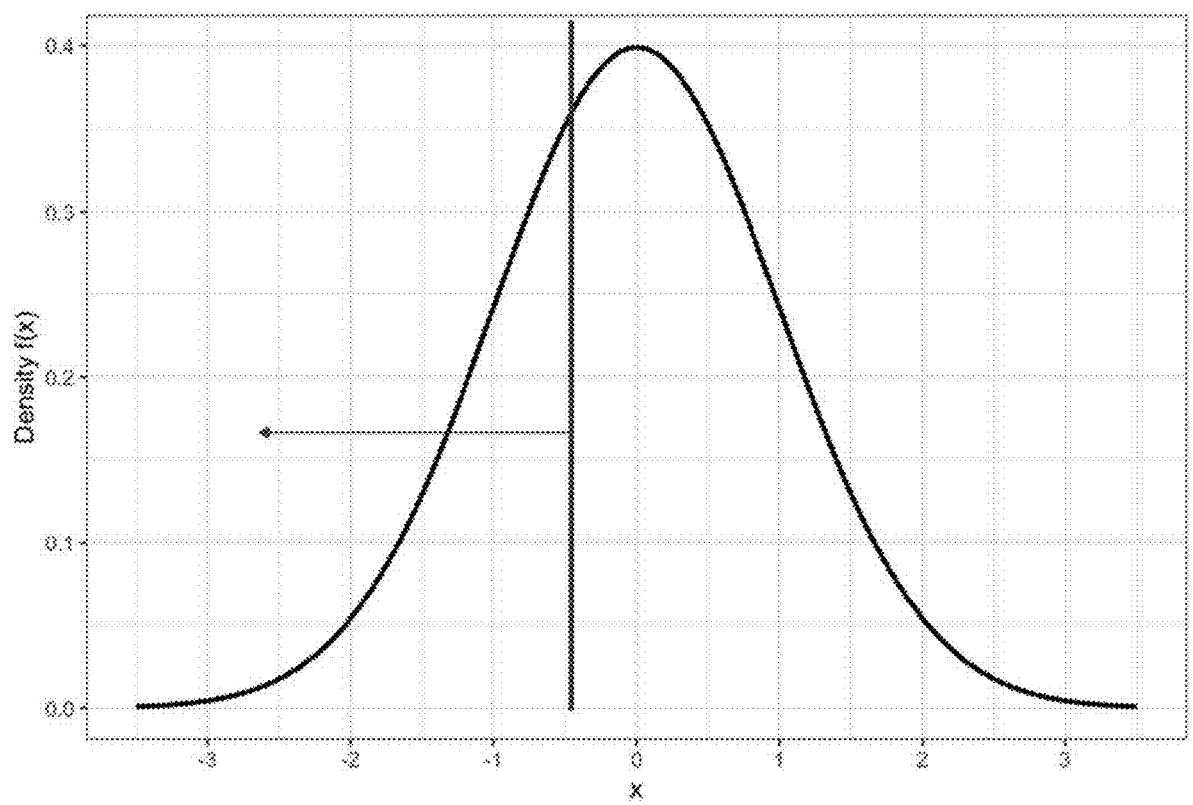
Figure 9D:
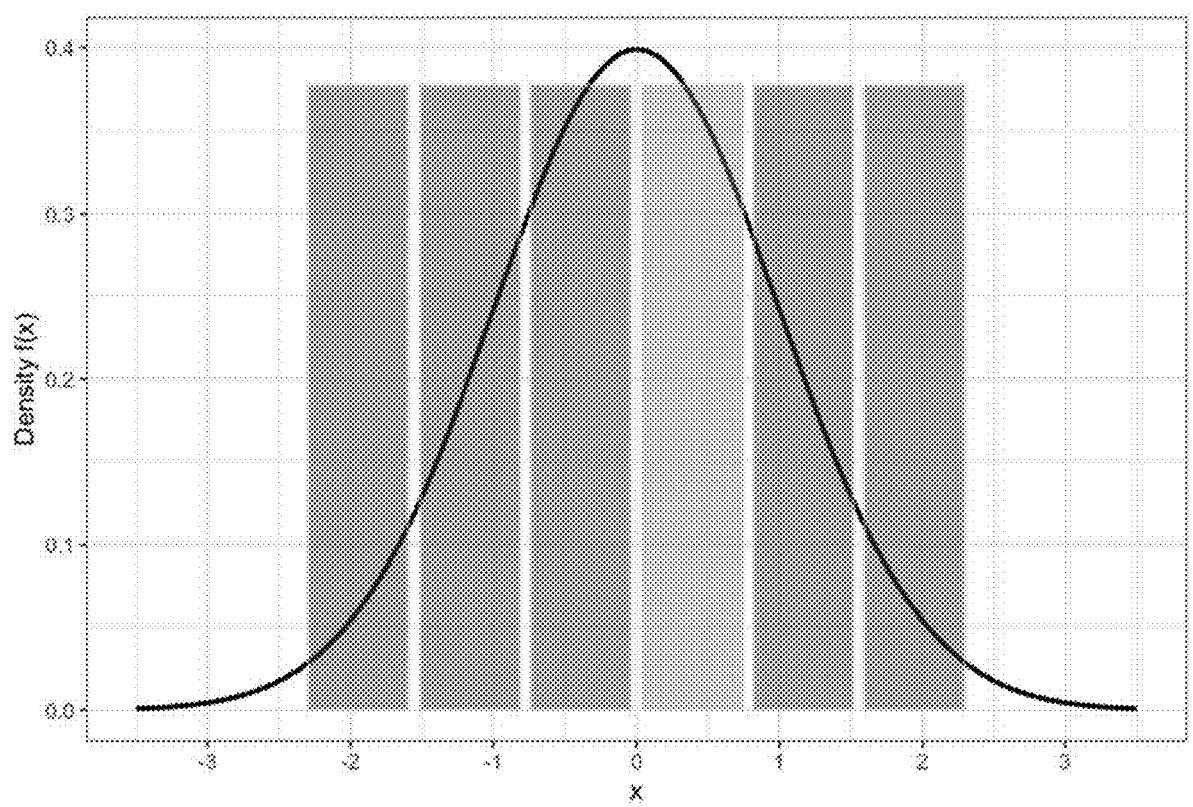
Figure 9E:
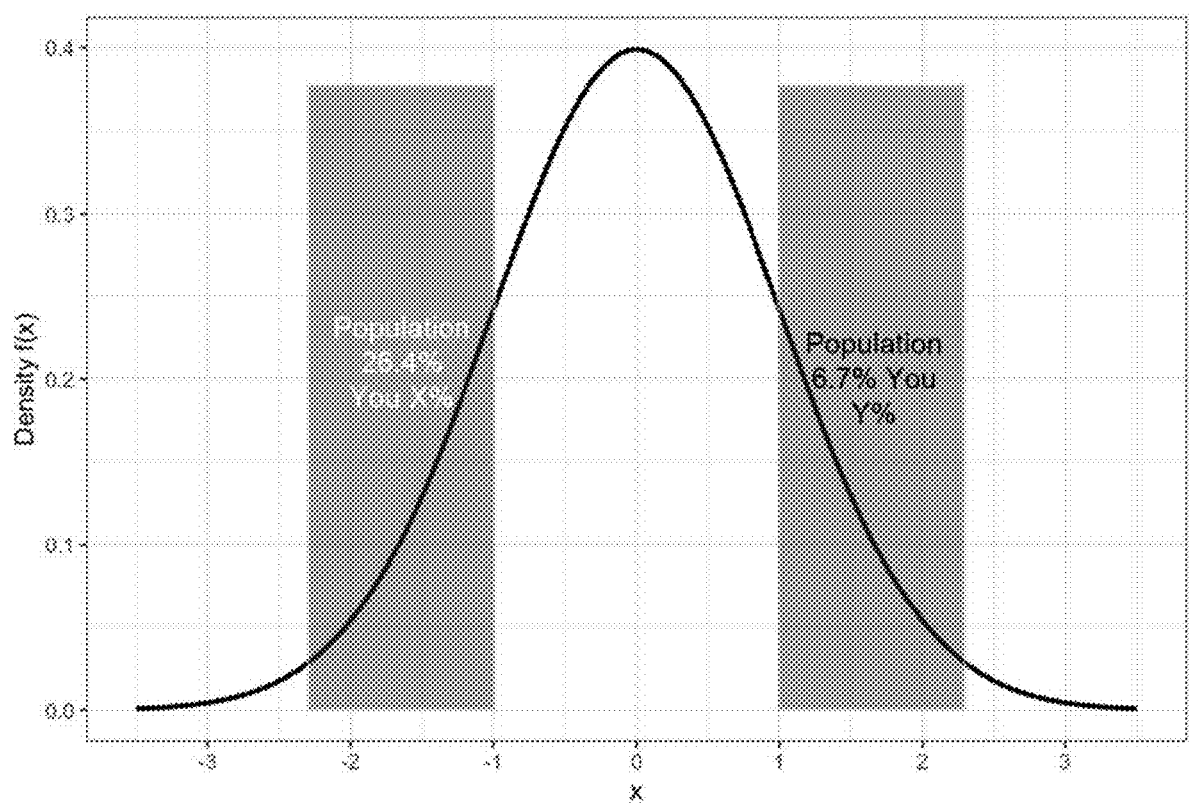

FIG. 9A-9E show different methods of predicting due date for a fetus of a pregnant subject, including predicting an actual day (with error) (FIG. 9A), predicting a week (or other window) of delivery (FIG. 9B), predicting whether a delivery is expected to occur before or after a certain time boundary (FIG. 9C), predicting in which bin among a plurality of bins (e.g., 6 bins) a delivery is expected to occur (FIG. 9D), and predicting a relative risk or relative likelihood of an early delivery or a late delivery (FIG. 9E).

For example, the due date prediction model may be used to predict an actual day (with error) (FIG. 9A). For example, the predicted due date may be a number of days (e.g., 1 day, 2 days, 3 days, 4 days, 5 days, 6 days, or 7 days) or weeks (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, or 45 weeks) until an expected delivery of the fetus of the pregnant subject. As another example, the predicted due date may be a future date on which the delivery of the fetus of the pregnant subject is expected to occur. As another example, the predicted due date may be an estimated gestational age (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, or 45 weeks) for which the delivery of the fetus of the pregnant subject is expected to occur. The predicted due date may be provided along with an error or confidence interval (e.g., 1 day, 2 days, 3 days, 4 days, 5 days, 6 days, 7 days, 2 weeks, 3 weeks, or 4 weeks) for the predicted due date. The predicted due date may be provided along with an estimated likelihood or confidence (e.g., about 50%, 55%, 60%, 65%, 70%, 75%, 80%, 85%, 90%, 91%, 92%, 93%, 94%, 95%, 96%, 97%, 98%, or 99%) for the predicted due date.

As another example, the due date prediction model may be used to predict a week (or other window) of delivery (FIG. 9B). For example, the predicted due date may be a number of weeks (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, or 45 weeks) until an expected delivery of the fetus of the pregnant subject. As another example, the predicted due date may be a future week (e.g., a week on the calendar) on which the delivery of the fetus of the pregnant subject is expected to occur. As another example, the predicted due date may be an estimated gestational age (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, or 45 weeks) for which the delivery of the fetus of the pregnant subject is expected to occur. The predicted due date may be provided along with an estimated likelihood or confidence (e.g., about 50%, 55%, 60%, 65%, 70%, 75%, 80%, 85%, 90%, 91%, 92%, 93%, 94%, 95%, 96%, 97%, 98%, or 99%) for the predicted due date.

As another example, the due date prediction model may be used to predict whether a delivery is expected to occur before or after a certain time boundary (FIG. 9C). For example, the time boundary may be a number of weeks (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, or 45 weeks) of estimated gestational age. For example, the time boundary may be an estimated gestational age of 40 weeks.

As another example, the due date prediction model may be used to predict which bin among a plurality of bins (e.g., 6 bins) a delivery is expected to occur (FIG. 9D). For example, the bins (e.g., time windows) may be equal ranges of time (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks; or 1 month, 2 months, 3 months, 4 months, or 5 months; or a trimester among the first, second, or third trimesters). The predicted due date may be provided along with an estimated likelihood or confidence (e.g., about 50%, 55%, 60%, 65%, 70%, 75%, 80%, 85%, 90%, 91%, 92%, 93%, 94%, 95%, 96%, 97%, 98%, or 99%) for the predicted due date bin or time window.

As another example, the due date prediction model may be used to predict a relative risk or relative likelihood of an early delivery or a late delivery (FIG. 9E). For example, the prediction may comprise a relative risk or relative likelihood of an early delivery or a late delivery of about 10%, 20%, 30%, 40%, 50%, 55%, 60%, 65%, 70%, 75%, 80%, 85%, 90%, 91%, 92%, 93%, 94%, 95%, 96%, 97%, 98%, or 99%. An early delivery may be defined as a due date at an estimated gestational age of less than 40 weeks, while a late delivery may be defined as a due date at an estimated gestational age of more than 40 weeks.

A due date prediction model was trained using samples collected from a gestational age (GA) cohort of pregnant subjects, all of whom had an estimated gestational age of a fetus of 34 weeks to 36 weeks. A training dataset was obtained using a cohort of 270 and 312 Pittsburg samples (about half of which was Caucasian and half of which was AA), of which 41 samples were designated as lab outliers and not used and 1 sample had an outlier low CPM. Further, a test dataset of 64 samples was obtained using a cohort (003_GA) of 19 GAPPS samples (most of whom were Caucasian) and a cohort (009_VG) of 47 validation GAPPS samples (all of whom had an estimated gestational age of a fetus of 34 weeks to 36 weeks, and most of whom were Caucasian).

Gene discovery was performed to develop the due date prediction model as follows. A set of 241 input genes, comprising candidate marker genes, was used. Using the training dataset, a subset of these candidate marker genes was identified as having a high median(log2_CPM) value of greater than 0.5. An analysis of variance (ANOVA) was performed using a set of 248 genes (as shown in Table 7) for actual time to delivery for the training samples (e.g., −7 weeks vs. −2 weeks for the top 100 genes, and −6 weeks vs. −3 weeks for the top 100 genes). A Pearson linear correlation was performed to identify the top 100 genes among the candidate marker genes having the strongest statistical correlation to due date. A number of different prediction models were tested for prediction of time-to-delivery bins. First, the standard of care was used in which a predicted time to delivery was made based on a predicted due date at a gestational age of 40 weeks. Second, an estimated gestational age using ultrasound data only was used, using the collectionga cohort as an input to the elastic net prediction model. Third, an estimated gestational age using cfDNA only was used, using an input of log2_CPMs of genes and confounders (e.g., parity, BMI, smoking status, etc.) as inputs to the elastic net prediction model. Fourth, an estimated gestational age using both cfDNA plus ultrasound was used, using an input of log2_CPMs of genes, confounders, and collectionga input to the elastic net prediction model.

TABLE 7

Set of 248 Genes Used in ANOVA Model
Genes

ABCB1, AC010468.1, AC068657.2, AC078899.1, AC079250.1, AC114752.3, ACOX1, ACTA2, ACTBP8, ACTG1P15, ADAM12, ADCK5, ADGRE1, ADGRG5, ADGRL2, AKR1C1, AKR1E2, ALG1, ALS2, AMT, ANO5, ANP32AP1, ANP32C, APBA3, ARFGEF3, ASMTL, ATAD3A, ATF4P3, ATP8B3, BBOF1, BBS4, BCAR3, BCYRN1, C14orf119, C1orf228, C2orf42, C6orf106, C6orf47, C9orf3, CALM1P1, CALM2, CAMK2D, CASC4P1, CD177, CD68, CDC27, CDC42P6, CDK5RAP2, CFAP43, CFAP70, CHAC2, CHCHD4, CHKA, CKAP2, CLC, CLN5, CMTM3, CNOT6LP1, CNTNAP2, COPA, CRH, CSRNP2, CSTF2, CTB-79E8.3, CXCR3, CXXC4, CYP51A1, CYYR1, DAB2IP, DCUN1D1, DEPDC1B, DHCR24, DHTKD1, DOCK9, DRAM1, DSC2, EEF1A1P16, EIF1AXP1, EIF3LP2, EIF4EBP3, ELMOD3, ETFRF1, EVX2,

TABLE 7-continued

Set of 248 Genes Used in ANOVA Model
Genes

EXO5, FAM120A, FBP1, FBXL14, FCGR3B, FGF2, FLIT,
FN1, FTH1P3, FZD6, GABPA, GAS2, GATAD2B, GLIS2,
GLRA4, GOLGA2, H2BFS, HMGB1P11, HMGB3P22, HMGCS1,
HNRNPKP1, HNRNPKP4, HP, HPCAL1, HSPG2, ICAM4,
ICMT, IKZF2, IL2RA, INHBA, INPP5K, INTS4, INTS6,
ITGA3, ITGB4, KCMF1, KCNK5, KIF3A, KLHDC8B, KLRC1,
LRP5, MAGT1, MAPK1, MAPK11, MAPK13, MCCC1, MCEMP1,
MECP2, Metazoa_SRP_ENSG00000278771, MGAT3, MIB1,
MOB4, MORF4L1, MRRF, MT-TE, MT-TP, MTDHP3, MUT,
MYL12BP2, NAP1L1P1, NCOA1, NDUFV2P1, NEK6,
NEMP2, NRCAM, OASL, OGDH, PAK3, PAPPA, PAPPA2,
PASK, PDZRN4, PERP, PIGM, PMM1, PHU, PPM1H,
PRICKLE4, PRKCZ, PSG9, PSMC3IP, PTMA, RAB3GAP2,
RAB43, RAP1BP1, RBBP4P1, RELL1, RFX2, RN7SL1, RN7SL396P,
RN7SL767P, RNA5SP355, RNY1, ROBO3, RP1-121G13.3,
RP3-393E18.1, RPL14P3, RPL15P2, RPL19P16, RPL5P5, RPTOR,
RRN3P1, RSU1P1, SCAND1, SEPT7P2, SERPINB9, SHISA5,
SIRPG, SKOR1, SKP1P1, SLC43A1, SNRNP48, SPCS2,
SRGAP2C, SRP9P1, STAG3L2, STAT5B, STRAP, STX2,
SVEP1, SYN2, TAF6L, TANC1, TEK, TGDS, THOC3, THOC7,
TIE1, TMA7, TMEM14A, TMEM222, TMEM237, TMEM8A,
TPI1P1, TRAV12-2, TRAV14DV4, TRIM36, TTBK2, TTC28,
UBE2R2, UQCRHL, VPS33B, WDR37, WDR77, WTH3DI,
Y_RNA_ENSG00000199303, Y_RNA_ENSG00000201412,
Y_RNA_ENSG00000202357, Y_RNA_ENSG00000202533,
Y_RNA_ENSG00000252891, YPEL2, ZBED5-AS1, ZBTB16,
ZBTB20, ZEB2P1, ZFY, ZNF148, ZNF319, ZNF563, ZNF696,
ZNF714, ZSCAN16-AS1, ZSCAN22, ZSCAN30

Figure 10:
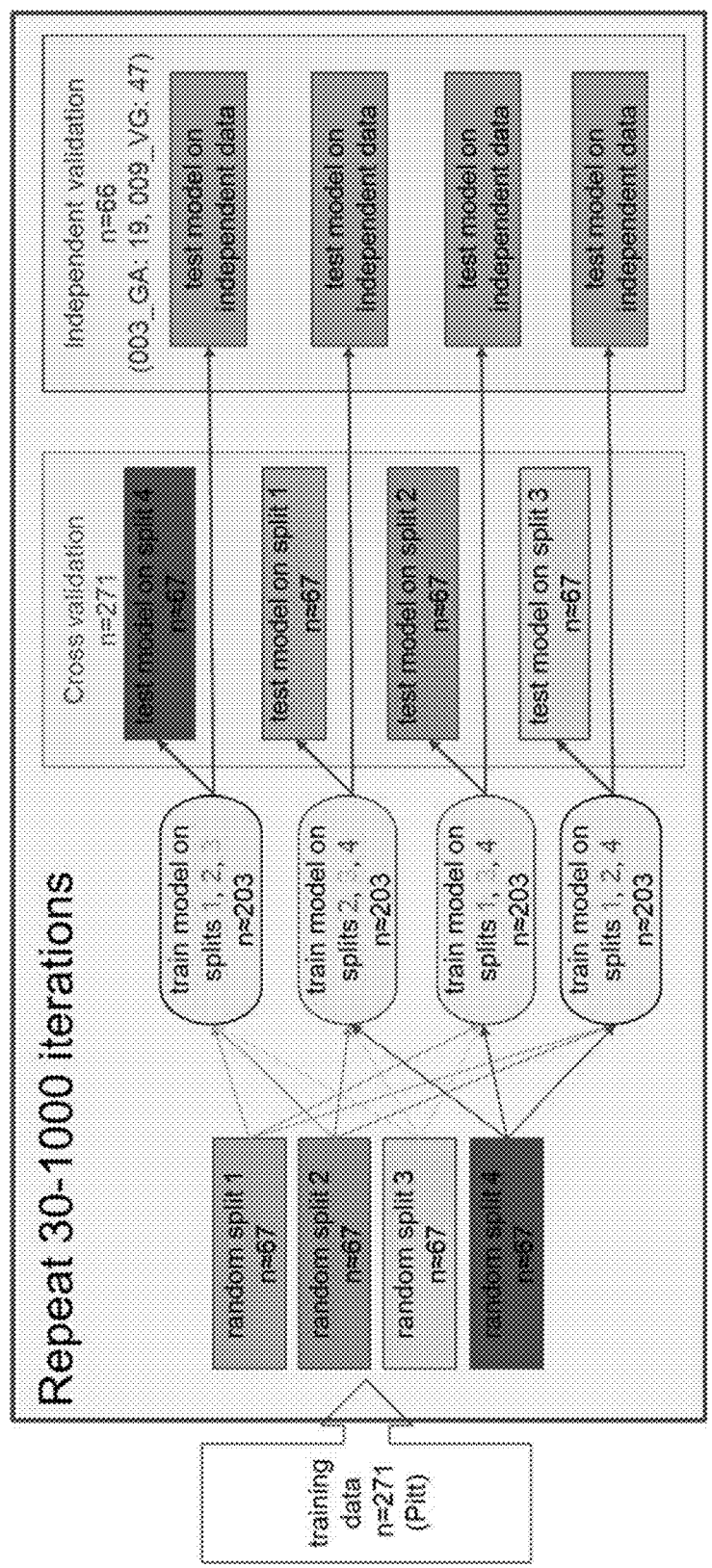
FIG. 10 shows a data workflow that is performed to develop a due date prediction model (e.g., classifier).

FIG. 10 shows a data workflow that is performed to develop a due date prediction model (e.g., classifier). First, the training data (n=271 samples) is randomly split up into 4 sets of 67 samples each. Next, the model is trained using different combinations of 3 of the 4 split sets that are creating by leaving out 1 split set at a time (e.g., a first combination of splits 1, 2, 3; a second combination of splits 2, 3, 4; a third combination of splits 1, 3, 4; and a fourth combination of splits 1, 2, 4; each having n=203 samples). Next, cross-validation is performed using the n=271 samples, where each of the 4 models are tested on the held-out split set (n=67 samples). Next, independent validation of each of the models is performed, whereby the models are tested on independent data (e.g., the testing dataset).

Figure 11A:
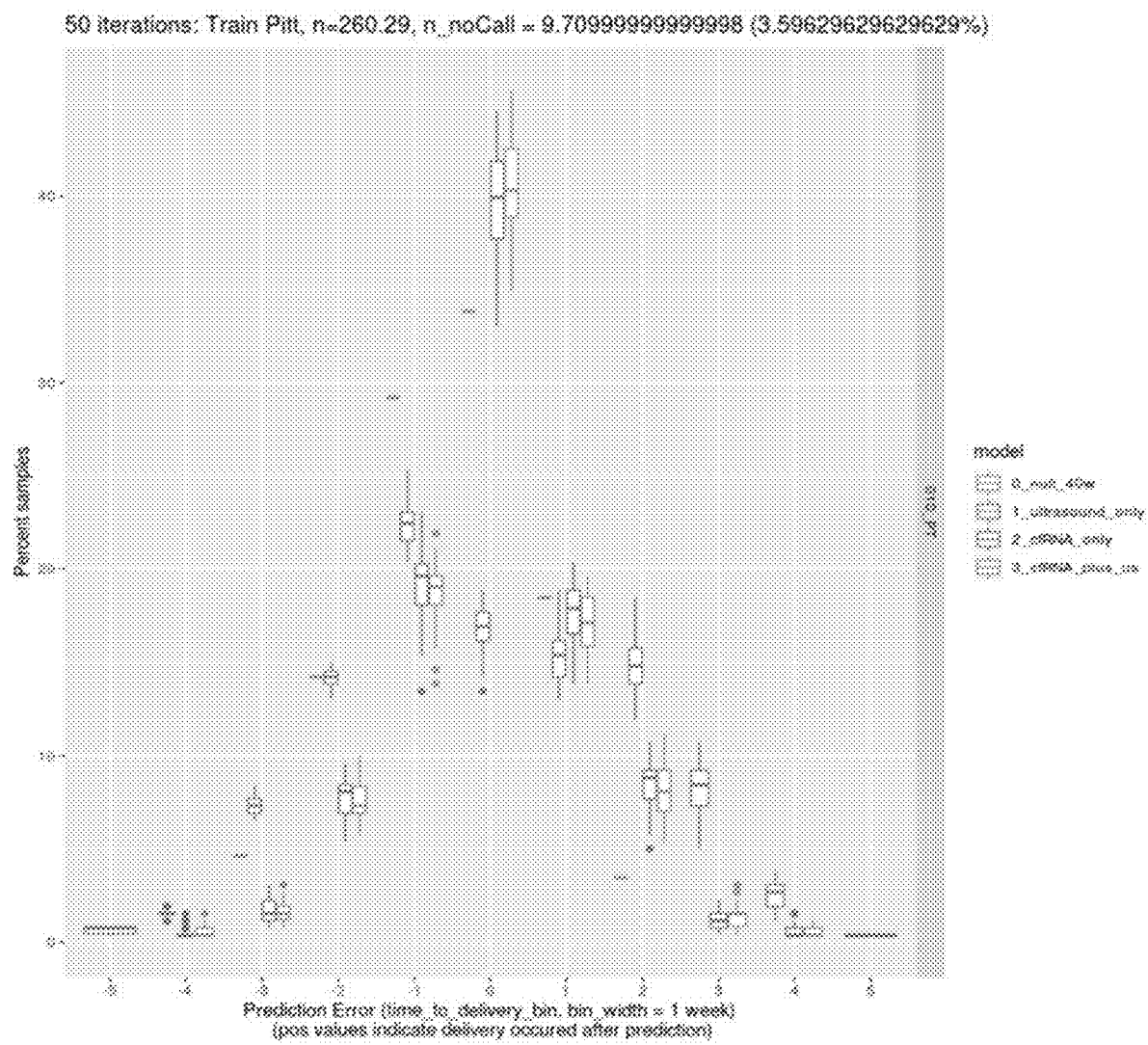
FIGS. 11A-11B show prediction error of a due date prediction model that is trained on 270 and 310 patients, respectively.
Figure 11B:
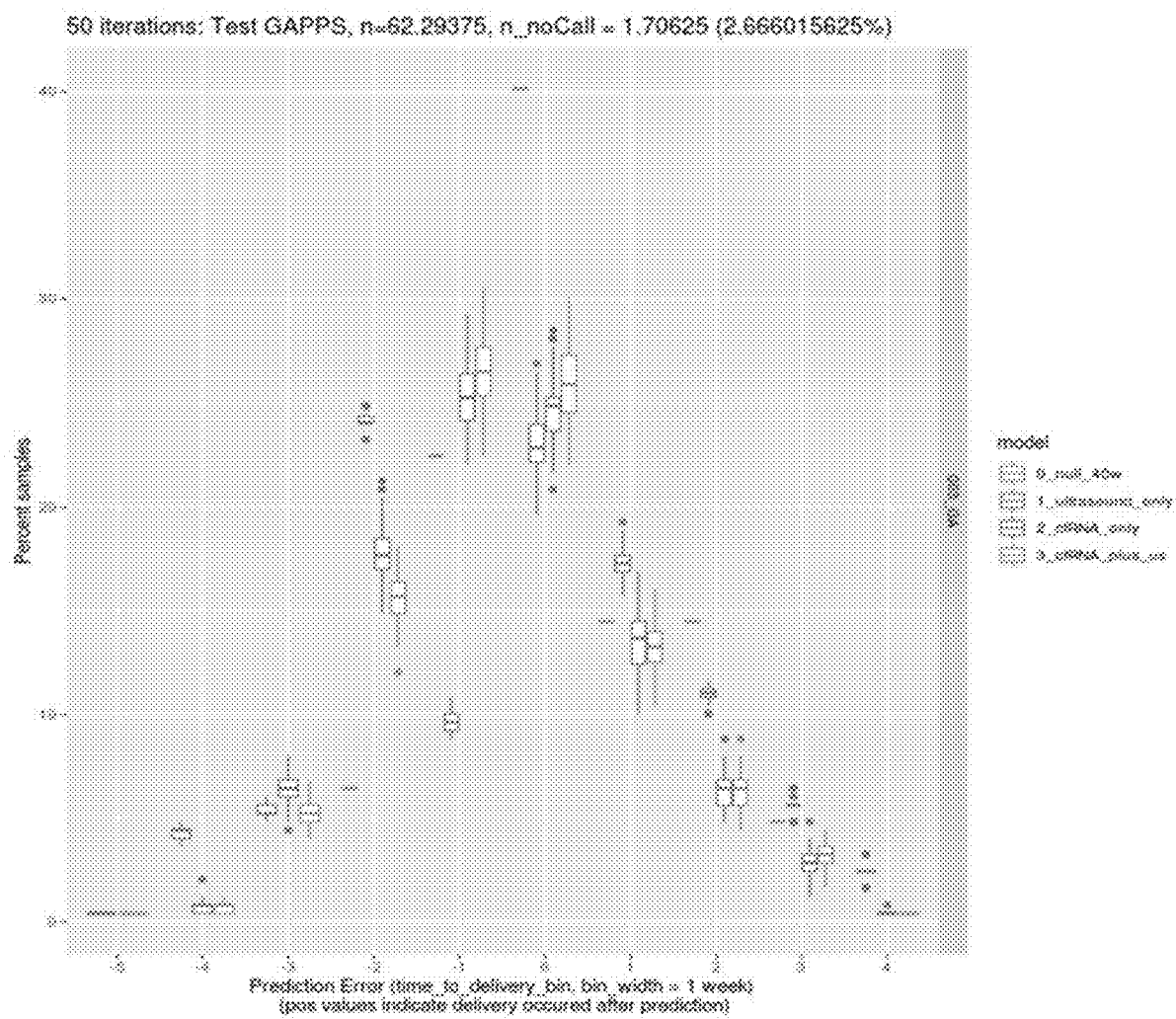

FIGS. 11A-11B show prediction error of a due date prediction model that is trained on 270 and 310 patients, respectively. The plot shows the percent of samples having a given prediction error (e.g., time to delivery bin, with a bin width of 1 week, where positive values indicate that delivery occurred after the predicted due date and negative values indicate that delivery occurred before the predicted due date). The figures show improved accuracy and lower error in due date prediction using the cfRNA-only model or the cfRNA-plus-ultrasound model, as compared to the standard-of-care (40 weeks) model and the ultrasound-only model.

Example 6: Prediction of Pre-Term Birth (PTB)

Figure 12:
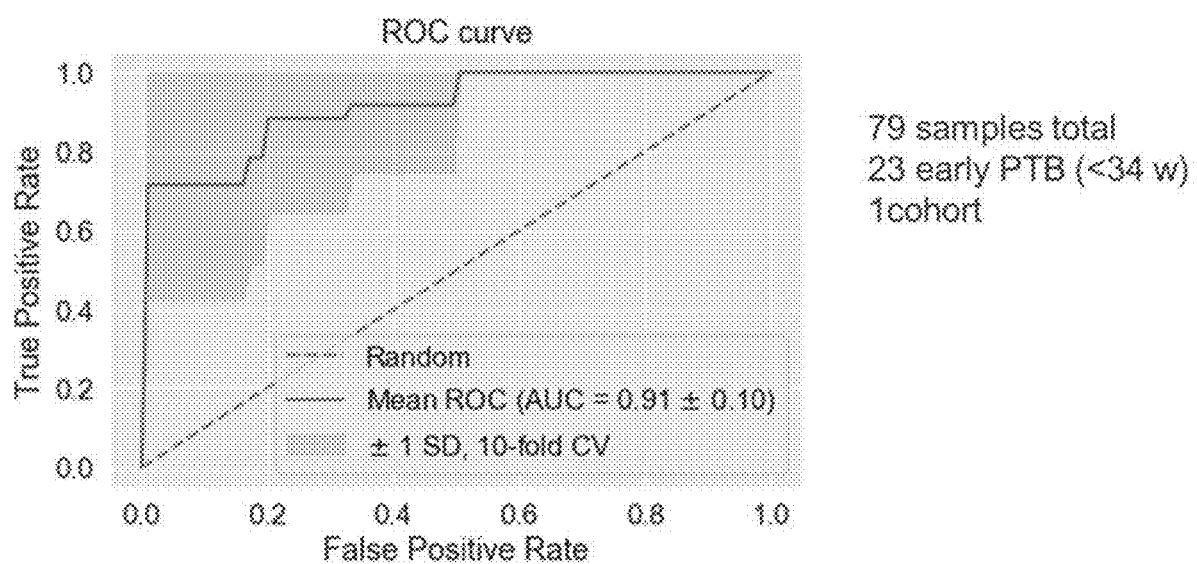
FIG. 12 shows a receiver-operator characteristic ROC) curve for a pre-term birth prediction model, using a set of 22 genes for a set of 79 samples obtained from a cohort of Caucasian subjects. The mean area-under-the-curve (AUC) for the ROC curve was 0.91±0.10.

Using systems and methods of the present disclosure, a prediction model was developed to predict a risk of pre-term birth (PTB) of a pregnant subject. The dataset obtained from a cohort of Caucasian subjects (as described in Example 4) was re-analyzed with a modified gene list, as shown in Table 8. FIG. 12 shows a receiver-operator characteristic ROC) curve for the pre-term birth prediction model, using a set of 22 genes for a set of 79 samples obtained from a cohort of Caucasian subjects. Of the 79 total samples, 23 had early PTB (defined as delivery before 34 weeks of estimated gestational age). The mean area-under-the-curve (AUC) for the ROC curve was 0.91±0.10.

TABLE 8

Genes Predictive for Pre-Term Birth
(PTB) (Caucasian)
Gene

SLC2A5
ESPN
LOX
IRX3
SPDYC
BEX1
ANK3
MTRNR2L12
MAPK10
B3GNT2
COL6A3
DDX11L10
NBPF3
U2AF1
MT1X
PHGDH
HBG2
RPL23AP7
CTD-3092A11.1
HLA-G
COL4A2
GSTM5

Figure 13A:
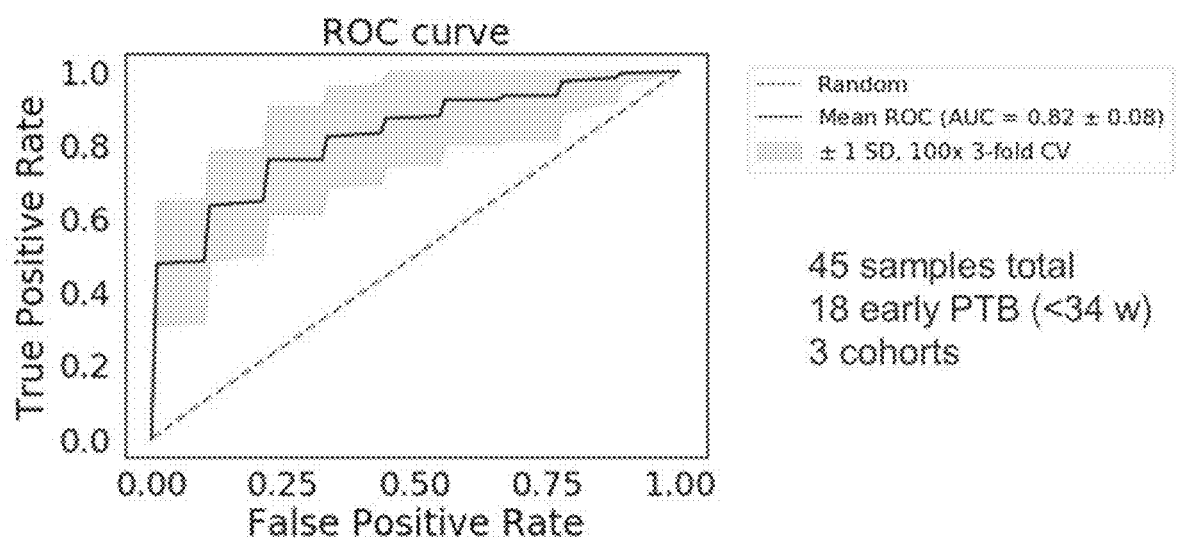
FIG. 13A shows a receiver-operator characteristic ROC) curve for a pre-term birth prediction model, using a set of genes for a set of 45 samples obtained from a cohort of subjects having African or African-American ancestries (AA cohort). The mean area-under-the-curve (AUC) for the ROC curve was 0.82±0.08.

Further, FIG. 13A shows a receiver-operator characteristic ROC) curve for a pre-term birth prediction model, using a set of genes for a set of 45 samples obtained from a cohort of subjects having African or African-American ancestries (AA cohort). Of the 45 total samples, 18 had early PTB (defined as delivery before 34 weeks of estimated gestational age). The mean area-under-the-curve (AUC) for the ROC curve was 0.82±0.08.

Figure 13B:
FIG. 13B shows a gene panel for a pre-term birth prediction model for three different AA cohorts (cohort 1, cohort 2, and cohort 3), including RAB27B, RGS18, CLCN3, B3GNT2, COL24A1, CXCL8, and PTGS2.

FIG. 13B shows a gene panel for a pre-term birth prediction model for three different AA cohorts (cohort 1, cohort 2, and cohort 3), including RAB27B, RGS18, CLCN3, B3GNT2, COL24A1, CXCL8, and PTGS2.

Figure 14A:
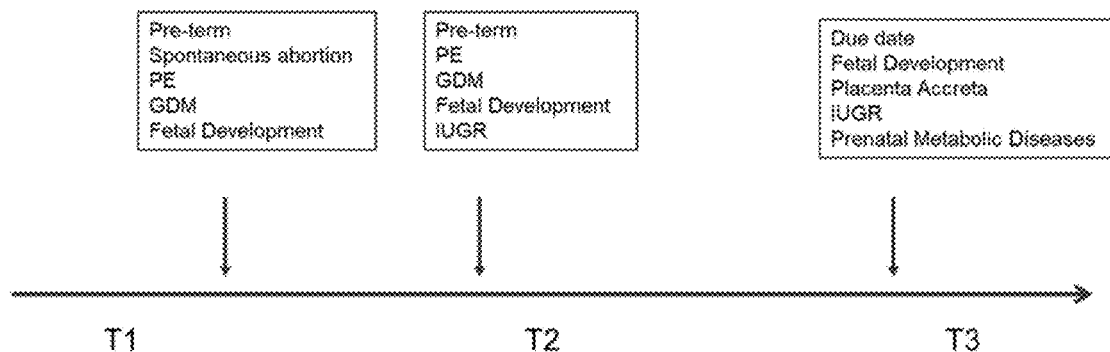
FIG. 14A shows a workflow for performing multiple assays for assessment of a plurality of pregnancy-related conditions using a single bodily sample (e.g., a single blood draw) obtained from a pregnant subject.

FIG. 14A shows a workflow for performing multiple assays for assessment of a plurality of pregnancy-related conditions using a single bodily sample (e.g., a single blood draw) obtained from a pregnant subject. Several blood draws can be performed along the pregnancy to survey and test the pregnancy progression. Blood draws obtained at specific time points (e.g., T1, T2, and T3) are tested for determining the risk of specific pregnancy-related complications that may happen several weeks away. For fetal development, longitudinal testing is performed at each blood draw (T1, T2, and T3) to provide results of the progression of fetal development. For example, a first blood sample may be obtained from a pregnant subject at time T1 (e.g., during the first trimester of pregnancy), a second blood sample may be obtained from the pregnant subject at time T2 (e.g., during the second trimester of pregnancy), and a third blood sample may be obtained from the pregnant subject at time T3 (e.g., during the third trimester of pregnancy). The blood sample obtained at time T1 may be used for assaying for pregnancy-related conditions that may be detectable or predictable in early-stage pregnancy or the first trimester of pregnancy, such as pre-term birth, spontaneous abortion, PE, GDM, and fetal development. The blood sample obtained at time T2 may be used for assaying for pregnancy-related conditions that may be detectable or predictable in mid-stage pregnancy or the second trimester of pregnancy, such as pre-term birth, PE, GDM, fetal development, and IUGR. The blood sample obtained at time T3 may be used for assaying for pregnancy-related conditions that may be detectable or predictable in late-stage pregnancy or the third trimester of pregnancy, such as due date, fetal development, placenta accreta, IUGR, prenatal metabolic diseases, and neonatal metabolic genetic diseases from RNA.

FIG. 14B shows a combination of conditions which can be tested from a single blood draw along a pregnancy progression of a pregnant subject. The blood sample obtained at time T1 may be used for assaying for pregnancy-related conditions that may be detectable or predictable in early-stage pregnancy or the first trimester of pregnancy, such as pre-term birth, preeclampsia (pregnancy-related hypertensive disorders), gestational diabetes, spontaneous abortion, and fetal development (normal and abnormal). The blood sample obtained at time T2 may be used for assaying for pregnancy-related conditions that may be detectable or predictable in mid-stage pregnancy or the second trimester of pregnancy, such as gestational age, preeclampsia (pregnancy-related hypertensive disorders), gestational diabetes, spontaneous abortion, placenta previa, placenta accreta (hemorrhage or excessive bleeding delivery), premature rupture of membrane (PROM), fetal development (normal and abnormal), and intrauterine/fetal growth restriction (IUGR). The blood sample obtained at time T3 may be used for assaying for pregnancy-related conditions that may be detectable or predictable in late-stage pregnancy or the third trimester of pregnancy, such as due date, congenital disorders, placenta previa, placenta accreta (hemorrhage or excessive bleeding delivery), premature rupture of membrane (PROM), fetal development (normal and abnormal), and intrauterine/fetal growth restriction (IUGR), post-partum depression, prenatal metabolic genetic disease, post-partum cardiomyopathy, and neonatal metabolic genetic diseases from RNA.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for treating a pregnant subject for a pregnancy-related hypertensive disorder, comprising:
   (a) obtaining a cell-free blood sample from said pregnant subject;
   (b) assaying nucleic acid molecules obtained or derived from said cell-free blood sample to determine at least one ribonucleic acid (RNA) level of at least one pregnancy-associated genomic locus, wherein said at least one pregnancy-associated genomic locus is differentially expressed in a first population of subjects with said pregnancy-related hypertensive disorder as compared to a second population of subjects without said pregnancy-related hypertensive disorder, wherein said assaying comprises selectively enriching said nucleic acid molecules for said at least one pregnancy-associated genomic locus, wherein said selectively enriching comprises use of nucleic acids having sequence complementarity with a nucleic acid sequence of said at least one pregnancy-associated genomic locus;
   (c) computer processing said at least one RNA level of said at least one pregnancy-associated genomic locus determined in (b) (i) against at least one reference RNA level of said at least one pregnancy-associated genomic locus or (ii) using a trained machine learning algorithm;
   (d) determining, based at least in part on said computer processing in (c), that said pregnant subject has or is at an elevated risk of having said pregnancy-related hypertensive disorder; and
   (e) providing a therapeutic intervention to said pregnant subject to treat said pregnancy-related hypertensive disorder, based on said determining in (d).

2. The method of claim 1, further comprising reverse transcribing ribonucleic acid (RNA) molecules derived from said cell-free blood sample to produce complementary deoxyribonucleic acid (cDNA) molecules; and assaying said cDNA molecules or derivatives thereof to determine said at least one RNA level of said at least one pregnancy-associated genomic locus.

3. The method of claim 1, wherein said assaying comprises use of nucleic acid sequencing.

4. The method of claim 1, wherein said pregnancy-related hypertensive disorder is selected from the group consisting of preeclampsia and eclampsia.

5. The method of claim 4, wherein said pregnancy-related hypertensive disorder comprises said preeclampsia.

6. The method of claim 5, wherein said at least one pregnancy-associated genomic locus is differentially expressed by subjects with preeclampsia as compared to subjects without preeclampsia, wherein said at least one pregnancy-associated genomic locus comprises a member selected from the group consisting of PAPPA2, FABP1, GPSM2, CRH, and HP.

7. The method of claim 6, wherein said at least one pregnancy-associated genomic locus comprises three or more members selected from the group consisting of PAPPA2, FABP1, GPSM2, CRH, and HP.

8. The method of claim 4, wherein said pregnancy-related hypertensive disorder comprises said eclampsia.

9. The method of claim 1, wherein said cell-free blood sample comprises a plasma sample.

10. The method of claim 1, wherein said pregnant subject is asymptomatic for said pregnancy-related hypertensive disorder.

11. The method of claim 1, wherein said computer processing in (c) comprises using said trained machine learning algorithm.

12. The method of claim 11, wherein said trained machine learning algorithm is selected from the group consisting of a linear regression, a logistic regression, an analysis of variance (ANOVA) model, a deep learning algorithm, a support vector machine (SVM), a neural network, a Random Forest, and a combination thereof.

13. The method of claim 12, wherein said trained machine learning algorithm comprises said linear regression.

14. The method of claim 12, wherein said trained machine learning algorithm comprises said ANOVA model.

15. The method of claim 11, wherein said trained machine learning algorithm is trained using a training dataset comprising: a first set of pregnant subjects with said pregnancy-related hypertensive disorder, and a second set of pregnant subjects without said pregnancy-related hypertensive disorder.

16. The method of claim 1, further comprising monitoring said pregnant subject for said pregnancy-related hypertensive disorder at least in part by assessing said pregnancy-related hypertensive disorder of said pregnant subject at a plurality of time points, wherein said assessing is based at least in part on determining whether said pregnant subject has said pregnancy-related hypertensive disorder at each of said plurality of time points.

17. The method of claim 16, wherein a difference in said assessing of said pregnancy-related hypertensive disorder of said pregnant subject among said plurality of time points is indicative of one or more clinical indications selected from the group consisting of: (i) a diagnosis of said pregnancy-related hypertensive disorder of said pregnant subject, (ii) a prognosis of said pregnancy-related hypertensive disorder of said pregnant subject, and (iii) an efficacy or non-efficacy of a therapeutic intervention for treating said pregnancy-related hypertensive disorder of said pregnant subject.

18. The method of claim 1, wherein providing said therapeutic intervention comprises administering a drug.

19. The method of claim 18, wherein said drug is selected from the group consisting of a corticosteroid, an antibiotic, a tocolytic drug, a calcium channel blocker, a cyclo-oxygenase inhibitor, an oxytocin antagonist, a betamimetic drug, magnesium sulfate, magnesium chloride, and magnesium oxide.

20. The method of claim 19, wherein said drug is said corticosteroid.

21. The method of claim 19, wherein said drug is said tocolytic drug.

22. The method of claim 19, wherein said drug is said magnesium sulfate.

23. The method of claim 1, wherein providing said therapeutic intervention comprises performing a delivery of a fetus of said pregnant subject.

24. The method of claim 1, wherein said assaying comprises use of array hybridization.

25. The method of claim 1, wherein said assaying comprises use of polymerase chain reaction (PCR).

26. The method of claim 1, wherein said selectively enriching further comprises amplifying at least a portion of said nucleic acid molecules.

27. The method of claim 1, further comprising determining that said pregnant subject has said pregnancy-related hypertensive disorder with a clinical sensitivity or clinical specificity of at least about 70%.

28. The method of claim 1, wherein said nucleic acids are primers or probes having sequence complementarity with said nucleic acid sequence of said at least one pregnancy-associated genomic locus.

29. The method of claim 28, wherein said nucleic acids are said probes having sequence complementarity with said nucleic acid sequence of said at least one pregnancy-associated genomic locus.

* * * * *